United States Patent
Sato et al.

(10) Patent No.: US 6,235,730 B1
(45) Date of Patent: May 22, 2001

(54) 3-PIPERIDYL-4-OXOQUINAZOLINE DERIVATIVES AND PHARMACEUTICAL COMPOSITIONS COMPRISING THE SAME

(75) Inventors: Motohide Sato; Takeo Katsushima; Hajime Kinoshita, all of Osaka (JP)

(73) Assignee: Japan Tobacco, Inc., Tokyo (JP)

( * ) Notice: Subject to any disclaimer, the term of this patent is extended or adjusted under 35 U.S.C. 154(b) by 0 days.

(21) Appl. No.: 09/367,242

(22) PCT Filed: Dec. 11, 1998

(86) PCT No.: PCT/JP98/05620

§ 371 Date: Oct. 26, 1999

§ 102(e) Date: Oct. 26, 1999

(87) PCT Pub. No.: WO99/31085

PCT Pub. Date: Jun. 24, 1999

(30) Foreign Application Priority Data

Dec. 12, 1997 (JP) .................................................. 9-362819
Oct. 12, 1998 (JP) ................................................ 10-288979

(51) Int. Cl.[7] ...................... C07D 401/04; C07D 409/14; C07D 413/14; A61K 31/505; A61K 31/55

(52) U.S. Cl. ...................... 514/211.11; 544/286; 544/102; 540/586; 540/522; 540/547; 540/47; 514/229.8; 514/259; 514/217; 514/220; 514/228.2

(58) Field of Search .................... 544/286, 47, 102; 514/259, 217, 220, 211.11, 228.2, 229.8; 540/586, 522, 547

(56) References Cited

U.S. PATENT DOCUMENTS

| | | | |
|---|---|---|---|
| 4,166,117 | * 8/1979 | Vincent et al. | 424/251 |
| 4,292,321 | 9/1981 | Pattison | 424/267 |
| 4,364,954 | 12/1982 | Pattison | 424/267 |
| 5,595,872 | 1/1997 | Wetterau, II et al. | 435/6 |
| 5,739,135 | 4/1998 | Biller et al. | 514/252 |
| 5,789,197 | 8/1998 | Wetterau, II et al. | 435/69.1 |
| 5,811,429 | 9/1998 | Connell et al. | 514/259 |
| 5,883,099 | 3/1999 | Biller et al. | 514/255 |
| 5,892,114 | 4/1999 | Goldmann et al. | 564/161 |
| 5,919,795 | 7/1999 | Chang et al. | 514/310 |

FOREIGN PATENT DOCUMENTS

| | | | |
|---|---|---|---|
| 0 584 446 A2 | 3/1994 | (EP) | C12N/15/12 |
| 8-151377 | 6/1996 | (JP) | C07D/401/04 |

OTHER PUBLICATIONS

Benoist et al., Microsomal Triacylglycerol Transfer Protein Prevents Presecretory Degradation of Apolipoprotein B–100, Eur. J. Biochem. 240:713–720, 1996.

* cited by examiner

Primary Examiner—Mukund J. Shah
Assistant Examiner—Hong Liu
(74) Attorney, Agent, or Firm—Fish & Richardson P.C.

(57) ABSTRACT

3-piperidyl-4-oxoquinazoline derivatives are provided, which is represented by the formula (I):

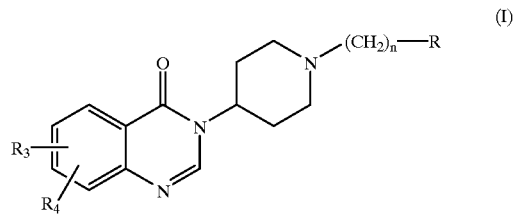

wherein R represents an amino group or a cyclic amino group such as dibenzoazepine, each of which is substituted with a substituted or unsubstituted aryl group, a substituted or unsubstituted heteroaryl group, or the like, n is an integer of 1 to 3, $R_3$ and $R_4$ independently represents a hydrogen atom, a lower alkyl group, or the like, or a pharmaceutically acceptable salt thereof. Compounds (I) of the present invention have excellent MTP-inhibitory activity. Thus, these compounds not only inhibit formation of LDL that is a cause of arteriosclerotic diseases but also regulate TG, cholesterol, and lipoproteins such as LDL in the blood and regulate cellular lipids through regulation of MTP activity. They can also be used as a new type of preventive or therapeutic agents for hyperlipemia or arteriosclerotic diseases. Furthermore, they can be used as therapeutic or preventive agents for pancreatitis, obesity, hypercholesterolemia, and hypertriglyceridemia.

17 Claims, No Drawings

US 6,235,730 B1

3-PIPERIDYL-4-OXOQUINAZOLINE DERIVATIVES AND PHARMACEUTICAL COMPOSITIONS COMPRISING THE SAME

TECHNICAL FIELD

This invention relates to a novel 3-piperidyl-4-oxoquinazoline derivative. More specifically, it relates to a pharmaceutical composition comprising a 3-piperidyl-4-oxoquinazoline derivative having microsomal triglyceride transfer protein (MTP)-inhibitory activity or its pharmaceutically acceptable salt.

BACKGROUND ART

Hyperlipemia, diabetes, and hypertension have been called risk factors in arteriosclerotic diseases such as ischemic heart diseases. Hyperlipemia means a condition in which lipids such as cholesterol increase abnormally in the blood. There are three types of hyperlima depending on the cause. One is primary hyperlipemia which results from hereditary abnormality of enzymes and proteins involved in metabolism of low density lipoprotein (LDL) and lipoprotein receptors. The second is second hyperlipemia which results from various diseases or the administration of some drugs. The third is non-genetic hyperlipemia based on supernutrition.

Lipids taken from meals are absorbed in the small intestine through the action of bile acid and are secreted into the blood as chylomicron via lymph vessels. The triglyceride (TG) moiety of secreted chylomicron is catabolized to free fatty acids by lipoprotein lipase (LPL), which is found in capillary wall, and converted into cholesteryl ester (CE)-rich chylomicron remnants, which are taken up to the liver via the chylomicron remnant receptor. In the liver, chylomicron remnants taken up and/or free fatty acids are further converted into TG and the such as by enzymes such as acyl CoA synthetase (ACS). The resulting products are then associated with apolipoprotein B synthesized on rough endoplasmic reticulum to form very low density lipoprotein (VLDL). VLDL is transferred to the Golgi apparatus and undergoes modification. The modified VLDL is secreted extracellularly to become intermediate density lipoprotein (IDL) through action of LPL. The resulting IDL is converted to LDL by HTGL (heptatic lipase). Thus, lipids are distributed to peripheral tissues.

It has been indicated that, upon the formation of chylomicron in the small intestine and VLDL in the liver, proteins having TG and CE-transferring activity were present in microsomal fractions in the small intestine and the liver. In 1985, Wetterau et al. isolated and purified the protein, i.e., microsomal triglyceride transfer protein (MTP), from microsomal fractions in bovine liver (Wetterau, J. R. et al.: Chem. Phys. Lipids 38, 205–222 (1985)). However, MTP was not spotlighted in the field of clinical medicine until the cause of abetalipoproteinemia was reported to be the defect of MTP in 1993. This disease is characterized by the near absence of apolipoprotein B in serum but a lack of abnormality in apolipoprotein B-related genes. Serum cholesterol is below 50 mg/dl, and serum triglyceride levels are extremely low. Another characteristic of the disease is that lipoproteins containing apolipoprotein B such as chylomicron, VLDL, and LDL are completely absent in the blood. These findings indicate that MTP is a necessary protein for conjugation of apolipoprotein B with TG and CE, i.e., for forming VLDL and chylomicron, and plays a fundamental role in secreting these lipoproteins.

Since lipids are by nature insoluble in water, they associate with a hydrophilic protein called apolipoprotein in the blood and are present as lipoproteins. VLDL, IDL, LDL and chylomicron, which are involved in hyperlipemia, are all lipoproteins.

MTP is present in microsomal fractions in hepatocytes and epithelial cells of the small intestine and is responsible for intracellular transfer of TG and CE. Accompanying the synthesis of apolipoprotein B (apolipoprotein B 100 in the liver and apolipoprotein B48 in the small intestine), TG and CE become associated with their corresponding apolipoproteins through the transferring action of MTP to form VLDL or chylomicron in the liver and small intestine. As a result, these lipoproteins are secreted extracellularly as VLDL from the liver and as chylomicron from the small intestine. MTP is necessary to assemble these lipoproteins. Thus, formation of lipoproteins can be inhibited by inhibiting MTP activity to thereby prevent transfer to lipids such as TG to apolipoproteins.

It has become apparent that LDL is intimately involved in the development of arteriosclerotic diseases in general. LDL penetrates the endothelium of blood vessels and is deposited in an intercellular matrix of the vessel wall. Oxidative degeneration occurring there triggers a series of inflammatory reactions induced by lipid peroxides and degenerated proteins to thereby cause invasion by macrophages and vascular smooth muscles, deposition of lipid, proliferation of cells, and increases in the intercellular matrix in blood vessel walls. Arteriosclerotic lesions are then formed. Thus, arteriosclerotic diseases can be prevented or treated by decreasing LDL.

As described above, it is possible to prevent formation of lipoproteins such as VLDL and LDL by inhibiting MTP activity. Therefore, TG, cholesterol, and lipoproteins such as LDL in the blood and lipids in the cells can be controlled by regulating MTP activity. Compounds having such activity are expected to become new drugs for preventing and treating not only hyperlipemia or arteriosclerotic diseases but also pancreatitis, obesity, hypercholesterolemia, hypertriglyceridemia, and the such as.

Recently, compounds with MTP-inhibitory activity have been reported.

For example, Eur. J. Biochem. 240, 713 to 720 (1996) discloses 4'-bromo-3'-methylmethaqualone as a compound having MTP-inhibitory activity. However, the literature neither discloses nor suggests compounds having such structures as those of the compounds of the present invention.

Unexamined published Japanese paten application (JP-A) Hei 6-38761 (EP 584446) discloses 2-[1-(3,3-diphenylpropyl)-4-piperidinyl]-2,3-dihydro-3-oxo-1H-isoindole hydrochloride as a compound with MTP-inhibitory activity. However, activity with such structures as those of the compounds of the present invention are neither disclosed nor suggested in the publication.

Furthermore, as a compound with MTP-inhibitory activity, JP-A-Hei 7-165712 (U.S. Pat. No. 5,595,872) discloses 2-(4-piperidyl)-2,3-dihydro-3-1H-isoindole compounds such as 2-[1-[2-(5H-dibenzo[a,d]cyclohepten-5-yl) ethyl]-4-piperidyl]-2,3-dihydro-3-oxo-1H-isoindole, and WO 96/26205 discloses isoindole compounds such as 9-[3-[4-(2,3-dihydro-1-oxo-1H-isoindole-2-yl)-1-piperidyl]-propyl]-N-propyl9H-fluorene-9-carboxamide. However, none of these publications disclose or suggest compounds with such structures as those of the compounds of the present invention.

WO 96/40640 discloses biphenyl-2-carboxylic acid tetrahydroisoquinolin-6-yl amide derivatives such as 4'-trifluoromethyl-biphenyl-2-carboxylic acid [2-(1,5a,6,9, 9a,9b-hexahydro-4H-dibenzofuran-4a-ylmethyl)-1,2,3,4-tetrahydroiso-quinolin-6-yl]amide as an MTP-inhibitor. However, the publication neither discloses nor suggests compounds with such structures as those of the compounds of the present invention.

There are many reports showing compounds having the 3-piperidyl-4-oxoquinazoline structure similar to the compounds of the present invention.

For example, JP-A-Sho 53-38784 (U.S. Pat. No. 4,166,117) discloses N-substituted quinazoline compounds such as 1-[(2,6-dimethylphenoxy)-2-ethyl]-4-[4-oxo[3H]quinazolin-3-yl]piperidine as compounds with antihypertensive activity. However, the publication does not disclose compounds with structures such as those of the compounds of the present invention. Moreover, the publication neither discloses nor suggests that the compounds have MTP-inhibitory activity.

JP-A-Hei 8-151377 discloses quinazoline derivatives such as N-(2,6-dichloro-4-nitrophenyl)-4-(1,2,3,4-tetrahydro-1,6-dimethyl-2,4-dioxoquinazolin-3-yl)-1-piperidine acetamide. However, the compounds disclosed in the publication show adenosine uptake inhibitory activity, and there is neither description nor suggestion that the compounds have MTP-inhibitory activity.

U.S. Pat. No. 4,364,954 discloses diphenyl propaneamine compounds such as 1-[1-[3-[bis(4-fluorophenyl)amino]propyl]-4-piperidyl]-1,3-dihydro-2H-benzimidazol-2-one. The compounds are disclosed as a therapeutic agent for schizophrenia, not as an MTP inhibitor as in the present invention. Furthermore, the publication neither discloses nor suggests compounds with structures such as those of the compounds of the present invention.

EP 802188 discloses that hetero-bonded phenylglycinol amides having a 4-oxoquinazonyl group are effective against atherosclerotic diseases. However, the publication neither discloses nor suggests compounds with structures such as those of the compounds of the present invention.

DISCLOSURE OF THE INVENTION

The present inventors ardently searched for compounds as described above with MTP-inhibitory activity. As a result, they found, rather surprisingly, that compounds with a 3-piperidyl-4-oxoquinazoline structure that have an aminoalkyl group at position 1 of the piperidyl group exhibit excellent MTP-inhibitory activity.

The present invention relates to 3-piperidyl-4-oxoquinazoline derivatives as shown in (1) to (13) below or pharmaceutically acceptable salts thereof, and pharmaceutical compositions comprising the same.

(1) A 3-piperidyl-4-oxoquinazoline derivative represented by the formula (I):

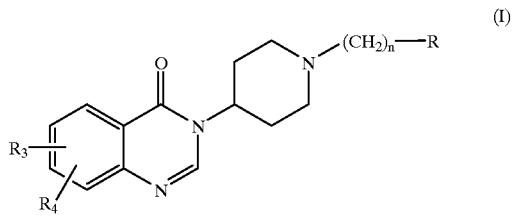

(I)

wherein R represents the formula (i):

(i)

wherein $R_1$ and $R_2$ may be the same or different and represent a hydrogen atom; a lower alkyl group with 1 to 4 carbon atoms; an aralkyl group; a benzoyl group; a cycloalkyl group with 3 to 7 carbon atoms; an aryl group; or a heteroaryl group with 1 to 3 hetero atoms selected from nitrogen, sulfur, and oxygen atoms (where the cycloalkyl, aryl, or heteroaryl group may be substituted with 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, an amino group, an amino group substituted with a lower alkyl group with 1 to 4 carbon atoms, a hydroxyl group, a phenoxy group, and a sulfo group), provided that one of $R_1$ to $R_2$ is not a hydrogen atom, or the formula (ii):

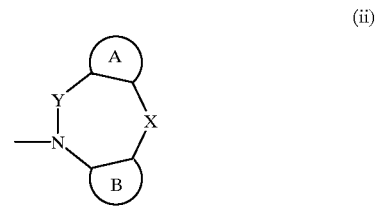

(ii)

wherein A and B may be the same or different and represent an aromatic hydrocarbon ring; an aromatic heterocyclic ring containing 1 to 3 hetero atoms selected from nitrogen, sulfur, and oxygen atoms; a cycloalkane ring with 3 to 7 carbon atoms; or a cycloalkene ring with 5 to 7 carbon atoms (where the aromatic hydrocarbon, aromatic heterocyclic, cycloalkane, or cycloalkene ring may have a 1 to 3 substituents selected from a halogen atom, a lower alkyl group with 1 to 4 carbon atoms, a lower haloalkyl group with 1 to 4 carbon atoms, a hydroxyl group, a nitro group, a lower alkoxy group with 1 to 4 carbon atoms, an amino group, an amino group substituted with a lower alkyl group having 1 to 4 carbon atoms, and a sulfo group), X represents a single bond, a straight chain or branched lower alkylene group with 1 to 4 carbon atoms, a straight chain or branched lower alkenylene group with 2 to 4 carbon atoms (where the lower alkylene or lower alkenylene group may have substituent(s) selected from a halogen atom, a hydroxyl group, a nitro group, a lower alkoxy group with 1 to 4 carbon atoms, an amino group, and a sulfo group), an oxygen atom, a sulfur atom, an amino group which may be substituted with a lower alkyl group with 1 to 4 carbon atoms, a carbonyl group, —O—Z—, —Z—O—, —S—Z—, —Z—S—, —NH—Z—, —NR₅Z—, —Z—NH—, or —Z—NR₅— (where Z represents a lower alkylene group with 1 to 4 carbon atoms or a carbonyl group, and $R_5$ represents a lower alkyl group with 1 to 4 carbon atoms), Y represents a single bond, a straight chain or branched lower alkylene group with 1 to 4 carbon atoms, or a carbonyl group; n represents an interger of 1 to 4; and $R_3$ and $R_4$ may be the same or different and represent a hydrogen atom, a lower alkyl group with 1 to 4 carbon atoms, a halogen atom, a lower haloalkyl group with 1 to 4 carbon atoms, a hydroxyl group, an amino group or a nitro group, or pharmaceutically acceptable salt thereof.

(2) The 3-piperidyl-4-oxoquinazoline derivative as described in (1), wherein R represents the formula (i'):

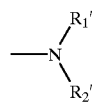
(i')

wherein $R_1'$ and $R_2'$ may be the same or different and represent a cycloalkyl group with 3 or 7 carbon atoms; an aryl group; or a hetero aryl group with 1 to 3 hetero atoms selected from nitrogen, sulfur, and oxygen atoms (where the cycloalkyl, aryl, or heteroaryl group may have 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, an amino group, an amino group substituted with a lower alkyl group having 1 to 4 carbon atoms, a hydroxyl group, and a sulfo group); or the formula (ii'):

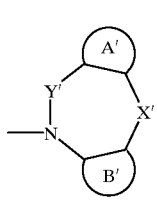
(ii')

wherein A' and B' may be the same or different and represent an aromatic hydrocarbon ring; an aromatic heterocyclic ring containing 1 to 3 hetero atoms selected from nitrogen, sulfur, and oxygen atoms; a cycloalkene ring with 3 to 7 carbon atoms; a cycloalkene ring with 5 to 7 carbon atoms (where the aromatic hydrocarbon, aromatic heterocyclic, cycloalkene, or cycloalkene ring may have 1 to 3 substituents selected from a halogen atom, a lower alkyl group with 1 to 4 carbon atoms, a lower haloalkyl group with 1 to 4 carbon atoms, a hydroxyl group, a nitro group, a lower alkoxy group with 1 to 4 carbon atoms, an amino group, an amino group substituted with a lower alkyl group having 1 to 4 carbon atoms, and a sulfo group), X' represents a single bond, a straight chain or branched lower alkylene group with 1 to 4 carbon atoms, a straight chain or branched lower alkenylene group with 2 to 4 carbons (where the lower alkylene or lower alkenylene group may have substituent(s) selected from a halogen atom, a hydroxyl group, a nitro group, a lower alkoxy group with 1 to 4 carbon atoms, an amino group, and a sulfo group), an oxygen atom, a sulfur atom, an imino group which may be substituted with a lower alkyl group having 1 to 4 carbon atoms, a carbonyl group, —O—Z'—, —Z'—O—, —S—Z'—, —Z'—S—, —NH—Z'—, —NR$_5$'—Z'—, —Z'—NH—, or —Z'—NR$_5$— (where Z' represents a lower alkylene group with 1 to 4 carbon atoms or a carbonyl group, and R$_5$' represents a lower alkyl group with 1 to 4 carbon atoms), Y' represents a single bond, a straight chain or branched lower alkylene group with 1 to 4 carbon atoms, or a carbonyl group, $R_3$ and $R_4$ may be the same or different and represent a hydrogen atom or a lower alkyl group with 1 to 4 carbon atoms, or a pharmaceutically acceptable salt thereof.

(3) The 3-piperidyl-4-oxoquinazoline derivative as described in (2), wherein R represents formula (i"):

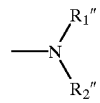
(i")

wherein $R_1''$ and $R_2''$ may be the same or different and represent a cycloalkyl group with 3 to 7 carbon atoms, an aryl group, or a heteroaryl group containing 1 to 3 hetero atoms selected from nitrogen, sulfur, and oxygen atoms (where the cycloalkyl, aryl, or heteroaryl group may have 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group), or the formula (ii"):

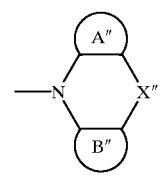
(ii")

wherein A" and B" may be the same or different and represent an aromatic hydrocarbon ring or an aromatic heterocyclic ring with 1 to 3 hetero atoms selected from nitrogen, sulfur, and oxygen atoms (where the aromatic hydrocarbon or aromatic heterocyclic ring may have 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group), X" represents a single bond, a straight chain or branched lower alkylene group with 1 to 4 carbon atoms, a straight chain or branched lower alkenylene group with 2 to 4 carbon atoms (where the lower alkylene or lower alkenylene group may have substituent(s) selected from a halogen atom, a hydroxyl group, and a lower alkoxy group with 1 to 4 carbon atoms), an oxygen atom, a sulfur atom, an imino group which may be substituted with a lower alkyl group having 1 to 4 carbon atoms, a carbonyl group, —O—Z"—, —S—Z"—, —NH—Z"—, or —NR$_5$"—Z"— (where Z" represents a lower alkylene group with 1 to 4 carbon atoms or a carbonyl group, and R$_5$" represents a lower alkyl group with 1 to 4 carbon atoms), and $R_3$ and $R_4$ are both hydrogen atoms, or pharmaceutically acceptable salt thereof.

(4) The 3-piperidyl-4-oxoquinazoline derivative as described in (3), wherein R represents the formula (i"):

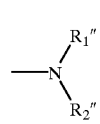
(i")

wherein $R_1''$ and $R_2''$ may be the same or different and represent a cycloalkyl group with 3 to 7 carbon atoms; an aryl group; a heteroaryl group with 1 to 3 hetero groups selected from nitrogen, sulfur, and oxygen atoms (where the cycloalkyl, aryl, or heteroaryl group may have 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group);
or a pharmaceutically acceptable salt thereof.

(5) The 3-piperidyl-4-oxoquinazoline derivative as described in (4), wherein $R_1"$ and $R_2"$ may be the same or different and represent a cyclohexyl group, a phenyl group, a pyridyl group, a pirazinyl group, a pyrimidinyl group, a pyridazinyl group, a thienyl group, a furyl group, or a pyrrolyl group (where each of the above groups may have 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group), or a pharmaceutically acceptable salt thereof.

(6) The 3-piperidyl-4-oxoquinazoline derivative as described in (5), wherein R represents a diphenylamino group, an N-phenyl-N-thienylamino group, an N-phenyl-N-pyridylamino group, a dipyridylamino group, an N-phenyl-N-pyrimidylamino group (where each of the above groups may have 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group), or a pharmaceutically acceptable salt thereof.

(7) The 3-piperidyl-4-oxoquinazoline derivative as described in (3) in which R represents formula (ii"):

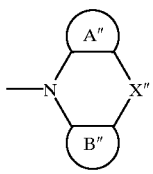

(ii")

wherein A" and B" may be the same or different and represent an aromatic hydrocarbon ring or an aromatic heterocyclic ring containing 1 to 3 hetero atoms selected from nitrogen, sulfur, and oxygen atoms (where the aromatic hydrocarbon or aromatic heterocyclic ring may have 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group), X" represents a single bond, a straight chain or branched lower alkylene group with 1 to 4 carbon atoms, a straight chain or branched lower alkenylene group with 2 to 4 carbon atoms (where the lower alkylene or lower alkenylene group may have substituent(s) selected from a halogen atom, a hydroxyl group, and a lower alkoxy group with 1 to 4 carbon atoms), an oxygen atom, a sulfur atom, an imino group that may be substituted with a lower alkyl group with 1 to 4 carbon atoms, a carbonyl group, —O—Z"—, —S—Z"—, —NH—Z"—, or —NR$_5$"—Z"— (where Z" represents a lower alkylene group with 1 to 4 carbon atoms or a carbonyl group, and R$_5$" represents a lower alkyl group with 1 to 4 carbon atoms),
or a pharmaceutically acceptable salt thereof.

(8) The 3-piperidyl-4-oxoquinazoline derivative as described in (7), wherein A" and B" may be the same or different and represent a benzene ring, a pyridine ring, a pyrazine ring, a pyrimidine ring, or a pyridazine ring (where each of the above rings may have 1 to 3 substituents selected from a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group), or a pharmaceutically acceptable salt thereof.

(9) The 3-piperidyl-4-oxoquinazoline derivative as described in (8), wherein R represents a carbazol-9-yl group, a phenoxazin-10-yl group, a phenothiazin-10-yl group, an acridon-10-yl group, a 9,9-dimethylacridan-10-yl group, a 10,11-dihydro-5H-dibenzo[b,f]azepin-5-yl group, a 10,11-dihydro-2-hydroxy-5H-dibenzo[b,f]azepin-5-yl group, a 10,11-dihydro-10-hydroxy-5H-dibenzo[b,f]azepin-5-yl group, a 5H-dibenzo[b,f]azepin-5-yl group, a 5,11-dihydrodibenzo[b,e][1,4]oxazepin-5-yl group, a 10,11-dihydro-11-oxo-5H-dibenzo[b,e][1,4]diazepin-5-yl group, a 11-hydro-10-methyl-11-oxo-5H-dibenzo[b,e][1,4]diazepin-5-yl group, or a pharmaceutically acceptable salt thereof.

(10) The 3-piperidyl-4-oxoquinazoline derivative as described in (3), which is selected from the group consisting of 3-[1-[2-[N-(2-methylphenyl)-N-phenylamino]ethyl]piperidin-4-yl]-3H-quinazolin-4-one, 3-[1-[2-(10,11-dihydro-5H-dibenzo[b,f]-azepin-5-yl)ethyl]piperidin-4-yl]-3H-quinazolin-4-one, 3-[1-[2-(10,11-dihydro-10-hydroxy-5H-dibenzo[b,f]azepin-5-yl)-ethyl]-piperidin-4-yl]-3H-quinazolin-4-one, 3-[1-[2-(10,11-dihydro-2-hydroxy-5H-dibenzo[b,f]azepin-5-yl)ethyl]piperidin-4-yl]-3H-quinazolin-4-one, 3-[1-[2-(5,11-dihydrodibenzo[b,e][1,4]-oxazepin-5-yl)ethyl]piperidin-4-yl]-3H-quinazolin-4-one, or a pharmaceutically acceptable salt thereof.

(11) A pharmaceutical composition comprising the 3-piperidyl-4-oxoquinazoline derivative as described in (1) to (10) or a pharmaceutically acceptable salt thereof as an active ingredient.

(12) A microsomal triglyceride transfer protein (MTP)-inhibitor comprising the 3-piperidyl-4-oxoquinazoline derivative as described in (1) to (10) or a pharmaceutically acceptable salt thereof as an active ingredient.

(13) A therapeutic or preventive agent for hyperlipemia or arteriosclerosis comprising the 3-piperidyl-4-oxoquinazoline derivative as described in (1) to (10) or a pharmaceutically acceptable salt thereof as an active ingredient.

"A lower alkyl group with 1 to 4 carbon atoms" used herein specifically means methyl, ethyl, propyl, isopropyl, butyl, isobutyl, sec-butyl, tert-butyl, etc.

"An aralkyl group" means an alkyl group with 1 to 4 carbon atoms substituted with an aryl group described below. Specific examples thereof include benzyl, benzhydryl, trityl, phenetyl, 3-phenylpropyl, 2-phenylpropyl, 4-phenylbutyl, naphthylmethyl, 2-naphthylethyl, 4-biphenylmethyl, 3-(4-biphenyl) propyl, etc.

"A cycloalkyl group with 3 to 7 carbon atoms" specifically includes cyclopropyl, cyclobutyl, cyclopentyl, cyclohexyl, and cycloheptyl.

"An aryl group" means phenyl, naphthyl, biphenyl, etc.

"A heteroaryl group containing 1 to 3 hetero atoms selected from nitrogen, sulfur, and oxygen atoms" means a 5- or 6-membered heteroaryl group containing 1 to 3 hetero atoms selected from nitrogen, sulfur, and oxygen. Specifically, it includes thienyl, furyl, pyrrolyl, imidazolyl, pyrazolyl, thiazolyl, isothiazolyl, oxazolyl, isooxazolyl, triazolyl, pyridyl, pyrazinyl, pyrimidinyl, pyridazinyl, etc.

"A halogen atom" means fluorine, chlorine, bromine, etc.

"A lower haloalkyl group with 1 to 4 carbon atoms" means a lower alkyl group with substituted halogen atom(s). Specific examples thereof include fluoromethyl, chloromethyl, bromomethyl, difluoromethyl, dichloromethyl, trifluoromethyl, trichloromethyl, chloroethyl, difluoroethyl, trifluoroethyl, pentachloroethyl, bromopropyl, dichloropropyl, trifluorobutyl, etc.

"A lower alkoxy group with 1 to 4 carbon atoms" specifically includes methoxy, ethoxy, propoxy, isopropoxy, butoxy, isobutoxy, sec-butoxy, tert-butoxy, etc.

"An amino group substituted with a lower alkyl group having 1 to 4 carbon atoms" means an amino group that is mono- or di-substituted with a lower alkyl group with 1 to 4 carbon atoms. Specific examples thereof include methylamino, ethylamino, propylamino, isopropylamino, butylamino, isobutylamino, sec-butylamino, tert-butylamino, dimethylamino, diethylamino, dipropylamino, diisopropylamino, methylethylamino, methylbutylamino, etc.

"An aromatic hydrocarbon ring" means benzene, naphthalene, etc.

"An aromatic heterocyclic ring containing 1 to 3 hetero atoms selected from nitrogen, sulfur, and oxygen atoms" means a 5- or 6-membered aromatic heterocyclic ring containing 1 to 3 hetero atoms selected from nitrogen, sulfur, and oxygen atoms. It specifically includes thiophene, furan, pyrrole, imidazole, pyrazole, thiazole, isothiazole, oxazole, isooxazole, triazole, pyridine, pyrazine, pyrimidine, pyridazine, etc.

"A cycloalkane ring with 3 to 7 carbon atoms" specifically includes cyclopropane, cyclobutane, cyclopentane, cyclohexane, cycloheptane, etc.

"A cycloalkene ring with 5–7 carbon atoms" specifically includes cyclopentene, cyclohexene, cycloheptene, cyclohexadiene, cycloheptadiene, etc.

"A straight chain or branched lower alkylene group with 1 to 4 carbon atoms" specifically includes methylene, ethylene, trimethylene, tetramethylene, propylene, ethylethylene, dimethylmethylene, etc.

"A straight chain or branched lower alkenylene group with 2 to 4 carbon atoms" specifically includes vinylene, propenylene, butenylene, butadienylene, methylvinylene, ethylvinylene, 3-methylpropenylene, etc.

"An imino group that may be substituted with a lower alkyl group having 1 to 4 carbon atoms" means a secondary amino group that may be substituted with a lower alkyl group having 1 to 4 carbon atoms. Specifically, it includes imino, methylimino, ethylimino, propylimino, isopropylimino, butylimino, isobutylimino, etc.

Hereunder, the above-mentioned embodiments are described in more detail but are not necessarily limited to that description.

The "lower alkyl group with 1 to 4 carbon atoms" represented by $R_1$ or $R_2$ is preferably methyl or ethyl.

The "aralkyl group" represented by $R_1$ or $R_2$ is preferably benzyl or benzhydryl.

The "cycloalkyl group with 3 to 7 carbon atoms" represented by $R_1$ to $R_2$ is preferably a cycloalkyl group with 5 to 7 carbon atoms. A cyclohexyl group is particularly preferable.

The "aryl group" represented by $R_1$ or $R_2$ is preferably a phenyl group.

The "heteroaryl group containing 1 to 3 hetero atoms selected from nitrogen, sulfur, and oxygen atoms" represented by $R_1$ or $R_2$ is preferably thienyl, furyl, pyrrolyl, pyridyl, pyrazinyl, pyrimidinyl, or pyridazinyl. Thienyl, pyridyl, and pyrimidinyl are particularly preferable.

The "halogen atom" as a substituent of the cycloalkyl, aryl, or heteroaryl group represented by $R_1$ or $R_2$ is preferably fluorine or chlorine.

The "lower alkyl group with 1 to 4 carbon atoms" as a substituent of the cycloalkyl, aryl or heteroaryl group represented by $R_1$ or $R_2$ is preferably methyl, ethyl, propyl, isopropyl, or butyl. A methyl group is particularly preferable.

The "lower haloalkyl group with 1 to 4 carbon atoms" as a substituent of the cycloalkyl, aryl, or heteroaryl group represented by $R_1$ or $R_2$ is preferably a trifluoromethyl group.

The "lower alkoxy group with 1 to 4 carbon atoms" as a substituent of the cycloalkyl, aryl, or heteroaryl group represented by $R_1$ or $R_2$ is preferably a methoxy group.

The "amino group substituted with a lower alkyl group having 1 to 4 carbon atoms" as a substituent of the cycloalkyl, aryl, or heteroaryl group represented by $R_1$ or $R_2$ is preferably methylamino, ethylamino, dimethylamino, or diethylamino.

The expression, "may be substituted with 1 to 3 substituents," with respect to the cycloalkyl, aryl, or heteroaryl group represented by $R_1$ or $R_2$, preferably means that these groups may be substituted with 1 to 2 substituents, more preferably with one substituent.

Preferable substituents of the cycloalkyl group represented by $R_1$ or $R_2$ are methyl, fluorine, chlorine, or amino.

Preferable substituents of the aryl group represented by $R_1$ or $R_2$ are methyl, ethyl, propyl, isopropyl, butyl, fluorine, chlorine, trifluoromethyl, nitro, methoxy, or phenoxy. A methyl group is particularly preferable.

A preferable substituent of the heteroaryl group represented by $R_1$ or $R_2$ is a methyl group.

The combination of the substituents in formula (i) is not particularly limited as long as it falls within the above definition. Formula (i) is preferably dicyclohexylamino, diphenylamino, N-phenyl-N-thienylamino, N-phenyl-N-pyridylamino, dipyridylamino, or N-phenyl-N-pyridylamino. Diphenylamino and dipyridylamino are particularly preferable. Substituents of $R_1$ and $R_2$ are defined as above.

The "aromatic hydrocarbon ring" represented by A or B is preferably a benzene ring.

The "aromatic heterocyclic ring containing 1 to 3 hetero atoms selected from nitrogen, sulfur, and oxygen atoms" represented by A or B is preferably pyridine or pyrimidine, with pyridine being particularly preferable.

The "cycloalkane ring with 3 to 7 carbon atoms" represented by A or B is preferably cyclopentane, cyclohexane, or cycloheptane.

The "cycloalkene ring with 5 to 7 carbon atoms" represented by A or B is preferably cyclopentene, cyclohexene, or cycloheptene.

The "halogen atom" as a substituent or the aromatic hydrocarbon, aromatic heterocyclic, cycloalkane, or cycloalkene ring represented by A or B is preferably fluorine or chlorine.

The "lower alkyl group with 1 to 4 carbon atoms" as a substituent of the aromatic hydrocarbon, aromatic heterocyclic, cycloalkane, or cycloalkene ring represented by A or B is preferably methyl or ethyl.

The "lower haloalkyl group with 1 to 4 carbon atoms" as a substituent of the aromatic hydrocarbon, aromatic heterocyclic, cycloalkane, or cycloalkene ring represented by A or B is preferably a trifluoromethyl group.

The "lower alkoxyl group with 1 to 4 carbon atoms" as a substituent of the aromatic hydrocarbon, aromatic heterocyclic, cycloalkane, or cycloalkene ring represented by A or B is preferably a methoxy group.

The "amino group substituted with a lower alkyl group having 1 to 4 carbon atoms" as a substituent of the aromatic hydrocarbon, aromatic heterocyclic, cycloalkane, or cycloalkene ring represented by A or B is preferably methylamino, ethylamino, dimethylamino, or diethylamino.

The expression, "may be substituted with 1 to 3 substituents," with respect to the aromatic hydrocarbon, aromatic heterocyclic, cycloalkane, or cycloalkene ring represented by A or B, preferably means that these groups may be substituted with 1 to 2 substituents, and more preferably with one substituent.

The substituent of the cycloalkane ring represented by A or B is preferably methyl, fluorine, chlorine, or amino.

The substituent of the cycloalkene ring represented by A or B is preferably methyl, fluorine, chlorine, or amino.

The substituent of the aromatic hydrocarbon ring represented by A or B is preferably methyl, ethyl, fluorine, chlorine, trifluoromethyl, nitro, hydroxyl, sulfo, or methoxy. A hydroxyl group is particularly preferable.

The substituent of the aromatic heterocyclic ring represented by A or B is preferably methyl or hydroxyl.

The "straight chain or branched lower alkylene group with 1 to 4 carbon atoms" represented by X is preferably methylene, ethylene, or dimethylmethylene.

The "straight chain or branched lower alkenylene group with 2 to 4 carbon atoms" represented by X is preferably a vinylene group.

The "halogen atom" as a substituent of the lower alkylene or lower alkenylene group represented by X is preferably fluorine or chlorine.

The "lower alkoxy group with 1 to 4 carbon atoms" as a substituent of the lower alkylene or lower alkenylene group represented by X is preferably a methoxy group.

The term "may be substituted" with respect to the lower alkylene or lower alkenylene group represented by X preferably means that these groups may be substituted with one substituent.

The substituent of the lower alkylene group represented by X is fluorine, hydroxyl, methoxy, or sulfo. A hydroxyl group is particularly preferable.

The preferable substituent of the lower alkenylene represented by X is fluorine, hydroxyl, methoxy, or sulfo.

The preferable "imino group that may be substituted with a lower alkyl group having 1 to 4 carbon atoms" represented by X is imino or methylimino.

The preferable "lower alkylene group with 1 to 4 carbon atoms" represented by Z is a methylene group.

The preferable "lower alkyl group with 1 to 4 carbon atoms" represented by $R_5$ is methyl or ethyl. A methyl group is particularly preferable.

The preferable "straight chain or branched lower alkylene group with 1 to 4 carbon atoms" represented by Y is a methylene group.

The combination of the substituents in formula (ii) is not particularly limited as long as it falls within the above definition. Formula (ii) is preferably a carbazol-9-yl group, a phenoxazin-10-yl group, a phenothiazin-10-yl group, an acridon-10-yl group, a 9,9-dimethylacridan-10-yl group, a 10,11-dihydro-5H-dibenzo-[b,f]azepin-5-yl group, a 5H-dibenzo[b,f]azepin-5-yl group, a 5,11-dihydrodibenzo[b,e][1,4]oxazepin-5-yl group, a 10,11-dihydro-11-oxo-5H-dibenzo[b,e][1,4]diazepin-5-yl group, or a 11-hydro-10-methyl-11-oxo-5H-dibenzo[b,e][1,4]diazepin-5-yl group. A 10,11-dihydro-5H-dibenzo[b,f]azepin-5-yl group, or a 5,11-dihydrodibenzo[b,e][1,4]oxazepin-5-yl group is particularly preferable. Substituents of A and B are defined as above.

n is preferably an integer of 2 to 4, with 2 being particularly preferable.

The preferable "lower alkyl group with 1 to 4 carbon atoms" represented by $R_3$ or $R_4$ is a methyl group.

The preferable "halogen atom" represented by $R_3$ or $R_4$ is fluorine or chlorine.

The preferable "lower haloalkyl group with 1 to 4 carbon atoms" represented by $R_3$ or $R_4$ is a trifluoromethyl group.

Both $R_3$ and $R_4$ are most preferably hydrogen atoms.

Any salt can be used as "a pharmaceutically acceptable salt" as long as it forms a non-toxic salt with the compound of formula (I). Examples thereof include inorganic acid salts such as hydrochloride, hydrobromide, hydroiodide, sulfate, nitrate, phosphate, carbonate, bicarbonate, and perchlorate; organic acid salts such as formate, acetate, trifluoroacetate, propionate, oxalate, glycolate, succinate, lactate, maleate, hydroxymaleate, methylmaleate, fumarate, adipinate, tartrate, malate, citrate, benzoate, cinnamate, ascorbate, salicylate, 2-acetoxybenzoate, nicotinate, and isonicotinate; sulfonates such as methanesulfonate, ethanesulfonate, isethionate, benzensfulonate, p-toluenesulfonate, and naphthalenesulfonate; salts with acidic amino acid such as aspartic acid and glutamic acid; salts with alkali metals such as sodium and potassium; salts with organic bases such as trimethylamine, triethylamine, pyridine, picoline, dicylochexyl amine, and N,N'-dibenzyl-ethylenediamine; and salts with amino acid such as lysine and arginine.

More specifically, it is preferable that in formula (I) R represents an N-phenyl-N-(2-methylphenyl)amino group, a 10,11-dihydro-5H-dibenzo[b,f]azepin-5-yl group, a 10,11-dihydro-2-hydroxy-5H-dibenzo[b,f]azepin-5-yl group, a 10,11-dihydro-10-hydroxy-5H-dibenzo[b,f]azepin-5-yl group, or a 5,11-dihydrodibenzo[b,e]-[1,4]oxazepin-5-yl group; n is 2; and $R_3$ and $R_4$ represent a hydrogen atom.

The compounds of the present invention may be hydrates or solvates. The compounds of the present invention include their prodrug compounds and metabolites.

The compounds of the present invention have low toxicity and excellent MTP-inhibitory activity and can increase high density lipoprotein (HDL). The compounds are thus expected to be a new type of drug for treating or preventing hyperlipemia or arteriosclerotic diseases.

When the compounds of the present invention represented by formula (I) or their pharmaceutically acceptable salts are used as a pharmaceutical composition, they may be formulated into tablets, pills, powders, granules, suppositories, injections, liquid, capsules, troaches, aerosols, elixirs, suspensions, emulsions, and syrups, together with known pharmacologically acceptable carriers, excipients, diluents, extenders, distintegrators, stabilizers, preservatives, buffers, emulsifiers, aromatizers, colorants, edulcorants, viscosity increasing agents, flavors, solubilizers, or other additives such as water; plant oil; alcohols such as ethanol or benzyl alcohol, polyethylene glycol, glycerol triacetate gelatin, lactose; or carbohydrates such as starch, magnesium stearate, talc, lanolin, and vaseline. The composition may be administered orally, rectally, or parenterally.

The compounds of the present invention can be used as a drug for animals as well as humans.

The dose varies depending on the kinds and degree of diseases; the compounds to be administered; the route of administration; and the age, sex, and body weight of patients. For oral administration, the compound of formula (I) is preferably administered daily to an adult at a dose of 1 mg to 1000 mg, more preferably 50 mg to 800 mg.

The compounds of the present invention can be produced by the following methods. As a matter of course, the production methods are not to be restricted thereto.

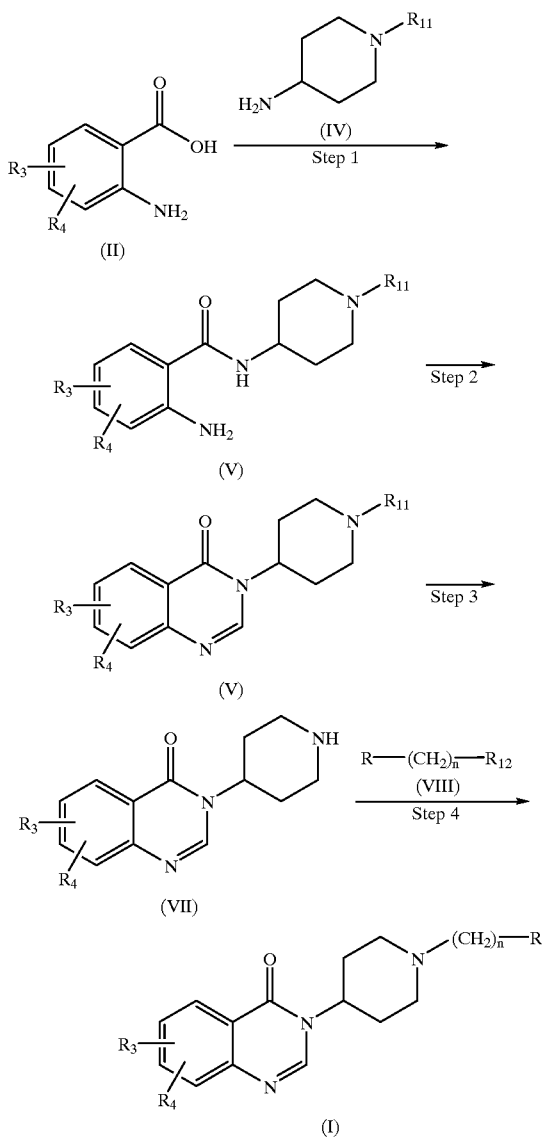

Step 1

Compound (V) (in the formula, $R_{11}$ represents an aminoprotective group such as benzyl, benzyloxycarbonyl, methoxycarbonyl, ethoxycarbonyl, or tert-butoxycarbonyl, and $R_3$ and $R_4$ are defined as above) can be synthesized by reacting compound (III) (in the formula, $R_3$ and $R_4$ are defined as above) with compound (IV) (in the formula, $R_{11}$ is defined as above) using a condensing agent such as 1-ethyl-3-(3-dimethylaminopropyl)carbodiimide hydrochloride (WSC HCl), dicyclohexylcarbodiimide (DCC), diphenylphosphoryl azide (DPPA), or carbonyl diimidazole (CDI), if necessary in the presence of an activating agent such as 1-hydroxybenzotriazole (HOBT), hydroxysuccinimide (HOSu), or N-hydroxy-5-norbornene-2,3-dicarboxylic acid imide (HONB), in an organic solvent such as dimethylformamide, dichloromethane, chloroform, acetonitrile, tetrahydrofuran, dimethylsulfoxide, carbon tetrachloride, or toluene, or a mixture of these solvents, under ice-cooling or with heating or at an appropriate temperature therebetween.

Step 2

Compound (VI) (in the formula, $R_3$, $R_4$, and $R_{11}$ are defined as above) can be synthesized by reacting compound (V) (in the formula, $R_3$, $R_4$, and $R_{11}$ are defined as above) in the presence of formic acid, triethyl orthoformate, etc., in an organic solvent such as methanol, ethanol, toluene, tetrahydrofuran, acetic acid, or dimethylformamide, or a mixture of these solvents, or in the absence of solvents, with heating.

Step 3

Compound (VII) (in the formula, $R_3$ and $R_4$ are defined as above) can be synthesized by treating compound (VI) (in the formula, $R_3$, $R_4$, and $R_{11}$ are defined as above) in the presence of acid such as hydrochloric acid, hydrobromic acid, trifluoroacetic acid, p-toluenesulfonic acid, methanesulfonic acid, hydrogen chloride-dioxane, hydrogen chloride-ether, hydrogen chloride-acetic acid, or hydrogen bromide-acetic acid, in an organic solvent such as dioxane, either, dichloromethane, tetrahydrofuran, methanol, ethanol, chloroform, benzene, toluene, ethyl acetate, or acetic acid, or water, or a mixture of these solvents, or in the absence of solvents. Alternatively, compound (VII) can be obtained by subjecting compound (VI) to catalytic reduction with hydrogen gas in the presence of a metal catalyst such as palladium-on-carbon, platinum oxide, Raney nickel, palladium black, or palladium hydroxide, in an organic solvent such as methanol, ethanol, dimethylformamide, ether, dioxane, tetrahydrofuran, acetic acid, or ethyl acetate, or water, or in a mixture of these solvents.

Step 4

Compound (I) (in the formula, R, $R_3$, $R_4$, and n are defined as above) can be synthesized by reacting compound (VII) (in the formula, $R_3$ and $R_4$ are defined as above) with compound (VII) (in the formula, $R_{12}$ represents a leaving group such as a halogen atom, a methanesulfonyloxy group, or a p-toluenesulfonyloxy group, and R and n are defined as above) using a base such as potassium carbonate, sodium acetate, sodium hydroxide, potassium hydroxide, sodium carbonate, sodium bicarbonate, triethylamine, or pyridine, if necessary in the presence of sodium iodide, etc., in an organic solvent such as methanol, ethanol, tetrahydrofuran, dioxane, dimethoxyethane, ether, diisopropylether, acetonitrile, dimethylformamide, toluene, ethyl acetate, chloroform, or dichloromethane, or water, or a mixture of these solvents, under cooling or with heating or at an appropriate temperature therebetween.

Compound (I) can also be synthesized by the following steps.

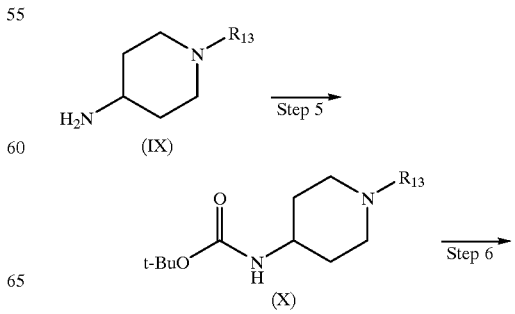

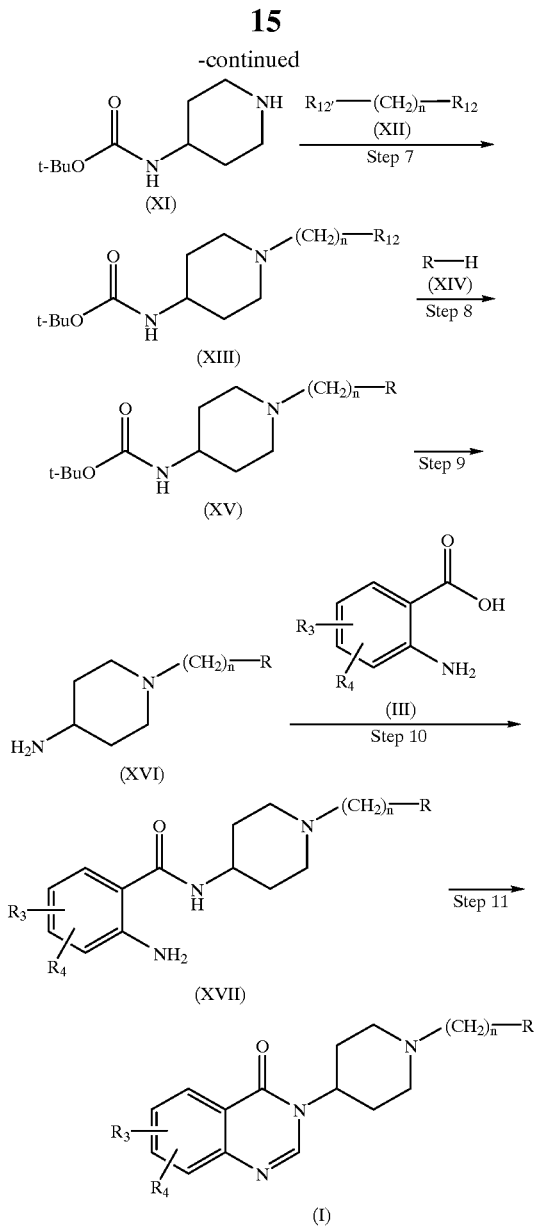

Step 5

Compound (X) (in the formula, $R_{13}$ represents an aminoprotective group such as benzyl or benzyloxycarbonyl) can be synthesized by reacting compound (IX) (in the formula, $R_{13}$ is defined as above) in the presence of pivalic anhydride, etc., in an organic solvent such as dichloromethane, chloroform, dioxane, tetrahydrofuran, toluene, dimethylformamide, or ether, or a mixture of these solvents, under cooling or with heating or at an appropriate temperature therebetween.

Step 6

Compound (XI) can be synthesized by subjecting compound (X) (in the formula, $R_{13}$ is defined as above) to catalytic reduction with hydrogen gas in the presence of a metal catalyst such as palladium-on-carbon, platinum oxide, Raney nickel, palladium black, or palladium hydroxide in an organic solvent such as methanol, ethanol, dimethylformamide, ether, dioxane, tetrahydrofuran, acetic acid, or ethyl acetate, or water, or a mixture of these solvents.

Step 7

Compound (XIII) (in the formula, $R_{12}$ and n are defined as above) can be synthesized by reacting compound (XI) with compound (XII) (in the formula, $R_{12}'$ represents a leaving group such as a halogen atom, a methanesulfonyloxy group, or a p-toluenesulfonyloxy group, and $R_{12}$ and n are defined as above) using a base such as potassium carbonate, sodium acetate, sodium hydroxide, potassium hydroxide, sodium carbonate, sodium bicarbonate, triethylamine, or pyridine, if necessary, in the presence of sodium iodide, etc., in an organic solvent such as methanol, ethanol, tetrahydrofuran, dioxane, dimethoxyethane, ether, diisopropylether, acetonitrile, dimethylformamide, toluene, ethyl acetate, chloroform, or dichloromethane, or water, or a mixture of these solvents, under cooling or with heating or at an appropriate temperature therebetween.

Step 8

Compound (XV) (in the formula, R and n are defined as above) can be synthesized by reacting compound (XIII) (in the formula, $R_{12}$ and n are defined as above) with compound (XIV) (in the formula, R is defined as above) in the presence of a base such as sodium hydride, sodium amide, or n-butyl lithium, in an organic solvent such as dimethylsulfoxide, dimethylformamide, tetrahydrofuran, or ether, or a mixture of these solvents, under cooling or with heating or at an appropriate temperature therebetween.

Step 9

Compound (XVI) (in the formula, R and n are defined as above) can be synthesized by treating compound (XV) (in the formula, R and n are defined as above) in the presence of acid such as trifluoroacetic acid, hydrochloric acid, hydrogen chloride-ether, hydrogen chloride-ethyl acetate, or hydrogen bromide-dioxane, in an organic solvent such as dichloromethane, chloroform, tetrahydrofuran, ethyl acetate, dioxane, ether, or toluene, or water, or a mixture of these solvents, under cooling or with heating or at an appropriate temperature therebetween.

Step 10

Compound (XVII) (in the formula, R, $R_3$, $R_4$, and n are defined as above) can be synthesized by reacting compound (XVI) (in the formula, R and n are defined as above) with compound (III) (in the formula, $R_3$ and $R_4$ are defined as above) using a condensing agent such as WSC.HCl, DCC, DPPA, or CDI, if necessary in the presence of an activating agent such as HOBT, HOSu, or HONB, in an organic solvent such as dimethylformamide, dichloromethane, chloroform, acetonitrile, tetrahydrofuran, dimethylsulfoxide, carbon tetrachloride, or toluene, or a mixture of these solvents, under cooling with ice or with heating or at an appropriate temperature therebetween.

Step 11

Compound (I) (in the formula, R, $R_3$, $R_4$, and n are defined as above) can be synthesized by treating compound (XVII) (in the formula, R, $R_3$, $R_4$, and n are defined as above) in the presence of formic acid, triethyl orthoformate, etc., in an organic solvent such as methanol, ethanol, toluene, tetrahydrofuran, acetic acid, or dimethylformamide, or a mixture of these solvents, or in the absence of solvents, with heating.

Compound (I) can also be synthesized by the following method.

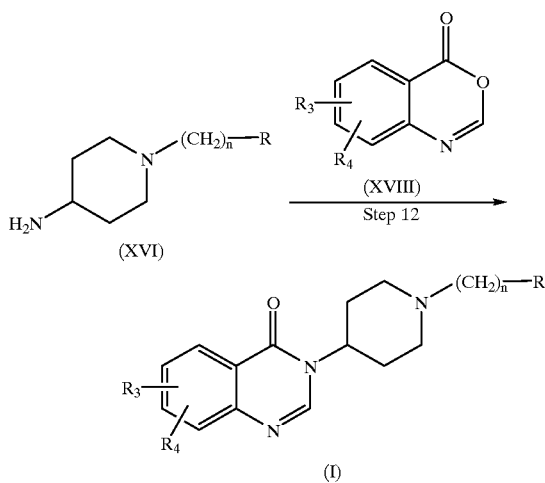

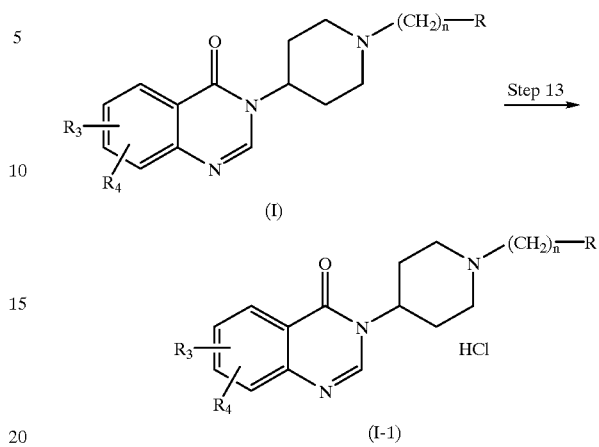

Step 12

Compound (I) (in the formula, R, $R_3$, $R_4$, and n are defined as above) can be synthesized by reacting compound (XVI) (in the formula, R and n are defined as above) with compound (XVIII) (in the formula, $R_3$ and $R_4$ are defined as above) in the presence of triethyl orthoformate, etc., in an organic solvent such as toluene, xylene, or benzene, or a mixture of these solvents, with heating.

Compound (I) having a hydroxyl or amino group as a substituent can be produced by synthesizing the corresponding compound with the protective group attached using the above-described steps and eliminating the protective group by the usual method.

Compound (I) obtained in the above steps 4, 11, or 12 can be converted into a salt using an ordinary method after synthesis of compound (I). For example, hydrochloride can be synthesized using the following Step 13.

Step 13

Compound (I-1) (in the formula, R, $R_3$, $R_4$, and n are defined as above) can be synthesized by treating compound (I) (in the formula, R, $R_3$, $R_4$, and n are defined as above) in the presence of hydrogen chloride-ether, hydrogen chloride-ethyl acetate, hydrogen chloride-dioxane, etc., in an organic solvent such as chloroform, dichloromethane, ethyl acetate, ethanol, methanol, acetone, toluene, tetrahydrofuran, or dioxane, or a mixture of these solvents, under cooling or with heating or at an appropriate temperature therebetween.

Compound (VIII) used in the above Step 4 can be synthesized through the following steps.

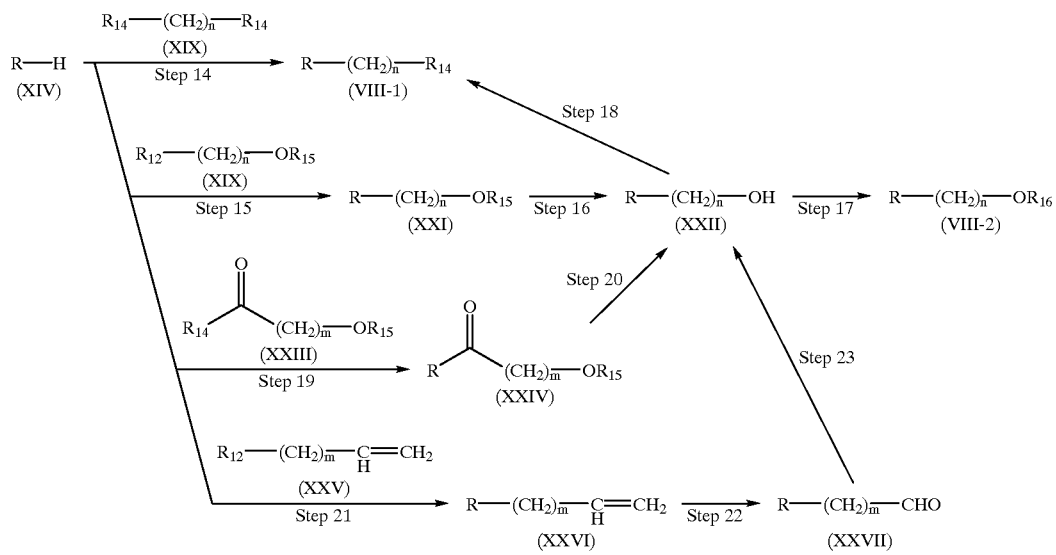

Step 14

Compound (VIII-1) (in the formula, $R_{14}$ represents a halogen atom, and n is defined as above) can be synthesized by reacting compound (XIX) (in the formula, $R_{14}$ and n are defined as above) with compound (XIX) (in the formula, R is defined as above) in the presence of a base such as diisopropylethylamine, in an organic solvent such as toluene or xylene, or a mixture of these solvents, or in the absence of solvents with heating. Compounds such as N-(3-bromopropyl)-10,11-dihydro-5H-dibenzo[b,f]azepine can be synthesized by subjecting synthesized compounds such as N-(3-bromopropyl)-5H-benzo[b,f]azepine to an ordinary reduction reaction.

Compound (VIII) can also be synthesized using the following steps.

Step 15

Compound (XXI) (in the formula, $R_{15}$ represents a hydroxyl-protective group such as acetyl, benzyl, or tert-butyldimethylsilyl, and R and n are defined as above) can be synthesized by reacting compound (XIV) (in the formula R is defined as above) with compound (XX) (in the formula, $R_{12}$, $R_{15}$, and n are defined as above) in the presence of a base such as sodium hydride, sodium amide, or n-butyl lithium, in an organic solvent such as dimethylsulfoxide, dimethylformamide, or tetrahydrofuran, or a mixture of these solvents under cooling or with heating or at an appropriate temperature therebetween.

Step 16

In this step, compound (XXII) (in the formula, R and n are defined as above) is synthesized by eliminating a hydroxyl-protective group, $R_{15}$, using a common deprotecting reaction. For example, when the hydroxyl-protective group is acetyl or benzyl, compound (XXI) (in the formula, R, $R_{15}$, and n are defined as above) is treated in the presence of a base such as sodium hydroxide, potassium hydroxide, potassium carbonate, or sodium carbonate, in an organic solvent such as methanol, ethanol, tetrahydrofuran, dioxane, dimethylformamide, or acetonitrile, or water, or a mixture of these solvents, under cooling or with heating or at an appropriate temperature therebetween. When the protective group is a tert-butyldimethylsilyl group, compound (XXI) is treated in the presence of tetrabutylammonium fluoride, etc., in an organic solvent such as tetrahydrofuran, under cooling or with heating or at an appropriate temperature therebetween.

Step 17

Compound (VIII-2) (in the formula, $R_{16}$ represents methanesulfonyl or p-toluenesulfonyl, and R and n are defined as above) can be synthesized by reacting compound (XXII) (in the formula, R and n are defined as above) with a sulfonylating agent such as methanesulfonyl chloride or p-toluenesulfonyl chloride, in the presence of a base such as triethylamine or pyridine, in an organic solvent such as dichloromethane, chloroform, or toluene, or a mixture of these solvents, under cooling or with heating or at an appropriate temperature therebetween.

Compound (VIII-1) can also be synthesized from compound (XXII).

Step 18

Compound (VIII-1) (in the formula, R, $R_{14}$, and n are defined as above) can be synthesized by treating compound (XXII) (in the formula, R and n are defined as above) in the presence of a halogenating agent such as carbon tetrabromide, carbon tetrachloride, or N-bromosuccinimide together with an auxiliary agent such as triphenyl phosphine, in an organic solvent such as dichloromethane or chloroform or a mixture of these solvents under cooling or with heating or at an appropriate temperature therebetween. Alternatively, the compound can be produced by reacting in the presence of a halogenating agent such as thionyl chloride or phosphorus tribromide, in an organic solvent such as chloroform or a mixture of the solvents under cooling or with heating or at an appropriate temperature therebetween. In certain cases, the compound can be synthesized by reacting in the same manner as in Step 17 above.

Compound (XXII) can also be synthesized using the following step.

Step 19

Compound (XXIV) (in the formula, m represents 0 or an integer of 1 to 3, which is smaller than n by 1 (for example, when n of the final compound is 2, m is 1), and R and $R_{15}$ are defined as above) can be synthesized by reacting compound (XIV) (in the formula, R is defined as above) with compound (XXIII) (in the formula, $R_{14}$, $R_{15}$, and m are defined as above) in the presence of a base such as triethylamine or pyridine, in an organic solvent such as chloroform, dichloromethane, toluene, tetrahydrofuran, ethyl acetate, or dioxane, or a mixture of these solvents, under cooling or with heating or at an appropriate temperature therebetween.

Step 20

Compound (XXII) (in the formula, R and n are defined as above) can be synthesized by reacting compound (XXIV) (in the formula, R, $R_{15}$, and m are defined as above) in the presence of a reducing agent such as lithium aluminium hydride in an organic solvent such as ether or tetrahydrofuran, or a mixture of these solvents, under cooling or with heating or at an appropriate temperature therebetween.

Compound (XXII) can also be synthesized by the following steps.

Step 21

Compound (XXVI) (in the formula, R and m are defined as above) can be synthesized by reacting compound (XIV) (in the formula, R is defined as above) with compound (XXV) (in the formula, $R_{12}$ and m are defined as above) in the presence of a base such as sodium hydride in an organic solvent such as dimethylformamide or dimethylsulfoxide, or a mixture of these solvents, under cooling or with heating or at an appropriate temperature therebetween.

Step 22

Compound (XXVII) (in the formula, R and m are defined as above) can be synthesized by reacting compound (XXVI) (in the formula, R and m are defined as above) in the presence of an oxidizing agent such as ozone in an organic solvent such as tetrahydrofuran, dichloromethane, chloroform, ether, ethyl acetate, or methanol, or a mixture of these solvents, under cooling or with heating or at an appropriate temperature therebetween, then treating in the presence of a reducing agent such as dimethylthioether, zinc-acetic acid, sodium iodide, or trimethyl phosphite, in an organic solvent such as tetrahydrofuran, dichloromethane, chloroform, ether, ethyl acetate, or methanol, or a mixture of these solvents, under cooling or with heating or at an appropriate temperature therebetween. Alternatively, the desired compound can be obtained by reacting compound (XXVI) in the presence of a mixture of an oxidizing agent such as sodium periodate and osmium tetroxide, in an organic solvent such as tetrahydrofuran, dichloromethane, chloroform, ether, ethyl acetate, or methanol, or water, or a mixture of these solvents, under cooling or with heating or at an appropriate temperature therebetween.

Step 23

Compound (XXII) (in the formula, R and n are defined as above) can be synthesized by reacting compound (XXVII) (in the formula, R and m are defined as above) in the presence of a reducing agent such as sodium borohydride, sodium cyanoborohydride, lithium aluminium hydride, diisobutyl aluminium hydride, or lithium borohydride, in an organic solvent such as methanol, ether, tetrahydrofuran, toluene, dichloromethane, or chloroform, or a mixture of these solvents, under cooling or with heating or at an appropriate temperature therebetween.

For compound (XXII), in which at least one of $R_1$ or $R_2$ is a lower alkyl group such as a methyl group, the desired compound can be synthesized by the following steps. As an example, the method of producing the compound in which $R_2$ is a lower alkyl group will be described.

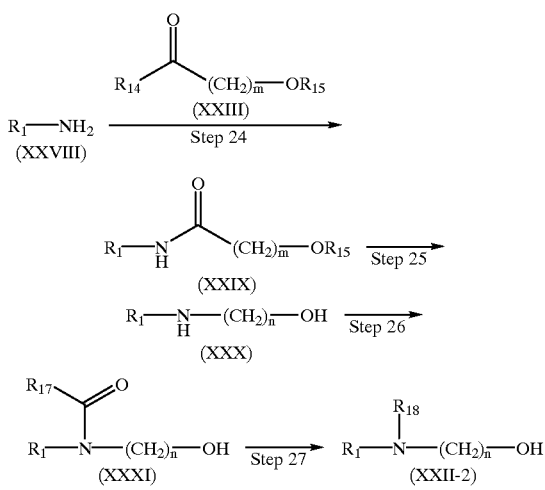

Step 24

Compound (XXIX) (in the formula, $R_1$, $R_{15}$, and m are defined as above) can be synthesized by reacting compound (XXVIII) (in the formula, $R_1$ is defined as above) with compound (XXIII) (in the formula, $R_{14}$, $R_{15}$, and m are defined as above) in the presence of a base such as triethylamine or pyridine, in an organic solvent such as dichloromethane, chloroform, toluene, tetrahydrofuran, ethyl acetate, or dioxane, or a mixture of these solvents, under cooling or with heating or at an appropriate temperature therebetween.

Step 25

Compound (XXX) (in the formula, $R_1$ and n are defined as above) can be synthesized by reacting compound (XXIX) (in the formula, $R_1$, $R_{15}$, and m are defined as above) in the presence of a reducing agent such as lithium aluminium hydride or borane-tetrahydrofuran complex, in an organic solvent such as tetrahydrofuran, ether, or toluene, or a mixture of these solvents, under cooling or with heating or at an appropriate temperature therebetween.

Step 26

Compound (XXXI) (in the formula, $R_{17}$ represents a hydrogen atom or a lower alkyl group such as methyl, and $R_1$ and n are defined as above) can be synthesized by reacting compound (XXX) (in the formula, $R_1$ and n are defined as above) and the corresponding carboxylic acid ethyl ester such as ethyl formate or ethyl acetate, or acid hydride such as acetyl chloride in an organic solvent such as dichloromethane or chloroform or a mixture of these solvents, or in the absence of solvents, under cooling or with heating or at an appropriate temperature therebetween.

Step 27

Compound (XXII-2) (in the formula, $R_{18}$ represents a lower alkyl group such as methyl, and $R_1$ and n are defined as above) can be synthesized by treating compound (XXXI) (in the formula, $R_1$, $R_{17}$, and n are defined as above) in the presence of a reducing agent such as lithium aluminium hydride or borane-tetrahydrofuran complex, in an organic solvent such as tetrahydrofuran, under cooling or with heating or at an appropriate temperature therebetween.

Compound (XXI), in which at least one of $R_1$ or $R_2$ is benzyl or benzoyl, can be synthesized by the following steps. As an example, the method of producing the desired compound where $R_2$ is benzyl or benzoyl will be described.

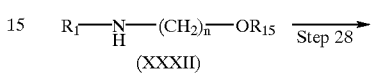

Step 28

Compound (XXI-2) (in the formula, $R_{21}$ represents benzyl or benzoyl, and $R_1$, $R_{15}$, and n are defined as above) can be synthesized by reacting compound (XXXII) (in the formula, $R_1$, $R_{15}$, and n are defined as above) with a corresponding halide compound such as benzyl bromide or benzyl chloride in the presence of a base such as sodium hydride, potassium carbonate, or triethylamine, in an organic solvent such as dimethylformamide, dichloromethane, dimethylsulfoxide, tetrahydrofuran, toluene, or ether, or a mixture of these solvents, under cooling or with heating or at an appropriate temperature therebetween.

Compound (I) thus obtained can be isolated and purified using known isolation and purification methods such as condensation, condensation under reduced pressure, extraction with a solvent, crystallization, recrystallization, and chromatography.

BEST MODE FOR IMPLEMENTING THE INVENTION

The present invention will be described in detail below with reference to production examples, working examples, and test examples. However, this invention is not to be construed to be restricted to those examples.

PRODUCTION EXAMPLE 1

Synthesis of 10,11-dihydro-5H-dibenzo[b,e][1,4] diazepin-1-one

A mixture of 2-chlorobenzoic acid (15.7 g), 1,2-phenylenediamine (10.8 g), copper powder (6.3 g), and chlorobenzene (300 ml) was heated for 8 hours under refluxing in a stream of argon air. After filtration while hot, the mixture was allowed to cool to room temperature. After cooling, the mixture was concentrated under reduced pressure to about ⅓ volume, and the solid allowed to precipitate gradually. The precipitated solid was collected by filtration, washed with chlorobenzene and methanol, and dried to obtain the desired compound (5.89 g; yield, 28%) as a dark yellowish green solid.

PRODUCTION EXAMPLE 2

Synthesis of 2-methyl-N-phenylaniline

1) A mixture of 2-methylacetanilide (4.5 g), iodobenzene (6.8 ml), potassium carbonate (8.3 g), and copper iodide (574 mg) was stirred overnight at 150° C. After the mixture was allowed to cool, water and ethyl acetate were added thereto, and the mixture was further stirred. The mixture was then filtered with celite. Filtrate was collected, and an aqueous phase was extracted with ethyl acetate. The extract was washed with water and saturated brine, and dried over sodium sulfate. The resulting solution was filtered, and the filtrate was concentrated under reduced pressure. The residue was purified by silica gel column chromatography (developing solvent, ethyl acetate:hexane=1:2.5) to obtain 2-methyl-N-phenylacetanilide (4.96 g; yield, 73%) as a light brown oil.

2) The compound (4.51 g) obtained in 1) was dissolved in tetrahydrofuran (80 ml), and potassium tert-butoxide (132.0 ml) and water (0.72 ml) were added thereto. The mixture was stirred for 1.5 hours at 80° C. After the mixture was allowed to cool, water was added thereto under ice-cooling. After tetrahydrofuran was removed by evaporation, the resulting residue was extracted with ethyl acetate, washed with water and saturated brine, and dried over sodium sulfate. The resulting product was filtered, and the filtrate was concentrated under reduced pressure to obtain the desired compound (3.44 g; yield, 94%) as an oil.

PRODUCTION EXAMPLE 3

Synthesis of N-(2-thienyl)aniline

1) A mixture of acetanilide (6.0 g), 2-iodothiophene (18.6 g), copper iodide (864 mg), and potassium carbonate (12.2 g) was heated for 2 hours at 150° C. After the mixture was allowed to cool, water and ethyl acetate were added thereto. The resulting mixture was stirred, then filtered with celite. The aqueous phase was extracted. The organic phase was washed with water and saturated brine, and dried over sodium sulfate. The resulting solution was filtered, and the filtrate was concentrated under reduced pressure. The residue was purified by silica gel column chromatography (developing solvent, ethyl acetate:hexane=1:5) to obtain N-(2-thienyl)acetanilide (1.77 g; yield, 18%) as a light brown solid.

2) Potassium hydroxide (646 ml) and water (6 ml) were added to an ethanol (16 ml) solution of the compound (1.77 g) obtained in 1), and the mixture was heated at 80° C. for 3 hours. After the mixture was allowed to cool, it was extracted with ethyl acetate, washed with water and saturated brine, and dried over sodium sulfate. The resulting solution was filtered, and the filtrate was concentrated under reduced pressure. The resulting residue was purified by silica gel column chromatography (developing solvent, ethyl acetate:hexane=1:5) to obtain the desired compound (701 mg; yield, 49%) as a purple oil.

PRODUCTION EXAMPLE 4

Synthesis of N-(3-pyridyl)aniline

1) Acetanilide (6.0 g) and 3-bromopyridine (14.1 g) were used to make a reaction in the same manner as in 1) of Production Example 2. The subsequent purification by silica gel column chromatography (developing solvent, ethyl acetate:hexane:=1:1 to 2:1) produced N-(3-pyridyl)-acetanilide (9.52 g, quantitative) as a pale red solid.

2) A mixture of the compound (13.4 g) obtained in 1) and 2N hydrochloric acid (130 ml) was heated at 100° C. for 4 hours. After the mixture was allowed to cool, it was made alkaline with 4N sodium hydroxide, extracted with ethyl acetate, and washed with saturated brine. The resulting solution was dried over sodium sulfate and filtered. The filtrate was concentrated under reduced pressure to obtain the desired compound (10.3 g; yield, 96%) as a pale pink solid.

PRODUCTION EXAMPLE 5

Synthesis of N-phenyl-2-propylaniline

1) Acetic anhydride (7.5 ml) was added to a toluene (100 ml) solution of 2-propylaniline, and the mixture was stirred at room temperature for 2 hours. Crystals thus precipitated were collected by filtration and washed with hexane. The filtrate was concentrated under reduced pressure. After hexane was added thereto, trituration was conducted. The deposited crystals were collected by filtration and washed with hexane. By the above crystallization steps, 2-propylacetanilide (13.0 g; yield, 96%) was obtained as white crystals.

2) Using the compound (5.3 g) obtained in 1) and iodobenzene (12.4 ml), a reaction was made in the same manner as in 1) of Production Example 2. The subsequent purification by silica gel column chromatography (developing solvent, ethyl acetate:hexane=1:4) produced N-phenyl-2-propylacetanilide (3.15 g; yield, 41%) as an amber solid.

3) Using the compound (3.15 g) obtained in 2), a reaction was made in the same manner as in 2) of Production Example 4 to obtain the desired compound (2.63 g, quantitative) as a brown oil.

PRODUCTION EXAMPLE 6

Synthesis of N-(3-thienyl)-aniline

1) Using acetanilide (6.0 g) and 3-bromothiophene (14.5 g), a reaction was made in the same manner as in 1) of Production Example 2. The subsequent purification by silica gel column chromatography (developing solvent, ethyl acetate:hexane=1:4) produced N-(3-thienyl)acetanilide (2.43 g; yield, 25%) as a pale brown solid.

2) Using the compound (2.4 g) obtained in 1), a reaction was made in the same manner as in 2) of Production Example 3. The subsequent purification by silica gel column chromatography (developing solvent, ethyl acetate:hexane= 1:5) produced the desired compound (1.64 g; yield, 85%) as a brown oil.

PRODUCTION EXAMPLE 7

Synthesis of N-(5-pyrimidinyl)aniline

1) Using acetanilide (8.25 g) and 5-bromopyrimidine, a reaction was made in the same manner as in 1) of Production Example 2. The subsequent purification by silica gel column chromatography (developing solvent, ethyl acetate:hexane= 1:1 to 3:1) produced N-(5-pyrimidinyl)acetanilide (7.98 g; yield, 61%) as a pale yellow oil.

2) Using the compound (6.8 g) obtained in 1), a reaction was made in the same manner as in 2) of Production Example 3 to obtain the desired compound (4.88 g; yield, 89%) as a pale yellow solid.

PRODUCTION EXAMPLE 8

Synthesis of 3-methoxy-N-phenylaniline

1) Using acetanilide (3.7 g) and 3-iodoanisole, a reaction was made in the same manner as is 1) of Production Example 2. The subsequent purification by silica gel column chromatography (developing solvent, ethyl acetate:hexane=1:3 to 1:2) produced 3-methoxy-N-phenylacetanilide (4.44 g; yield, 67%) as a pale brown oil.

2) Using the compound (4.4 g) obtained in 1), a reaction was made in the same manner as in 2) of Production Example 3 to obtain the desired compound (3.0 g; yield, 83%) as a pale brown solid.

PRODUCTION EXAMPLE 9

Synthesis of 2-isopropyl-N-phenylaniline

1) Using 2-isopropylaniline (10.0 g, a reaction was made in the same manner as in 1) of Production Example 5 to obtain 2-isopropylacetanilide (13.2 g, quantitative) as a pale brown solid.

2) Using the compound (5.32 g) obtained in 1) and iodobenzene (5.04 ml), a reaction was made in the same manner as in 1) of Production Example 2. The subsequent purification by silica gel column chromatography (developing solvent, ethyl acetate:hexane=2:5) produced 2-isopropyl-N-phenylacetanilide (3.8 g; yield, 50%) as a pale pink solid.

3) Using the compound (3.8 g) obtained in 2), a reaction was made in the same manner as in 2) of Production Example 2 to obtain the desired compound (3.15 g; yield, 99%) as a pale brown oil.

PRODUCTION EXAMPLE 10

Synthesis of 2-butyl-N-phenylaniline

1) Using 2-butylaniline (10.0 g), a reaction was made in the same manner as in 1) of Production Example 5 to obtain 2-butyl acetanilide (12.0 g; yield, 94%) as a white solid.

2) Using the compound (5.7 g) obtained in 1) and iodobenzene (6.8 ml), a reaction was made in the same manner as in 1) of Production Example 2. The subsequent purification by silica gel column chromatography (developing solvent, ethyl acetate:hexane=1:5) produced 2-butyl-N-phenylacetanilide (3.65 g; yield, 46%) as an amber oil.

3) Using the compound (3.65 g) obtained in 2), a reaction was made in the same manner as in 2) of Production Example 4 to obtain the desired compound (3.07 g, quantitative) as a brown oil.

PRODUCTION EXAMPLE 11

Synthesis of 2-ethyl-N-phenylaniline

1) Using 2-ethylacetanilide (4.9 g) and iodobenzene (12.4 ml), a reaction as made in the same manner as in 1) of Production Example 2. The subsequent purification by silica gel column chromatography (developing solvent, ethyl acetate:hexane=1:3) produced 2-ethyl-N-phenylacetanilide (4.0 g; yield, 56%) as a brown oil.

2) Using the compound(4.0 g) obtained in 1), a reaction was made in the same manner as in 2) of Production Example 4. The subsequent purification by silica gel column chromatography (developing solvent, ethyl acetate:hexane=1:35) produced the desired compound (3.3 g; yield, 95%) as a brown oil.

PRODUCTION EXAMPLE 12

Synthesis of 1,1,1'-triphenyldimethylamine hydrochloride

A small amount of p-toluenesulfonic acid monohydrate was added to a toluene (100 ml) solution of benzophenone (18.2 g) and benzylamine (11.0 ml). Water was removed with Deanstark. After 11 hours, the reaction solution was concentrated under reduced pressure to obtain an oil product. Sodium borohydride (3.5 g) was added to a methanol (250 ml) solution of the thus-obtained oil under ice-cooling, and the mixture was stirred overnight at room temperature. After the reaction mixture was concentrated under reduced pressure, water, ethyl acetate, and 2 N hydrochloric acid (100 ml) were added thereto to precipitate crystals. The resulting crystals were collected by filtration and washed with ethyl acetate and water to obtain the desired compound (14.4 g; yield, 46%) as white crystals.

PRODUCTION EXAMPLE 13

Synthesis of N-benzyl-N-(2-tert-butyldimethylsilyloxyethyl)amine

An N,N-dimethylformamide (40 ml) solution of 2-benzyl-aminoethanol (3 g), tert-butyldimethylsilyl chloride (3.6 g), and imidazole (3.4 g) was stirred at room temperature for 1 hour in a stream of argon air. Water (300 ml) was added to the reaction solution, and the solution was extracted with ethyl acetate. The organic phase was washed with water and saturated brine, dried over sodium sulfate, and filtered. The filtrate was concentrated under reduced pressure, and the resulting residue was dried to obtain the desired compound (5.3 g, quantitative) as a pale yellow oil.

PRODUCTION EXAMPLE 14

Synthesis of 4-chloro-N-pyridyl-2-ylaniline

1) A mixture of 4-chloroacetanilide (5.1 g), 2-bromopyridine (9.5 g), potassium carbonate (8.3 g), and copper iodide (570 mg) was stirred overnight at 150° C. After the mixture was allowed to cool, water and ethyl acetate were added thereto. The resulting solution was filtered with celite, and the organic phase was separated. Ethyl acetate was added to the aqueous phase to conduct extraction, and the extract was combined with the organic phase obtained above. The combined extract was washed with water and saturated brine, dried over sodium sulfate, and filtered. The filtrate was concentrated under reduced pressure. The subsequent purification by silica gel column chromatography (developing solvent, ethyl acetate:hexane=1:1) produced 4-chloro-N-pyridyl-2-ylacetanilide (7.3 g, crude product) as a yellow oil.

2) 2N Hydrochloric acid (63 ml) was added to the compound (7.3 g) obtained in 1), and the solution was heated under reflux while stirring. After 2.5 hours, 4 N aqueous sodium hydroxide was added thereto to neutralize the solution, followed by extraction with ethyl acetate. The organic phase was washed with water and saturated brine, dried over sodium sulfate, and filtered. The filtrate was concentrated and ethyl acetate was added to the residue. The solution was recrystallized from hexane to obtain the desired compound (4.0 g; yield, 65%) as pale yellow crystals.

PRODUCTION EXAMPLE 15

Synthesis of 5,11-dihydrodibenzo[b,e][1,4]oxazepine

1) An aqueous solution (20 ml) of potassium hydroxide (3.2 g) was added dropwise to an ethanol (40 ml) solution of 2-bromobenzyl bromide (10.0 g) and 2-nitrophenol (6.7 g). The resulting reaction mixture was heated under reflux for 3 hours, then allowed to cool under stirring at room temperature. The thus-obtained crystals were collected by filtration, washed with water, and dried at 60° C. under reduced pressure to obtain o-bromobenzyl-o-nitrophenylether (11.0 g; yield, 89%) as pale yellow crystals.

2) Isopropanol (160 ml) was added to the compound (11.0 g) obtained in 1) to dissolve the compound at 60° C. Hydrochloric acid (7.1 ml) was added thereto, and reduced iron (30 mg) was further added thereto in six divided portions. The resulting reaction mixture was heated for 8 hours under reflux, then filtered with celite. The filtrate was washed with isopropanol and concentrated under reduced pressure. A 2 N sodium hydroxide aqueous solution was added to the thus-obtained residue for neutralization, and the solution was extracted with ethyl acetate. The organic phase was washed with water and saturated brine, dried over sodium sulfate, and filtered. The filtrate was concentrated under reduced pressure, and the resulting residue was purified by silica gel column chromatography (developing solvent, ethyl acetate:hexane=1:6) to obtain o-(o-bromobenzyloxy)aniline (9.9 g, quantitative) as a brown oil.

3) A formic acid (60 ml) solution was added to the compound (9.9 g) obtained in 2) and sodium formate (4.9 g). The resulting reaction mixture was heated for 3 hours under reflux with stirring, allowed to cool to room temperature, and poured into water (150 ml) under ice-cooling. After further stirring, precipitated crystals were collected by filtration and washed with water. The resulting crystals were dried under reduced pressure at 60° C. to obtain o-(o-bromobenzyloxy)formanilide (9.6 g; yield, 88%) as a beige solid.

4) An N,N-dimethylformamide (110 ml) solution of the compound (9.6 g) obtained in 3), potassium carbonate (8.7 g), and copper powder (710 mg) was stirred at 150° C. in a stream of argon air. After 3.5 hours, the mixture was filtered while it was still hot. The filtrate was washed with ethanol and concentrated under reduced pressure. The thus-obtained residue was dissolved in ethanol (80 ml) and treated with activated charcoal. After filtration, the filtrate was concentrated and dissolved in ethanol (80 ml). A 25% sodium hydroxide aqueous (17 ml) solution was added to the solution and heated under reflux for 1 hour with stirring. After the resulting reaction solution was concentrated under reduced pressure, water was added thereto, and the solution was extracted with ethyl acetate. The organic phase was washed with water and saturated brine, dried over sodium sulfate, and filtered. The filtrate was concentrated under reduced pressure. The thus-obtained residue was purified by silica gel column chromatography (developing solvent, ethyl acetate:hexane=1:10) and recrystallized from hexane to obtain the desired compound (4.4 g; yield, 71%) as a white solid.

PRODUCTION EXAMPLE 16

Synthesis of 3,5-dimethyl-N-(2-pyridyl)aniline

1) A toluene (50 ml) solution of acetic anhydride (7.78 ml) was added to a toluene (100 ml) solution of 3,4-dimethylaniline (10 g) under ice-cooling. The resulting solution was stirred at room temperature for 2 hours, concentrated under reduced pressure, and dried to obtain 3,5-dimethylacetanilide (13.3 g; yield, 99%) as a pale brown solid.

2) Using the compound (4.9 g) obtained in 1) and 2-bromopyridine (9.5 g), a reaction was made in the same manner as in 1) of Production Example 14. The subsequent purification by silica gel column chromatography (developing solvent, ethyl acetate:hexane=1:1) produced 3,5-dimethyl-N-(2-pyridyl)acetanilide (7.2 g) as a pale yellow oil.

3) Using the compound (5.7 g) obtained in 2), a reaction was made in the same manner as in 2) of Production Example 14. The subsequent purification by silica gel column chromatography (developing solvent, ethyl acetate:hexane=1:3) produced the desired compound (4.4 g; yield, 75%) as a pale brown solid.

PRODUCTION EXAMPLE 17

Synthesis of 4-fluoro-N-(2-pyridyl)aniline

1) Triethylamine (31 ml) and acetyl chloride (15 ml) were added dropwise to a chloroform (100 ml) solution of 4-fluoroaniline (22.3 g) in this order under ice-cooling. The reaction mixture was stirred at room temperature for 2 hours and concentrated under reduced pressure. The thus-obtained solid was washed with water, collected by filtration, and recrystallized from ethanol-water to obtain colorless crystals of 4-fluoroacetanilide (25.5 g; yield, 83%).

2) Using the compound (10.7 g) obtained in 1) and 2-bromopyridine (22.2 g), a reaction was made in the same manner as in 1) of Production Example 14. The subsequent purification by silica gel column chromatography (developing solvent, ethyl acetate:hexane=1:2 to 1:1) produced oily 4-fluoro-N-(2-pyridyl)acetanilide (14.2 g, crude product).

3) Using the compound (14.2 g) obtained in 2), a reaction was made in the same manner as in 2) of Production Example 14. The product thus obtained was recrystallized from ethanol-water then from ethyl acetate-hexane to obtain the desired compound (8.9 g; yield, 77%).

PRODUCTION EXAMPLE 18

Synthesis of 4-methyl-N-(2-pyridyl)aniline

1) Using 4-methyl-acetanilide (4.48 g) and 2-bromopyridine (9.50 g), a reaction was made in the same manner as in 1) of Production Example 14. The subsequent purification by silica gel column chromatography (developing solvent, ethyl acetate:hexane=2:3) produced 4-methyl-N-(2-pyridyl)acetanilide (6.93 g, crude product) as a yellow oil.

2) Using the compound (6.91 g) obtained in 1), a reaction was made in the same manner as in 2) of Production Example 14. The subsequent purification by silica gel column chromatography (developing solvent, ethyl acetate:hexane:chlorform=1:4:1) produced the desired compound (4.69 g; yield, 83%) as a white solid.

PRODUCTION EXAMPLE 19

Synthesis of 4-methoxy-N-(2-pyridyl)aniline

1) Using 4-methoxyacetanilide (5.0 g) and 2-bromopyridine (9.5 g), a reaction was made in the same manner as in 1) of Production Example 14. The subsequent purification by silica gel column chromatography (developing solvent, ethyl acetate:hexane=1:1) produced 4-methoxy-N-(2-pyridyl)acetanilide (7.3 g, crude product) as a brown oil.

2) Using the compound (7.3 g) obtained in 1), a reaction was made in the same manner as in 2) of Production Example 14. The thus-obtained residue was dissolved in ethyl acetate and recrystallized from hexane to obtain the desired compound (3.0 g; yield, 50%) as pale yellow crystals.

PRODUCTION EXAMPLE 20

Synthesis of 3,4-dichloro-N-(2-pyridyl)aniline

1) Using 3,4-dichloroaniline (10.00 g), a reaction was made in the same manner as in 1) of Production Example 16 to obtain 3,4-dichloroacetanilide (12.62 g, quantitative) as a brown solid.

2) Using the compound (9.50 g) obtained in 1) and 2-bromopyridine (6.12 g), a reaction was made in the same manner as in 1) of Production Example 14. The subsequent purification by silica gel column chromatography (developing solvent, ethyl acetate:hexane=2:3) produced 3,4-dichloro-N-(2-pyridyl)acetanilide (7.90 g, crude product) as a brown oil.

3) Using the compound (7.90 g) obtained in 2), a reaction was made in the same manner as in 2) of Production Example 14. The subsequent purification by silica gel column chromatography (developing solvent, ethyl acetate:hexane:chloroform=1:7:1) produced the desired compound (2.35 g; yield, 35%) as a white solid.

PRODUCTION EXAMPLE 21

Synthesis of N-(6-methyl-2-pyridyl)aniline

1) Using acetanilide (9.16 g) and 2-chloro-6-methylpyridine (17.3 g), a reaction was made in the same manner as in 1) of Production Example 14. The subsequent purification by silica gel chromatography (developing solvent, ethyl acetate:hexane=1:1, ethyl acetate) produced N-(6-methyl-2-pyridyl)acetanilide (1.07 g; yield, 7%) as a pale brown oil.

2) Using the compound (1.3 g) obtained in 1), a reaction was made in the same manner as in 2) of Production Example 14 to obtain the desired compound (956 mg; yield, 90%) as a brown oil.

PRODUCTION EXAMPLE 22

Synthesis of 3-trifluoromethyl-N-(2-pyridyl)aniline

1) Using 3-trifluoromethyl-acetanilide (6.1 g) and 2-bromopyridine, a reaction was made in the same manner as in 1) of Production Example 14. The subsequent purification by silica gel column chromatography (developing solvent, ethyl acetate:hexane=1:1) produced 3-trifluoromethyl-N-(2-pyridyl)acetanilide (4.20 g; yield, 50%) as a pale brown oil.

2) Using the compound (4.2 g) obtained in 1), a reaction was made in the same manner as in 2) of Production Example 14. The subsequent purification by silica gel column chromatography (developing solvent, ethyl acetate:hexane=1:3) produced the desired compound (2.64 g; yield, 74%) as a white solid.

PRODUCTION EXAMPLE 23

Synthesis of 3-fluoro-N-(2-pyridyl)aniline

1) Using 3-fluoro-acetanilide (4.6 g) and 2-bromopyridine (9.5 g), a reaction was made in the same manner as in 1) of Production Example 14. The subsequent purification by silica gel column chromatography (developing solvent, ethyl acetate:hexane=1:1) produced 3-fluoro-N-(2-pyridyl)acetanilide (6.9 g, crude product as a yellow oil.

2) Using the compound (6.9 g) obtained in 1), a reaction was made in the same manner as in 2) of Production Example 14. The subsequent purification by silica gel column chromatography (developing solvent, ethyl acetate:hexane=1:4) produced the desired compound (3.4 g; yield, 60%) as a white solid.

PRODUCTION EXAMPLE 24

Synthesis of 4-trifluoromethyl-N-(2-pyridyl)aniline

1) Using 4-trifluoromethyl-acetanilide (6.1 g) and 2-bromopyridine (9.5 g), a reaction was made in the same manner as in 1) of Production Example 14. The subsequent purification by silica gel column chromatography (developing solvent, ethyl acetate:hexane=1:1) produced 4-trifluoromethyl-N-(2-pyridyl)acetanilide (8.0 g, crude product) as a red oil.

2) Using the compound (8.0 g) obtained in 1), a reaction was made in the same manner as in 2) of Production Example 14. The subsequent purification by silica gel column chromatography (developing solvent, ethyl acetate:hexane=1:3) produced the desired compound (4.4 g; yield, 65%) as white crystals.

PRODUCTION EXAMPLE 25

Synthesis of 3-chloro-N-(2-pyridyl)aniline

1) Using 3-chloro-acetanilide (5.09 g) and 2-bromopyridine (9.50 g), a reaction was made in the same manner as in 1) of Production Example 14. The subsequent purification by silica gel column chromatography (developing solvent, ethyl acetate:hexane=2:3) produced 3-chloro-N-(2-pyridyl)acetanilide (8.08 g, crude product) as a brown oil.

2) Using the compound (8.00 g) obtained in 1), a reaction was made in the same manner as in 2) of Production Example 14. The subsequent purification by silica gel column chromatography (developing solvent, ethyl acetate:hexane:chloroform=1:7:2) produced the desired compound (4.82 g; yield, 79%) as a white solid.

PRODUCTION EXAMPLE 26

Synthesis of 2-fluoro-N-(2-pyridyl)aniline

1) Using 2-fluoroacetanilide (4.6 g) and 2-bromopyridine (9.5 g), a reaction was made in the same manner as in 1) of Production Example 14. The subsequent purification by silica gel column chromatography (developing solvent, ethyl acetate:hexane=1:1.5) produced 2-fluoro-N-(2-pyridyl)acetanilide (5.2 g, crude product) as a red oil.

2) Using the compound (5.2 g) obtained in 1), a reaction was made in the same manner as in 2) of Production Example 14. The subsequent purification by silica gel column chromatography (developing solvent, ethyl acetate:hexane=1:5) produced the desired compound (2.0 g; yield, 47%) as white crystals.

PRODUCTION EXAMPLE 27

Synthesis of 2-chloro-N-(2-pyridyl)aniline

1) Using 2-chloro-acetanilide (5.1 g) and 2-bromopyridine (9.5 g), a reaction was made in the same manner as in 1) of Production Example 14. The subsequent purification by silica gel column chromatography (developing solvent, ethyl acetate:hexane=1:2 to 1:1) produced 2-chloro-N-(2-pyridyl)acetanilide (6.9 g, crude product) as a red oil.

2) Using the compound (6.9 g) obtained in 1), a reaction was made in the same manner as in 2) of Production Example 14. The subsequent purification by silica gel column chromatography (developing solvent, ethyl acetate:hexane=1:3) produced the desired compound (3.45 g; yield, 56%) as white crystals.

PRODUCTION EXAMPLE 28

Synthesis of 3,5-difluoro-N-(2-pyridyl)aniline

1) Using 3,5-difluoro-aniline (3.8 g), a reaction was made in the same manner as in 1) of Production Example 16 to obtain 3,5-difluoroacetanilide (4.86 g; yield, 97%) as a white solid.

2) Using the compound (4.8 g) obtained in 1) and 2-bromopyridine (8.85 g), a reaction was made in the same manner as in 1) of Production Example 14. The subsequent purification by silica gel column chromatography (developing solvent, ethyl acetate:hexane=1:2 to 1:1) produced 3,5-difluoro-N-(2-pyridyl)acetanilide (6.46 g, crude product) as a red oil.

3) Using the compound (6.4 g) obtained in 2), a reaction was made in the same manner as in 2) of Production Example 14. The subsequent purification by silica gel column chromatography (developing solvent, ethyl acetate:hexane=1:3) produced the desired compound (3.54 g; yield, 61%) as a white solid.

PRODUCTION EXAMPLE 29

Synthesis of 3-fluoro-N-phenyl-aniline

1) Using 3-fluoroacetanilide (4.6 g) and bromobenzene (9.4 g), a reaction was made in the same manner as in 1) of Production Example 14. The subsequent purification by silica gel column chromatography (developing solvent, ethyl acetate:hexane=1:2) produced 3-fluoro-N-phenylacetanilide (1.46 g; yield, 21%) as a purple oil.

2) Using the compound (1.46 g) obtained in 1), a reaction was made in the same manner as in 2) of Production Example 14. The subsequent purification by silica gel column chromatography (developing solvent, ethyl acetate:hexane=1:6) produced the desired compound (1.15 g; yield, 96%) as a pale brown oil.

PRODUCTION EXAMPLE 30

Synthesis of 3-methyl-N-(2-pyridyl)aniline

1) Using 3-methylacetanilide (4.48 g) and 2-bromopyridine (9.49 g), a reaction was made in the same manner as in 1) of Production Example 14. The subsequent purification by silica gel column chromatography (developing solvent, ethyl acetate:hexane=1:1) produce 3-methyl-N-(2-pyridyl)acetanilide (6.87 g, crude product) as a pale yellow oil.

2) Using the compound (6.9 g) obtained in 1), a reaction was made in the same manner as in 2) of Production Example 14. The subsequent purification by silica gel column chromatography (developing solvent, ethyl acetate:hexane=1:3) produced the desired compound (4.94 g; yield, 89%) as white crystals.

PRODUCTION EXAMPLE 31

Synthesis of 3-methoxy-N-(2-pyridyl)aniline

1) Using 3-methoxyaniline (4.93 g), a reaction was made in the same manner as in 1) of Production Example 16 to obtain a pale brown solid compound (6.6 g, quantitative).

2) Using 3-methoxyacetoanilide (4.96 g) obtained in 1) and 2-bromopyridine (9.49 g), a reaction was made in the same manner as in 1) of Production Example 14. The subsequent purification by silica gel column chromatography (developing solvent, ethyl acetate: hexane=1:1 to 2:1) produced 3-methoxy-N-(2-pyridyl)acetanilide (6.6 g, crude product) as a reddish brown oil.

3) Using the compound (6.6 g) obtained in 2), a reaction was made in the same manner as in 2) of Production Example 14. The subsequent purification by silica gel column chromatography (developing solvent, ethyl acetate: hexane=1:4 to 1:3) produced the desired compound (4.77 g; yield, 80%) as a colorless oil.

PRODUCTION EXAMPLE 32

Synthesis of 3-fluoro-N-(3-fluorophenyl)aniline

1) Using 3-fluoro-acetanilide (3.4 g) and 1-fluoro-3-iodobenzne (10.0 g), a reaction was made in the same manner as in 1) of Production Example 14. The subsequent purification by silica gel column chromatography (developing solvent, ethyl acetate: hexane=1:3) produced 3-fluoro-N-(3-fluorophenyl)acetanilide (3.08 g; yield, 56%) as a brown oil.

2) Using the compound (3.08 g) obtained in 1), a reaction was made in the same manner as in 2) of Production Example 14 to obtain the desired compound as a crude product.

PRODUCTION EXAMPLE 33

Synthesis of 2-methyl-N-(2-pyridyl)aniline

1) Using 2-methylacetanilide (4.5 g) and 2-bromopyridine (9.5 g), a reaction was made in the same manner as in 1) of Production Example 14. The subsequent purification by silica gel column chromatography (developing solvent, ethyl acetate: hexane=1:1) produced 2-methyl-n-(2-pyridyl)acetanilide (6.9 g, crude product) as a yellow oil.

2) Using the compound (6.9 g) obtained in 1), a reaction was made in the same manner as in 2) of Production Example 14. The subsequent purification by silica gel column chromatography (developing solvent, ethyl acetate: hexane=1:4) produced the desired compound (4.0 g; yield, 72%) as a white solid.

PRODUCTION EXAMPLE 34

Synthesis of 2-methoxy-N-(2-pyridyl)aniline

1) Using 2-methoxy-acetanilide (5.0 g) and 2-bromopyridine (9.5 g), a reaction was made in the same manner as in 1) of Production Example 14. The subsequent purification by silica gel column chromatography (developing solvent, ethyl acetate: hexane=1:1) produced 2-methoxy-N-(2-pyridyl)acetanilide (4.3 g, crude product) as a yellow oil.

2) Using the compound (4.3 g) obtained in 1), a reaction was made in the same manner as in 2) of Production Example 14. The subsequent purification by silica gel column chromatography (developing solvent, ethyl acetate: hexane=1:3.5) produced the desired compound (2.4 g; yield, 40%) as a white solid.

PRODUCTION EXAMPLE 35

Synthesis of 3-nitro-N-(2-pyridyl)aniline

1) Using 3-nitroacetanilide (5.4 g) and 2-bromopyridine (9.49 g), a reaction was made in the same manner as in 1)

of Production Example 14. The subsequent purification by silica gel column chromatography (developing solvent, ethyl acetate: hexane=1:1 to ethyl acetate) produced 3-nitro-N-(2-pyridyl)acetanilide (6.64 g, crude product) as a pale brown oil.

2) Using the compound (6.64 g) obtained in 1), a reaction was made in the same manner as in 2) of Production Example 14. The subsequent purification by silica gel column chromatography (developing solvent, ethyl acetate: hexane=1:1 to chloroform) produced the desired compound (3.58 g; yield, 55%) as a yellow solid.

PRODUCTION EXAMPLE 36

Synthesis of 2,6-difluoro-N-(2-pyridine)aniline

1) Using 2,6-difluoroaniline (10 g), a reaction was made in the same manner as in 1) of Production Example 16 to obtain 2,6-difluoro-acetanilide (13.6 g, quantitative) as a white solid.

2) Using the compound (5.13 g) obtained in 1) and 2-bromopyridine (9.49 g), a reaction was made in the same manner as in 1) of Production Example 14. The subsequent purification by silica gel column chromatography (developing solvent, ethyl acetate: hexane=1:2 to 1:1) produced 2,6-difluoro-N-(2-pyridyl)acetanilide (8.0 g, crude product) as a pale yellow oil.

3) Using the compound (8.0 g) obtained in 2), a reaction was made in the same manner as in 2) of Production Example 14. The subsequent purification by silica gel column chromatography (developing solvent, ethyl acetate: hexane=1:4) produced the desired compound (3.68 g; yield, 66%) as a white solid.

PRODUCTION EXAMPLE 37

Synthesis of 2,3-difluoro-N-(2-pyridyl)aniline

1) Using 2,3-difluoroaniline (10 g), a reaction was made in the same manner as in 1) of Production Example 16 to obtain 2,3-difluoro-acetanilide (12.6 g; yield, 95%) as a white solid.

2) Using the compound (5.13 g) obtained in 1) and 2-bromopyridine bromopyridine (9.49 g), a reaction was made in the same manner as in 1) of Production Example 14. The subsequent purification by silica gel column chromatography (developing solvent, ethyl acetate: hexane=1:1) produced 2,3-difluoro-N-(2-pyridyl)acetanilide (8.8 g, crude product) as a pale yellow oil.

3) Using the compound (8.8 g) obtained in 2), a reaction was made in the same manner as in 2) of Production Example 14. The subsequent purification by silica gel column chromatography (developing solvent, ethyl acetate: hexane=1:4) produced the desired compound (4.80 g; yield, 78%) as a white solid.

PRODUCTION EXAMPLE 38

Synthesis of 11-hydro-10-methyl-5H-dibenzo[b,e][1,4]diazepin-11-one

A 1,4-dioxane (25 ml) solution of 10,11-dihydro-5H-dibenzo[b,e][1,4]diazepin-11-one (2 g) and potassium tert-butoxide (2.35 g) was heated under reflux. After 1 hour, methyl iodide (1.78 ml) was added to the solution without cooling, and the resulting solution was further heated under reflux. After 4 hours, the solution was allowed to cool to room temperature and concentrated under reduced pressure. The thus-obtained residue was dissolved in chloroform and washed with a sodium bicarbonate aqueous solution then with water and saturated brine, dried over sodium sulfate, and filtered. The filtrate was concentrated, and the resulting residue was purified by silica gel chromatography (developing solvent, chloroform: methanol=100:1 to 50:1) to obtain the desired compound (1.14 g; yield, 53%) as a pale brown white solid.

PRODUCTION EXAMPLE 39

Synthesis of 2-methyl-N-(3-methyl-2-pyridine)aniline

1) Using 2-methylacetanilide (4.48 g) and 2-bromo-3-methylpyridine (10.3 g), a reaction was made in the same manner as in 1) of Production Example 14. The subsequent purification by silica gel column chromatography (developing solvent, ethyl acetate: hexane=1:3) produced 2-methyl-N-(3-methyl-2-pyridyl)acetanilide (7.2 g, crude product) as a pale brown oil.

2) Using the compound (7.2 g) obtained in 1), a reaction was made in the same manner as in 2) of Production Example 14. The subsequent purification by silica gel column chromatography (developing solvent, ethyl acetate: hexane=1:5) produced the desired compound (3.98 g; yield, 67%) as a white solid.

PRODUCTION EXAMPLE 40

Synthesis of 2-ethyl-N-(2-pyridyl)aniline

1) Using 2-ethyl-aniline (10 g), a reaction was made in the same manner as in 1) of Production Example 16 to obtain 2-ethyl-acetanilide (13.2 g; yield, 98%) as a white solid.

2) Using the compound (4.9 g) obtained in 1) and 2-bromopyridine (9.49 g), a reaction was made in the same manner as in 1) of Production Example 14. The subsequent purification by silica gel column chromatography (developing solvent, ethyl acetate: hexane=1:2) produced 2-ethyl-N-(2-pyridyl)acetanilide (8.34 g, crude product) as a pale brown oil.

3) Using the compound (8.34 g) obtained in 2), a reaction was made in the same manner as in 2) of Production Example 14. The subsequent purification by silica gel column chromatography (developing solvent, ethyl acetate: hexane=1:5) produced the desired compound (3.28 g; yield, 55%) as a white solid.

PRODUCTION EXAMPLE 41

Synthesis of 2-propyl-N-(2-pyridyl)aniline

1) Acetyl chloride (5.6 ml) and triethylamine (12.5 ml) were added dropwise to a chloroform (50 ml) solution of 2-propylaniline (10.5 g) in this order under ice-cooling. The reaction solution was stirred at room temperature for 3 hours. The solution was concentrated under reduced pressure, and the thus-obtained solid was washed with water and collected by filtration. The resulting residue was recrystallized from ethanol-water to obtain 2-propylacetanilide (11.85 g; yield, 86%) as white crystals.

2) Using the compound (10.6 g) obtained in 1) and 2-bromopyridine (18.9 g), a reaction was made in the same manner as in 1) of Production Example 14. The subsequent purification by silica gel column chromatography (developing solvent, ethyl acetate: hexane=1:2) produced 2-propyl-N-(2-pyridyl)acetanilide (14.4 g, crude product) as a yellow oil.

3) Using the compound (14.4 g) obtained in 2), a reaction was made in the same manner as in 2) of Production Example 14. The subsequent purification by silica gel column chromatography (developing solvent, ethyl acetate: hexane=1:4) produced the desired compound (10.6 g; yield, 88%) as white crystals.

PRODUCTION EXAMPLE 42

Synthesis of 9,10-dihydro-9,9-dimethylacridine

1) A mixture of methyl 2-aminobenzoate (7 g), iodobenzene (3.9 ml), potassium carbonate (6.4 g), and copper powder (0.46 g) was heated at 180° C. for 17 hours. The reaction solution was allowed to cool to room temperature, and ethyl acetate was added thereto. The resulting mixture was stirred and filtered with celite. The filtrate was washed with ethyl acetate and concentrated under reduced pressure. The thus-obtained residue was purified by silica gel column chromatography (developing solvent, ethyl acetate: hexane= 1:30) to obtain methyl 2-phenylaminobenzoate (7.13 g; yield, 90%) as a pale yellow solid.

2) Methyl lithium (89 ml) was added dropwise to an ether (35 ml) solution of the compound (7.1 g) obtained in 1) at a temperature of −78° C. in a stream of argon air, and the solution was stirred for 3.5 hours at room temperature. Ice was put into the reaction solution, and the solution was stirred in an ice bath. After the solution was extracted with ether, the extract was washed with water and saturated brine, dried over sodium sulfate, and filtered. The filtrate was concentrated and dried to obtain N-[2-(1-hydroxy-1-methylethyl)phenyl]aniline (6.3 g, crude product) as a pale brown oil.

3) A phosphoric acid (60 ml) solution of the compound (3 g) obtained in 2) was stirred at room temperature for 17 hours. After water was added, the solution was made basic with sodium hydroxide and extraction with ethyl acetate. The organic phase was washed with water and saturated brine, dried over sodium sulfate, and filtered. The filtrate was concentrated under reduced pressure, and the resulting residue was purified by silica gel column chromatography (developing solvent, ethyl acetate: hexane=1:30) to obtain the desired compound (123 mg; yield, 4%) as a yellowish white solid.

PRODUCTION EXAMPLE 43

Synthesis of 4H-3,1-benzoxazin-4-one

1) A toluene (1100 ml) solution of anthranilic acid (205.5 g) and formic acid (170 ml) was heated under reflux for 4.5 hours. After the solution was allowed to cool, hexane was added to crystals deposited. The crystals were collected by filtration and washed with hexane. The resulting crystals were dried at 110° C. under reduced pressure to obtain N-formyl-anthranilic acid (244.0 g, crude product) as white crystals.

2) Triethyl orthoformate (550 ml) was added to the compound (272.8 g) obtained in 1), and the mixture was heated to make a solution. The solution was distilled at ordinary pressure to remove substances with boiling points of about 75° C. Unreacted triethyl orthoformate was removed by evaporation under reduced pressure. The resulting residue was evaporated at 140° C. under reduced pressure, and the thus-obtained liquid was allowed to cool to obtain the desired compound (148.1 g; yield, 61%) as white to pale yellow crystals.

PRODUCTION EXAMPLE 44

Synthesis of N-(2-bromoethyl)-10,11-dihydro-10-hydroxy-5H-dibenzo[b,f]azepine

1) Acetyl chloride (11.0 ml) was added to a chloroform (250 ml) solution of 5H-dibenzo[b,f]azepine (25.0 g) under ice-cooling. The solution was heated under reflux for 30 minutes, then allowed to cool. The organic phase was washed with a saturated sodium bicarbonate aqueous solution, water, and saturated brine; dried over anhydrous sodium sulfate; and filtered. The filtrate was concentrated, and the resulting residue was recrystallized from ethyl acetate-hexane to obtain N-acetyl-5H-dibenzo[b,f]azepine (28.6 g; yield, 94%) as a white solid.

2) Sodium hypochlorite (150 ml) and silicone dioxide (10 g) were added to an acetonitrile (20 ml) solution of the compound (7.00 g) obtained in 1). The mixture was heated under reflux for 2 hours, allowed to cool, and filtered. The filtrate was extracted with chloroform. The organic phase was washed with water and saturated brine, dried over anhydrous sodium sulfate, and concentrated. The thus-obtained residue was purified by silica gel column chromatography (developing solvent, ethyl acetate: hexane=1:2) to obtain N-acetyl-5H-dibenzo[b,f]azepine-10,11-epoxide (3.45 g; yield, 46%) as a yellow amorphous substance.

3) Lithium iodide (1.86 g) was added to a chloroform (35 ml) solution of the compound (3.45 g) obtained in 2), and the solution was heated under reflux for 15 minutes. After the solution was allowed to cool, the solution was washed with a 10% sodium sulfite aqueous solution, then with water and saturated brine. The resulting solution was dried over anhydrous sodium sulfate and filtered. The filtrate was concentrated, and the thus-obtained residue was purified by silica gel column chromatography (developing solvent, ethyl acetate: hexane=1:1) to obtain N-acetyl-10,11-dihydro-10-oxo-5-H-dibenzo[b,f]azepine (3.04 g; yield, 94%) as a yellow solid.

4) Potassium tert-butoxide (3.1 g) and water (153 µl) were added to a tetrahydrofuran (20 ml) solution of the compound (1.01 g) obtained in 3), and the solution was stirred at 80° C. for 1.5 hours under heating. The solution was allowed to cool and poured into water, followed by extraction with ethyl acetate. The organic phase was washed with water and saturated brine, dried over anhydrous sodium sulfate, and filtered. The filtrate was concentrated and the resulting residue was purified by silica gel column chromatography (developing solvent, ethyl acetate: hexane=1:5) to obtain 10,11-dihydro-10-oxo-5H-dibenzo[b,f]azepine (624 mg; yield, 69%) as a yellow solid.

5) Bromoacetylbromide (478 µl) was added to a chloroform (10 ml) solution of the compound (524 mg) obtained in 4), and the solution was heated under reflux for 30 minutes. The solution was allowed to cool, washed with water and saturated brine, and dried over anhydrous sodium sulfate. After filtration, the filtrate was concentrated, and the resulting residue was purified by silica gel column chromatography (developing solvent, ethyl acetate: hexane=1:3) to obtain white amorphous N-(2-bromoacetyl)-10,11-dihydro-10-oxo-5H-dibenzo[b,f]azepine (827 mg, quantitative).

6) BH$_3$-tetrahydrofuran (6.6 ml) was added to a tetrahydrofuran (10 ml) solution of the compound (827 mg) obtained in 5). The solution was stirred for 30 minutes under ice-cooling, then at room temperature for 1 hour. After the solution was poured into water, the mixture was extracted with ethyl acetate. The organic phase was washed with water and saturated brine, dried over anhydrous sodium sulfate, and filtered. The filtrate was concentrated, and the resulting residue was purified by silica gel column chromatography (developing solvent, ethyl acetate: hexane=1:5) to a pale yellow amorphous substance to obtain the desired compound (545 mg; yield, 68%).

PRODUCTION EXAMPLE 45

Synthesis of N-(2-chloroethyl)-10,11-dihydro-2-hydroxy-5H-dibenzo[b,f]-azepine

1) Phosphoryl trichloride (12.3 ml) was added dropwise to dimethyl formamide anhydride (20.9 ml) in a nitrogen atmosphere and under ice-cooling, and the solution was stirred at room temperature for 10 minutes. N-(2-bromoethyl)-10,11-dihydro-5H-dibenzo[b,f]-azepine (16.0 g) was added to the reaction solution under ice-cooling, and the solution was stirred at 100° C. for 20 minutes. The solution was poured into ice water, neutralized with a 2N sodium hydroxide aqueous solution, and extracted with ethyl acetate. The extract was washed with water and saturated brine, dried over anhydrous sodium sulfate, and filtered. The filtrate was concentrated and the resulting residue was purified by silica gel column chromatography (developing solvent, ethyl acetate: hexane=1:10 to 1:5) to obtain N-(2-chloroethyl)-2-formyl-10,11-dihydro-5H-dibenzo[b,f]azepine (13.3 g; yield, 88%) as a reddish yellow oil.

2) Trifluoroacetic acid (12.1 ml) was added to a dichloromethane (130 ml) solution of the compound (12.80 g) obtained in 1) under ice-cooling. A dichloromethane (60 ml) solution of m-chlorobenzoic acid (14.3 g) was then slowly added dropwise thereto. The solution was stirred at room temperature for 1.5 hours and neutralized with a saturated sodium bicarbonate aqueous solution to separate the organic phase. The aqueous phase was extracted with chloroform. The resulting extract was combined with the above organic phase. The combined organic phase was washed with water and saturated brine, dried over anhydrous sodium sulfate, and filtered. The filtrate was concentrated and the thus-obtained residue was purified by silica gel column chromatography (developing solvent, ethyl acetate: hexane=1:7) to obtain N-(2-chloroethyl)-2-formyloxy-10,11-dihydro-5H-dibenzo[b,f]azepine (4.88 g; yield, 36%) as a colorless oil.

3) Sulfuric acid (1 ml) was added to a chloroform (5 ml)-methanol (50 ml) mixed solution of the compound (4.83 g) obtained in 2), and the solution was stirred at room temperature for 2 hours. After concentration, ethyl acetate was added thereto, and the solution was washed with water and saturated brine, and dried over anhydrous sodium sulfate. After filtration, the filtrate was concentrated to obtain N-(2-chloroethyl)-10,11-dihydro-2-hydroxy-5H-dibenzo[b,f]azepine (4.05 g) as pale yellow crude crystals.

The compounds produced in Production Examples 1 to 45 are listed in Tables 1 and 2.

TABLE 1

| Production Example | Compound | Production Example | Compound | Production Example | Compound |
|---|---|---|---|---|---|
| 1 | | 9 | | 17 | |
| 2 | | 10 | | 18 | |
| 3 | | 11 | | 19 | |
| 4 | | 12 | | 20 | |
| 5 | | 13 | | 21 | |

TABLE 1-continued
| Production Example | Compound | Production Example | Compound | Production Example | Compound |
|---|---|---|---|---|---|
| 6 | 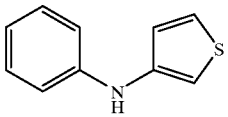 | 14 | 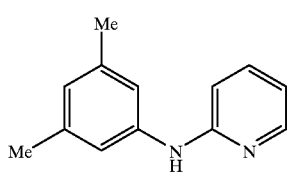 | 22 | 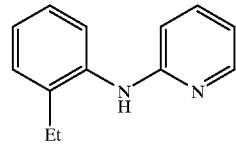 |
| 7 | 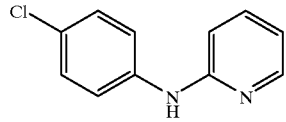 | 15 | 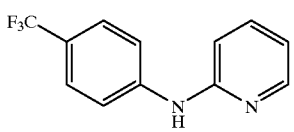 | 23 | 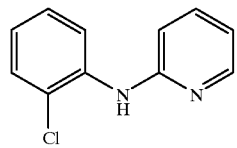 |
| 8 | 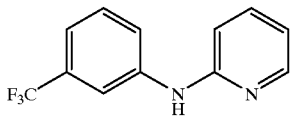 | 16 | 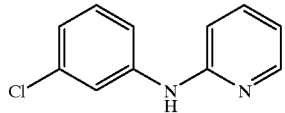 | 24 | 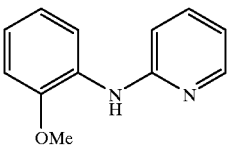 |
TABLE 2
| Production Example | Compound | Production Example | Compound | Production Example | Compound |
|---|---|---|---|---|---|
| 25 | 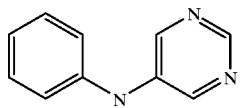 | 32 | 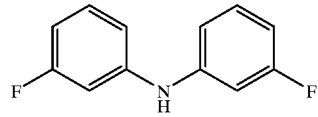 | 39 | 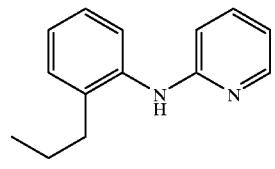 |
| 26 | 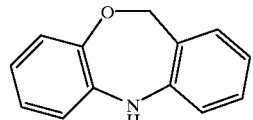 | 33 | 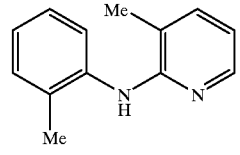 | 40 | 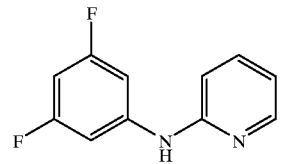 |
| 27 | 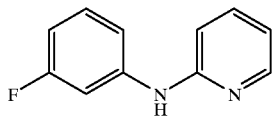 | 34 | 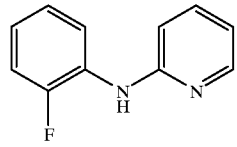 | 41 | 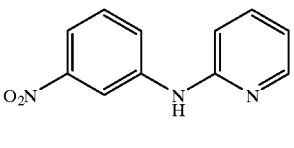 |
| 28 | 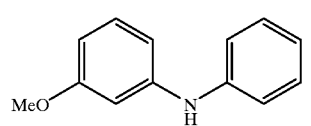 | 35 | 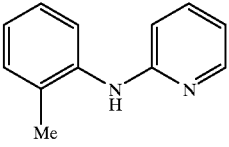 | 42 | 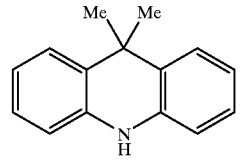 |

TABLE 2-continued

| Production Example | Compound | Production Example | Compound | Production Example | Compound |
|---|---|---|---|---|---|
| 29 | F-C6H4-NH-C6H5 | 36 | 2,6-F2-C6H3-NH-(2-pyridyl) | 43 | 4H-benzo[d][1,3]oxazin-4-one |
| 30 | 3-Me-C6H4-NH-(2-pyridyl) | 37 | 2,3-F2-C6H3-NH-(2-pyridyl) | 44 | Br-CH2CH2-N(dibenzazepine)-OH |
| 31 | 3-MeO-C6H4-NH-(2-pyridyl) | 38 | 5-Me-dibenzo[b,e][1,4]diazepin-11(10H)-one | 45 | Cl-CH2CH2-N(dibenzazepine)-OH |

EXAMPLE 1

Synthesis of 3-[1-(2-(N,N-diphenylamino)ethyl]piperidine-4-yl]-3H-quinazolin-4-one Dihydrochloride Step 14) (2-bromoethyl)diphenylamine (VIII)

1,2-Dibromoethane (49 ml) was added to a diisopropylethylamine (48.6 ml) solution of diphenylamine (4.7 g), and the solution was heated under reflux for 14 hours at 135° C. After the solution was allowed to cool to room temperature, the solid was triturated, collected by filtration, and washed with toluene. The filtrate was concentrated under reduced pressure, and the thus-obtained residue was purified by silica gel column chromatography (developing solvent, hexane) to obtain the desired compound (2.0 g; yield, 26%) as a pale yellow oil.

Step 1) 2-Amino-N-(1-ethoxycarbonyl-piperidin-4-yl) benzamide (V)

1-Ethyl-3-(3-dimethylaminopropyl)carbodiimide hydrochloride (64.9 g) was added to a dimethylformamide (500 ml) solution of 2-aminobenzoic acid (42.2 g), ethyl 4-aminopiperidinecarboxylate (53 g), and 1-hydroxybenzotriazole (45.7 g) under ice-cooling, and the solution was stirred overnight at room temperature. After the reaction solution was concentrated, water was added thereto, and the solution was extracted with ethyl acetate. The organic phase was washed sequentially with a 10% citric acid aqueous solution, water, a saturated sodium bicarbonate aqueous solution, water, and saturated brine, and dried over sodium sulfate. The thus-obtained residue was recrystallized from ethyl acetate-hexane to obtain the desired compound (64.5 g; yield, 72%) as pale yellow crystals.

Step 2) 3-(1-Ethoxycarbonyl-piperidin-4-yl)-3H-quinazolin-4-one (VI)

A formic acid (350 ml) solution of the compound (64.5 g) obtained in the above Step 1) was heated under reflux for 16 hours. The reaction solution was allowed to cool to room temperature, concentrated under reduced pressure, and extracted with chloroform. After a saturated sodium bicarbonate aqueous solution was added to the extract, it was washed with water and saturated brine, dried over sodium sulfate, and concentrated under reduced pressure to obtain the desired compound (60.7 g; yield, 91%) as a pale beige solid.

Step 3) 3-(Piperidine-4-yl)-3H-quinazolin-4-one (VII)

25% Hydrogen bromide-acetic acid (385 ml) was added to the compound (60.7 g) obtained in the above Step 2), and the solution was stirred for 18 hours at 60° C. The reaction solution was concentrated under reduced pressure, neutralized with 4N sodium hydroxide, and extracted with chloroform. The extract was washed with water and saturated brine, dried over sodium sulfate, and concentrated under reduced pressure to obtain the desired compound (40.7 g; yield, 88%) as a white powder.

Step 4) 3-[1-[2-(N,N-diphenylamino)ethyl]piperidin-4-yl]-3H-quinazolin-4-one (I)

An acetonitrile (14 ml) solution of the compound (1.6 g) obtained in the above Step 3), the compound (1.9 g) obtained in the above Step 14), and potassium carbonate (1.9 g) was heated under reflux overnight. After water was added thereto, the solution was extracted with chloroform. The extract was washed with water and saturated brine, and dried over sodium sulfate. The thus-obtained residue was purified by silica gel column chromatography (developing solvent, ethyl acetate:hexane=1:1) to obtain the desired compound (1.6 g; yield, 55%) as a white solid.

Step 13) Hydrogen chloride-ether (15 ml) was added to a chloroform (1 ml) solution of the compound (1 g) obtained in the above Step 4) under ice-cooling, and the solution was stirred at room temperature for 0.5 hours. Crystals deposited were collected by filtration, washed with ether, and dried to obtain the desired compound (1.10 g; yield, 94%) as white crystals.

EXAMPLE 2

Synthesis of 3-[1-[2-(5H-dibenzo[b,f]azepin-5-yl) ethyl]piperidin-4-yl]-3H-quinazolin-4-one Hydrochloride Step 14) N-(2-bromoethyl)-5H-dibenzo[b,f]azepine (VIII)

A diisopropylethylamine (100 ml) solution of 5H-dibenzo-[b,f]azepine (10.0 g) and 1,2-dibromoethane was stirred at 130° C. for 4.5 hours. The solution was then allowed to cool to room temperature, filtered, and washed with toluene. After the filtrate was concentrated, the concentrate was purified by silica gel column chromatography (developing solvent, chloroform) to obtain the desired compound (15.0 g; yield, 97%) as a yellow solid.

Step 4) 3-[1-[2-(5H-dibenzo[b,f]azepin-5-yl)ethyl] piperidin-4-yl]-3H-quinazolin-4-one (I)

Using the compound (500 mg) obtained in the above Step 14) and the compound (720 mg) obtained in Step 3) of Example 1, a reaction was performed in the same manner as in Step 4) of Example 1. The thus-obtained residue was purified by silica gel column chromatography (developing solvent, chloroform:methanol=40:1) to obtain the desired compound (888 mg; yield, 91%) as a yellow solid.

Step 13) Using the compound (888 mg) obtained in the above Step 4), the reaction was performed in the same manner as in Step 13) of Example 1 to obtain the desired compound (960 mg, quantitative) as a pale yellow powder.

EXAMPLE 3

Synthesis of 3-[1-[2-(N-benzyl-N-phenylamino) ethyl]piperidin-4-yl]-3H-quinazolin-4-one Hydrochloride Step 14) N-(2-bromoethyl)-N-benzylaniline (VIII)

Using N-benzylaniline (916 mg) and 1,2-dibromoethane (9.39 g), a reaction was performed in the same manner as in Step 14) of Example 1. The thus-obtained residue was purified by silica gel column chromatography (developing solvent, ethyl acetate:hexane=1:40) to obtain the desired compound (1.18 g; yield, 81%) as a blue-yellowish white oil.

Step 4) 3-[1-[2- (N-benzyl-N-phenylamino)ethyl] piperidin-4-yl]-3H-quinazolin-4-one (I)

Using the compound (696 mg) obtained in the above Step 14) and the compound (459 mg) obtained in the above Step 3) of Example 1, a reaction was performed in the same manner as in Step 4) of Example 1. The thus-obtained residue was recrystallized from ethyl acetate to obtain the desired compound (678 mg; yield, 71%) as pale brown needle crystals.

Step 13) Using the compound (673 mg) obtained in the above Step 4), a reaction was performed in the same manner as in Step 13) of Example 1 to obtain the desired compound (648 mg; yield, 89%) as colorless needle crystals.

EXAMPLE 4

Synthesis of 3-[1-[3-(10,11-dihydro-5H-dibenzo[b,f] azepin-5-yl) propyl]piperidin-4-yl]-3H-quinazolin-4-one Step 14) N-(3-bromopropyl)-10,11-dihydro-5H-dibenzo [b,f]azepine (VIII)

Using 5H-dibenzo[b,f]azepine (5.0 g) and 1,3-dibromopropane (52.2 g), a reaction was performed in the same manner as in Step 14) of Example 1. The thus-obtained residue was purified by silica gel column chromatography (developing solvent, hexane to chloroform) to obtain a crude product (10.0 g) as yellow oil.

7.5% Palladium-on-carbon (50% hydrated, 1.0 g) was added to a tetrahydrofuran (50 ml) solution of the thus-obtained crude product (5.1 g), and the solution was stirred at room temperature for 5.5 hours under normal pressure. After the reaction solution was filtered with celite, the filtrate was concentrated and purified by silica gel column chromatography (developing solvent, hexane to chloroform) to obtain the desired compound (4.05 g; yield, 99%) as a white solid.

Step 4) Using the compound (759 mg) obtained in the above Step 14) and the compound (500 mg) obtained in the above Step 3) of Example 1, a reaction was performed in the same manner as in Step 4) of Example 1. The thus-obtained residue was purified by silica gel column chromatography (developing solvent, chloroform:methanol=40:1). The resulting product was further subjected to recrystallization from ethyl acetate-hexane to obtain the desired compound (745 mg; yield, 74% as a white solid.

EXAMPLE 5

Synthesis of 3-[1-[2-(10,11-dihydro-11-oxo-5H-dibenzo[b,e][1,4]-diazepin-5-yl)ethyl]piperidin-4-yl]-3H-quinazolin-4-one Hydrochloride Step 14) 5-(2-bromoethyl)-10,11-dihydro-5H-dibenzo[b, e][1,4]-diazepin-11-one (VIII)

Using the compound (1.0 g) obtained in Production Example 1 and 1,2-dibromoethane (8.94 g), a reaction was performed in the same manner as in Step 14) of Example 1. The thus-obtained residue was purified by silica gel column chromatography (developing solvent, ethyl acetate:hexane= 1:2) to obtain the desired compound (146 mg; yield, 9.7%) as a pale, yellowish-white, amorphous substance.

Step 4) 3-[1-[2-(10,11-dihydro-11-oxo-5H-dibenzo[b,e] [1,4]-diazepin-5-yl)ethyl]piperidin-4-yl]-3H-quinazolin-4-one (I)

An acetonitrile (5 ml) solution of the compound (240 mg) obtained in the above Step 14), the compound (174 mg) obtained in Step 3) of Example 1, potassium carbonate (105 mg), and sodium iodide (117 mg) was heated under reflux for 14 hours. After the solution was allowed to cool to room temperature, water was added thereto, and the solution was extracted with ethyl acetate. The extract was washed with water and saturated brine, and dried over sodium sulfate. The resulting residue was purified by silica gel column chromatography (developing solvent, chloroform:methanol=20:1) to obtain the desired compound (246 mg; yield, 70%) as a white solid.

Step 13) Using the compound (240 mg) obtained in the above Step 4), a reaction was performed in the same manner as in Step 13) of Example 1 to obtain the desired compound (238 mg; yield, 91%) as a white solid.

EXAMPLE 6

Synthesis of 3-[1-[4-(N,N-diphenylamino)butyl]piperidin-4-yl]-3H-quinazolin-4-one Hydrochloride Step 15) 4-(N,N-diphenylamino)butyl acetate (XXI)

A dimethylsulfoxide anhydride (10 ml) solution of sodium hydride (1.4 g) was stirred at 50° C. for 15 minutes in a stream of argon gas. A dimethylsulfoxide (15 ml) solution of diphenylamine (3.0 g) was added thereto under ice-cooling, and the solution was stirred at room temperature for 0.5 hours. After 4-bromobutyl acetate (10.4 g) was added thereto, the reaction solution was stirred at 60° C. for an additional 4.5 hours. Water was then added thereto under ice-cooling, and the solution was extracted with ethyl acetate. The extract was washed with water and saturated brine, and dried over sodium sulfate. The thus-obtained residue was purified by silica gel column chromatography (developing solvent, ethyl acetate:hexane=1:10) to obtain a crude product (7.5 g) as a yellow oil.

Step 16) 4-(N,N-diphenylamino)butanol (XXII)

A 1N sodium hydroxide aqueous solution (53 ml) was added to a methanol (80 ml) solution of the crude product (7.5 g) obtained in the above Step 15), and the solution was stirred at room temperature for 2.5 hours. After the reaction solution was concentrated, water was added to the concentrate, and the resulting solution was extracted with ethyl acetate. The extract was washed with water and saturated brine, and dried over sodium sulfate. The thus-obtained residue was purified by silica gel column chromatography (developing solvent, ethyl acetate:hexane=1:3) to obtain the desired compound (3.6 g; yield, 84%) as a colorless oil.

Step 17) 4-(N,N-diphenylamino)butyl methanesulfonate (VIII)

Triethylamine (0.69 ml) and methanesulfonyl chloride (0.39 ml) were added to a dichloromethane (15 ml) solution of the compound (1.0 g) obtained in Step 16) under ice-cooling, and the resulting solution was stirred at room temperature for 10 minutes. After the solution was extracted with chloroform, the extract was washed with water and saturated brine, and dried over sodium sulfate. The thus-obtained residue was purified by silica gel column chromatography (developing solvent, ethyl acetate:hexane=1:2) to obtain the desired compound (1.1 g; yield, 86%) as a colorless oil.

Step 4) 3-[1-[4-(N,N-diphenylamino)butyl]piperidin-4-yl]-3H-quinazolin-4-one (I)

An acetonitrile (6 ml) solution of the compound (769 mg) obtained in the above Step 17), the compound (460 mg) obtained in Step 3) of Example 1, and potassium carbonate (276 mg) was heated under reflux overnight. After the solution was allowed to cool to room temperature, water was added thereto and the solution was extracted with chloroform. The extract was washed with water and saturated brine, and dried over sodium sulfate. The thus-obtained residue was purified by silica gel column chromatography (developing solvent, ethyl acetate to ethyl acetate:triethylamine=100:1) to obtain the desired compound (772 mg; yield, 85%) as a white solid.

Step 13) 4N Hydrogen chloride-ethyl acetate (1 ml) was added to an ethyl acetate (8 ml) solution of the compound (412 mg) obtained in the above Step 4), and the solution was stirred at room temperature for 0.5 hours. Deposited crystals were collected by filtration, washed with ethyl acetate, and recrystallized from ethanol to obtain the desired compound (443 mg, quantitative) as a white powder.

EXAMPLE 7

Synthesis of 3-[1-[2-[N-(2-methylphenyl)-N-phenylamino]ethyl]piperidin-4-yl]-3H-quinazolin-4-one Step 15) 2-[N-(2-methylphenyl)-N-phenylamino]ethyl acetate (XXI)

Sodium hydride (2.2 g) was added to an anhydrous dimethylsulfoxide (3.5 ml) solution of the compound (3.4 g) obtained in Production Example 2 in a stream of argon gas, and the solution was stirred at room temperature for 0.5 hours. 2-Bromobutyl acetate (6.2 g) was added to the reaction solution, and the solution was stirred at room temperature for 2 hours. After water was added thereto under ice-cooling, the solution was extracted with ethyl acetate. The extract was washed with water and saturated brine, and dried over sodium sulfate. The thus-obtained residue was used in the next step as it was.

Step 16) 2[N-(2-methylphenyl)-N-phenylamino)]ethanol (XXII)

A 1N sodium hydroxide aqueous (8 ml) solution was added to a methanol (4 ml)-tetrahydrofuran (4 ml) mixed solution containing the crude product obtained in the above Step 15) under ice-cooling, and the solution was stirred for 4 hours at room temperature. After the reaction solution was concentrated, methanol and tetrahydrofuran were removed by evaporation, and the resulting residue was extracted with ethyl acetate. The extract was washed with water and saturated brine, and dried over sodium sulfate. The thus-obtained residue was purified by silica gel column chromatography (developing solvent, ethyl acetate:hexane=1:4) to obtain the desired compound (1.11 g; yield, 22%) as a pale yellow oil.

Step 17) 2-[N-(2-methylphenyl)-N-phenylamino)ethyl methane-sulfonate (VIII)

Triethylamine (316 μl) and methanesulfonyl chloride (176 μl) were added to a dichloromethane (12 ml) solution of the compound (430 mg) obtained in the above Step 16), and the solution was stirred at room temperature for 3 hours. After water was added thereto, the solution was extracted with chloroform. The extract was washed with water and saturated brine, and dried over sodium sulfate. The thus-obtained residue was purified by silica gel column chromatography (developing solvent, ethyl acetate:hexane=1:3) to obtain the desired compound (577 mg, quantitative) as a pale yellow oil.

Step 4) An acetonitrile (10 ml) solution of the compound (577 mg) obtained in the above Step of 17), the compound (433 mg) obtained in Step 3) of Example 1, potassium carbonate (261 mg), and sodium iodide (283 mg) was heated under reflux overnight. After the solution was allowed to cool to room temperature, water was added thereto, and the solution was extracted with chloroform. The extract was washed with water and saturated brine, and dried over sodium sulfate. The thus-obtained residue was purified by silica gel column chromatography (developing solvent, ethyl acetate:hexane=2:1) to obtain the desired compound (540 mg; yield, 65%) as a white solid.

EXAMPLE 8

Synthesis of 3-[1-[2-[N-(2-ethylphenyl)-N-phenylamino]ethyl]piperidin-4-yl]-3H-quinazolin-4-one Hydrochloride Step 13) 4N Hydrogen chloride-ethyl acetate (1 ml) was added to a dichloromethane (5 ml) solution of the compound (110 mg) obtained in Step 4) of Example 7, and the solution was stirred at room temperature for 0.5 hours. Deposited crystals were collected by filtration, washed with ethyl acetate, and dried under reduced pressure to obtain the desired compound (114 mg; yield, 96%) as a white solid.

EXAMPLE 9

Synthesis of 3-[1-[2-(1,2,3,4-tetrahydrocarbazol-9-yl)ethyl]-piperidin-4-yl]-3H-quinazolin-4-one Step 15) 2-(1,2,3,4-tetrahydrocarbazol-9-yl)ethyl acetate (XXI)

Sodium hydride (762 mg) was added to a dimethylsulfoxide anhydride (25 ml) solution of 1,2,3,4-tetrahydrocarbazole (2 g) in a stream of argon gas, and the solution was stirred at room temperature for 10 minutes. After 2-bromoethyl acetate (3.9 g) was added to the reaction solution, the solution was stirred at room temperature for an additional 15 hours. Water (100 ml) was then added thereto, and the solution was extracted with ethyl acetate. The extract was washed with water and saturated brine, and dried over sodium sulfate. The thus-obtained residue was purified by silica gel column chromatography (developing solvent, ethyl acetate:hexane=1:10) to obtain the desired compound (2.5 g; yield, 82%) as a pale yellow oil.

Step 16) 2-(1,2,3,4-tetrahydrocarbazol-9-yl)ethanol (XXII)

A 1N sodium hydroxide aqueous (28 ml) solution was added to a methanol (15 ml)-tetrahydrofuran (10 ml) mixed solution containing the compound (2.4 g) obtained in the above Step 15) under ice-cooling, and the solution was stirred at room temperature for 6 hours. The reaction solution was concentrated under reduced pressure and extracted with ethyl acetate. The extract was washed with water and saturated brine, and dried over sodium sulfate. The thus-obtained residue was purified by silica gel column chromatography (developing solvent, ethyl acetate:hexane=1:5) to obtain the desired compound (1.70 g; yield, 85%) as a pale yellow oil.

Step 17) 2-(1,2,3,4-tetrahydrocarbazol-9-yl)ethyl methane-sulfonate (VIII)

Using the compound (1.70 g) obtained in the above Step 16), a reaction was performed in the same manner as in Step 17) of Example 6 to obtain the desired compound (1.8 g; yield, 78%) as a yellowish white solid.

Step 4) Using the compound (600 mg) obtained in the above Step 17) and the compound (468 mg) obtained in Step 3) of Example 1, a reaction was performed in the same manner as in Step 4) of Example 6 to obtain the desired compound (114 mg; yield, 13%) as a white solid.

EXAMPLE 10

Synthesis of 3-[1-[3-(N,N-diphenylamino)propyl]piperidin-4-yl]-3H-quinazolin-4-one Hydrochloride Step 15) O-tert-butyldimethylsilyl 3-(N,N-diphenylamino)propanol (XXI)

A dimethylsulfoxide anhydride (60 ml) solution of diphenylamine (5 g) was stirred at room temperature for 10 minutes in a stream of argon gas. O-tert-butyldimethylsilyl 3-bromopropanol (22.4 g) was added to the reaction solution under ice-cooling, and the solution was stirred at room temperature for 15 hours. After water was added thereto, the solution was extracted with ethyl acetate. The extract was washed with water and saturated brine, and dried over sodium sulfate. The thus-obtained residue was purified by silica gel column chromatography (developing solvent, ethyl acetate:hexane=1:50) to obtain a crude produce (16 g) as a pale yellow oil.

Step 16) 3-(N,N-diphenylamino)propanol (XXII)

A tetrabutylammonium fluoride-tetrahydrofuran (1 ml/l, 30 ml) solution was added to a tetrahydrofuran (45 ml) solution of the crude product (5 g) obtained in the above Step 15) uncer ice-cooling, and the solution was stirred at room temperature for 2.5 hours. After water was added thereto, the solution was extracted with ethyl acetate. The extract was washed with saturated brine and dried over sodium sulfate. The thus-obtained residue was purified by silica gel column chromatography (developing solvent, ethyl acetate:hexane=1:4) to obtain a crude product (960 mg) as a pale blue oil.

Step 17) 3-(N,N-diphenylamino)propyl methanesulfonate (VIII)

Using the compound (950 mg) obtained in the above 16), a reaction was performed in the same manner as in Step 17) of Example 6. The thus-obtained residue was purified by silica gel column chromatography (developing solvent, ethyl acetate:hexane=1:3) to obtain a crude product (450 mg) as a colorless oil.

Step 4) 3-[1-[3-(N,N-diphenylamino)propyl]piperidin-4-yl]-3H-quinazolin-4-one (I)

Using the compound (450 mg) obtained in the above Step 17) and the compound (337 mg) obtained in Step 3) of Example 1, a reaction was performed in the same manner as in Step 4) of Example 6. The subsequent purification by silica gel column chromatography (developing solvent, ethyl acetate:triethylamine=80:1) produced the desired compound (510 mg; yield, 79%) as a white solid.

Step 13) Using the compound (500 mg) obtained in the above Step 4, a reaction was performed in the same manner as in Step 13) of Example 1 to obtain the desired compound (540 mg, quantitative) as a white solid.

EXAMPLES 11 to 22

Compounds listed in Tables 6 to 10 were obtained in the same manner as in Example 1, Example 6, and Example 7.

EXAMPLE 23

Synthesis of 3-[1-[2-[N-(3-chlorophenyl)-N-phenylamino]ethyl]-piperidin-4-yl]-3H-quinazolin-4-one Hydrochloride Step 15) 2-[N-(3-chlorophenyl)-N-phenylamine]ethyl acetate (XXI)

Using 3-chloro-N-phenylaniline (2.5 g) and 2-bromoethyl acetate (6.1 g), a reaction was performed in the same manner as in Step 15) of Example 6. The residue thus obtained was used for the next Step as it was.

Step 16) 2-[N-(3-chlorophenyl)-N-phenylamino]ethanol (XXII)

Using the crude product obtained in the above Step 15), a reaction was performed in the same manner as in Step 16) of Example 6. The thus-obtained residue was purified by silica gel column chromatography (developing solvent, ethyl acetate:hexane=1:8) to obtain the desired compound (847 mg); yield, 28%) as an orange oil.

Step 18) N-(2-bromoethyl)-N-phenyl-3-chloroaniline (VIII)

Triphenylphosphine (1.08 g) and carbon tetrachloride (1.36 g) were added to a dichloromethane (10 ml) solution of the compound (847 mg) obtained in the above step 16) under ice-cooling, and the solution was stirred at room temperature for 1 hour. The thus-obtained residue was purified by silica gel column chromatography (developing solvent, ethyl acetate:hexane =1:50) to obtain the desired compound (1.06 g, quantitative) as a green oil.

Step 4) 3-[1-[2-[N-(3-chlorophenyl)-N-phenylamino] ethyl]piperidin-4-yl]-3H-quinazolin-4-one (1)

An acetonitrile (6 ml) solution of the compound (746 mg) obtained in the above Step 18), the compound (459 mg) obtained in Step 3) of Example 1, and potassium carbonate (276 mg) was heated under reflux overnight. The reaction solution was concentrated, water was added thereto, and the solution was extracted with chloroform. The extract was washed with water and saturated brine, and dried over sodium sulfate. The thus-obtained residue was purified by silica gel column chromatography (developing solvent, ethyl acetate:hexane=1:1 to ethyl acetate) to obtain the desired compound (205 mg; yield, 22%) as a brown amorphous substance.

Step 13) Using the compound (205 mg) obtained in the above Step 4), the reaction was performed in the same manner as in Step 13) of Example 1 to obtain the desired compound (200 mg; yield, 90%) as a white powder.

EXAMPLE 24

Synthesis of 3-[1-[3-[N-phenyl-N-pyridin-3-yl-amino]propyl]-piperidin-4-yl]-3H-quinazolin-4-one dihydrochloride Step 15) N-(3-tert-butyldimethylsilyloxypropyl)-N-pyridin-3-yl-aniline (XXI)

Sodium hydride (1.2 g) was added to a dimethylsulfoxide (30 ml) solution of N-pyridin-3-ylaniline (2.55 g), and the solution was stirred at room temperature for 3 hours in a stream of argon gas. 3-Bromopropoxy-tert-butyldimetylsilane (4 ml) was added dropwise to the reaction solution, and the solution was stirred overnight. After chloroform, ice, and water were added thereto, the solution was extracted with chloroform. The extract was washed with saturated brine and dried over sodium sulfate. The thus-obtained residue was purified by silica gel column chromatography (developing solvent, ethyl acetate:hexane=1:10 to 1:3) to obtain the desired compound (4.04 g; yield, 79%) as an oil.

Step 16) 3-(N-phenyl-N-pyridin-3-yl-amino)propanol (XXII)

A tetrahydrofuran solution of tetra-n-butylammonium fluoride (1 mol/l, 23.6 ml) was added to a tetrahydrofuran (80 ml) solution of the compound (4.04 g) obtained in the above Step 15) under ice-cooling, and the solution was stirred at room temperature for 3 hours. After the reaction solution was concentrated under reduced pressure, water was added to the residue, and the solution was extracted with ethyl acetate. The extract was washed with saturated brine. 2N Hydrochloric acid (20 ml) and water was added too the organic phase. The aqueous phase was separated and washed with ethyl acetate. A 1N sodium hydroxide aqueous solution was added thereto, and the solution was extracted with ethyl acetate. The organic phase was washed with saturated brine, dried over sodium sulfate, and concentrated to obtain the desired compound (2.41 g; yield, 90%) as an oil.

Step 18) N-(3-chloropropyl)-N-pyridin-3-yl-aniline (VIII)

Thionyl chloride (1.5 ml) was added to a chloroform (30 ml) solution of the compound (2.34 g) obtained in the above Step 16), and the solution was heated under reflux for 1 hour in a stream of nitrogen gas. A cold sodium bicarbonate aqueous solution was added to the reaction solution, and the resulting mixture was extracted with chloroform. The extract was washed with saturated brine and dried over sodium sulfate. The thus-obtained residue was concentrated under reduced pressure to obtain the desired compound (2.47 g; yield, 98%) as oil.

Step 4) 3-[1-[3-(N-phenyl-N-pyridine-3-yl-amino) propyl]-piperidin-4-yl]-3H-quinazolin-4-one (I)

Using the compound (530 mg) obtained in the above Step 18) and the compound (500 mg) obtained in Step 3) of Example 1, a reaction was performed in the same manner as in Step 4) of Example 7. The thus-obtained residue was purified by silica gel column chromatography (developing solvent, chloroform:methanol=20:1) to obtain the desired compound (420 mg; yield, 44%).

Step 13) Using the compound (420 mg) to obtained in the above Step 4), the reaction was performed in the same manner as in Step 13) of Example 1 to obtain the desired compound (591 mg, quantitative) as a white powder.

EXAMPLES 25 TO 26

Compounds listed in Table 11 were obtained in the same manner as in Example 1, Example 6, or Example 23.

EXAMPLE 27

Synthesis of 3-[1-[2-(N-benzhydryl-N-benzyl-amino)ethyl]-piperidin-4-yl]-3H-quinazolin-4-one Step 19) N-benzhydryl-N-benzyl-acetoxyacetoamide (XXIV)

Acetoxyacetyl chloride (0.6 ml) was added to a chloroform (30 ml) solution of the compound (1.55 g) obtained in the above Production Example 12 under ice-cooling. Triethylamine (1.6 ml) was further added dropwise thereto. After the solution was stirred at room temperature for 0.5 hours, water was added thereto, and the reaction solution was concentrated under reduced pressure. Deposited crystals were collected by filtration and washed with water. The thus-obtained residue was recrystallized from ethyl acetate-hexane to obtain the desired compound (1.59 g; yield, 85%).

Step 20) 2-(N-benzhydryl-N-benzylamino)ethanol hydrochloride XXII)

An ether (20 ml)-tetrahydrofuran (80 ml) mixed solution containing the compound (1.29 g) obtained in the above Step 19) was added to an ether (20 ml) solution of lithium aluminum hydride (0.4 g) in a stream of argon gas, and the solution was heated under reflux for 0.5 hours. Under ice-cooling, water (0.4 ml), a 15% sodium hydroxide aqueous (0.4 ml) solution, and water (1.2 ml) were sequentially added to the reaction solution, and the solution was stirred at room temperature. Potassium carbonate was further added thereto, and the solution was stirred. After the solution was filtered with celite, the filtrate was washed with ethyl acetate, concentrated, and dried under reduced pressure to obtain a yellow oil (1.21 g). Water, concentrated sulfuric acid, and hexane were added to an ethyl acetate solution of this oil product (1.21 g). The deposited crystals were collected by filtration and washed with ethyl acetate to obtain the desired compound (893 mg; yield, 73%) as crystals.

Step 18) N-benzhydryl-N-benzyl-N-(2-chloroethyl)amine (VIII)

Methanesulfonyl chloride (0.4 ml) was added to a dichloromethane (10 ml) solution of the compound (842 mg) obtained in the above Step 20) and triethylamine (1.6 ml) under ice-cooling, and the solution was stirred at room temperature for 8.5 hours. The reaction solution was washed with saturated brine and dried over sodium sulfate. The thus-obtained residue was purified by silica gel column chromatography (developing solvent, ethyl acetate:hexane= 1:10) to obtain the desired compound (442 mg; yield, 55%) as an oil.

Step 4) A dimethylformamide (5 ml) solution of the compound (442 mg) obtained in the above Step 18), the compound (286 mg) obtained in Step 3) of Example 1, potassium carbonate (200 mg), and potassium iodide (one granule) was stirred at 85° C. for 19 hours under heating. After water was added to the reaction solution, the deposited solid was collected by filtration and washed with water. The thus-obtained residue was purified by silica gel column chromatography (developing solvent, ethyl acetate:hexane= 1:2 to 1:1). The resulting product was recrystallized from ethanol-water to obtain the desired compound (245 mg; yield, 37%) as colorless crystals.

EXAMPLE 28

Synthesis of 3-[1-[2-(N,N-dicyclohexylamino)ethyl] piperidin-4-yl]-3H-quinazolin-4-one dihydrochloride Step 19) N,N-dicyclohexylbenzyloxyacetamide (XXIV)

Benzyloxyacetyl chloride (3.72 ml) was added to a chloroform (10 ml) solution of N,N-dicyclohexylamine (2.14 g), and the solution was heated under reflux for 4.5 hours in a stream of argon gas. After the solution was allowed to cool to room temperature, water was added thereto, and the solution was extracted with ethyl acetate. The extract was washed with water and saturated brine, and dried over sodium sulfate. The thus-obtained residue was purified by silica gel column chromatography (developing solvent, ethyl acetate:hexane =1:5) to obtain the desired compound (2.09 g; yield, 54%) as a colorless, transparent oil.

Step 20) 2-(N,N-dicyclohexylamine)ethanol (XXII)

Lithium aluminum hydride (132 mg) was added to an ether (30 ml) solution of the compound (2.0 g) obtained in the above Step 19) in a stream of argon gas under ice-cooling. After the temperature was raised to room temperature, the solution was heated under reflux for 24 hours. The solution was allowed to cool to room temperature, water was added thereto, and the solution was made acidic with 2N hydrochloric acid. The solution was then made alkaline with 2N sodium hydroxide aqueous solution followed by extraction. The extract was washed with water and saturated brine, and dried over sodium sulfate. The thus-obtained residue was concentrated and dried to obtain a colorless transparent oil (1.76 g; yield, 92%). Raney nickel (50% slurry, 1 ml) was added to an argon-purged container and was dipped in methanol (10 ml). A methanol (20 ml) solution of the oil (1.7 g) obtained above was added to this solution, and catalytic reduction was conducted for 15 hours at 3 atmospheric pressure. After the reaction solution was filtered with celite, the thus-obtained residue was concentrated and dried to obtain the desired compound (956 mg; yield, 79%) as a pale yellow oil.

Step 18) N,N-dicyclohexyl-N-(2-chloroethyl)amine (VIII)

Triethylamine (706 μl) and methanesulfonyl chloride (392 μl) were added to a dichloromethane (20 ml) solution of the compound (950 mg) obtained in the above Step 20) in a stream of argon gas under ice-cooling, and the solution was stirred at room temperature. After water was added thereto, the reaction solution was washed with a sodium bicarbonate aqueous solution, water, and saturated brine, and dried over sodium sulfate. The thus-obtained residue was purified by silica gel column chromatography (developing solvent, ethyl acetate:hexane=1:10 to 1:1) to obtain the desired compound (390 mg; yield, 38%) as a pale yellow oil.

Step 4) 3-[1-[2-(N,N-dicyclohexylamino)ethyl]piperidin-4-yl]-3H-quinazolin-4-one (I)

An acetonitrile (4 ml) solution of the compound (390 mg) obtained in the above Step 18), the compound (367 mg) obtained in Step 3) of Example 1, potassium carbonate (442 mg), and sodium iodide (240 mg) was heated under reflux for 14 hours. The solution was allowed to cool to room temperature and extracted with water and ethyl acetate. The organic phase was washed with water and saturated brine, and dried over sodium sulfate. The thus-obtained residue was purified by silica gel column chromatography (developing solvent, chloroform:methanol=10:1) to obtain the desired compound (437 mg; yield, 63) as a white solid.

Step 13) Hydrogen chloride-ether (1M, 2.4 ml) was added to a chloroform (0.2 ml) solution of the compound (350 mg) obtained in the above Step 4) under ice-cooling, and the solution was stirred at room temperature for 0.5 hours. Deposited crystals were collected by filtration, washed with ether, and dried to the desired compound (290 mg; yield, 71%) as a white solid.

EXAMPLE 29

Synthesis of 3-[1-(2-carbazol-9-yl-ethyl)piperidin-4-yl]-3H-quinazolin-4-one

Step 21) N-(2-propenyl)carbazole (XXVI)

Carbazole (4 g) was dissolved in dimethylformamide (40 ml) in a stream of argon gas. Sodium hydride (1.05 g) was added thereto under ice-cooling, and the solution was stirred for 10 minutes. After the solution was stirred at room temperature for an additional 0.5 hours, a dimethylformamide (8 ml) solution of 3-bromo-1-propene (2.27 g) was added thereto under ice-cooling, and the solution was stirred at room temperature for 14 hours. Water was added to the reaction solution, and the solution was extracted with ethyl acetate. The extract was washed with water and saturated brine, and dried over sodium sulfate. After filtration, the filtration was allowed to stand. The deposited solid was collected by filtration and washed with hexane to obtain the desired compound (5.3 g, quantitative) as a pale yellowish white solid.

Step 22) 9H-carbazole-9-acetaldehyde (XXVII)

Sodium periodate (6.08 g) and a 4% aqueous solution of osmium tetra oxide (1.56 ml) were added to a tetrahydrofuran (80 ml)-water (40 ml) mixed solution containing the compound (4.95 g) obtained in the above Step 21) in a stream of argon gas, and the solution was stirred at room temperature for 14 hours. After the solution was extracted with ethyl acetate, the extract was washed with water and saturated brine, and dried over sodium sulfate. The thus-obtained residue was purified by silica gel column chromatography (developing solvent, ethyl acetate:hexane=1:3)to obtain the desired compound (407 mg; yield, 8%) as an orange solid.

Step 23) N-(2-hydroxyethyl)carbazole (XXII)

Sodium borohydride (72 mg) was added to a methanol (25 ml) solution of the compound (400 mg) obtained in the above Step 22) under ice-cooling, and the solution was stirred at room temperature for 2 hours. The reaction solution was concentrated, water was added thereto, and the solution was extracted with ethyl acetate. The extract was washed with water and saturated brine, and dried over sodium sulfate. The thus-obtained residue was purified by silica gel column chromatography (developing solvent, ethyl acetate:hexane =1:3) to obtain the desired compound (368 mg; yield, 91%) as a pale yellow solid.

Step 17) 2-(9H-carbazol-9-yl)ethyl methanesulfonate (VIII)

Triethylamine (284 ml) and methanesulfonyl chloride (158 ml) were added to a dichloromethane solution of the compound (360 mg) obtained in the above Step 23) under ice-cooling, and the solution was stirred for 1.5 hours. After water was added to the reaction solution, it was washed sequentially with a sodium bicarbonate aqueous solution, water, and saturated brine, and dried over sodium sulfate. The thus-obtained residue was purified by silica gel column chromatography (developing solvent, ethyl acetate:hexane=1:2) to obtain the desired compound (448 mg; yield, 91% ) as a white solid.

Step 4) An acetonitrile (7 ml) solution of the compound (400 mg) obtained in the above Step 17), the compound (316 mg) obtained in Step 3) of Example 1, and potassium carbonate (381 mg) was heated under reflux for 38 hours in a stream of argon gas. After the solution was allowed to cool to room temperature, water was added thereto, and the solution was extracted with ethyl acetate. The extract was washed with water and saturated brine, and dried over sodium sulfate. The thus-obtained residue was purified by silica gel column chromatography (developing solvent, ethyl acetate) to obtain the desired compound (200 mg; yield, 34%) as a white solid.

EXAMPLE 30

Synthesis of 3-[1-[2-(N-benzhydryl-N-methylamino)ethyl]-piperidin-4-yl]-3H-quinazolin-4-one dihydrochloride Step 24) N-benzhydryl-acetoxyacetamide (XXV-1)

Acetoxyacetyl chloride (10 ml) was added to a dichloromethane (100 ml) solution of benzhydrylamine (17.04 g) and triethylamine (14.26 ml) under ice-cooling, and the solution was stirred for 0.5 hours. After water was added to the reaction solution, the solution was extracted with chloroform. The extract was washed sequentially with 1N hydrochloric acid, water, a saturated sodium bicarbonate aqueous solution, water, and saturated brine, and dried over sodium sulfate. The thus-obtained residue was concentrated and dried under reduced pressure to obtain the desired compound (26.53 g, quantitative) as a white solid.

Step 25) 2-benzhydrylamine-ethanol (XXIII-1)

The compound (5.0 g) obtained in the above Step 24) was added to a tetrahydrofuran anhydride (100 ml) solution of lithium aluminum hydride (2.0 g) under ice-cooling in a stream of argon gas, and the solution was heated under reflux for 2 hours. Water (2 ml), a 15% sodium hydroxide aqueous (2 ml) solution, and water (6 ml) were added to the reaction solution in this order under ice-cooling, and the solution was stirred at room temperature. After potassium carbonate was added thereto, the solution was further stirred then filtered with celite. The filtrate was washed with ethyl acetate, concentrated, and dried under reduced pressure to obtain the desired compound (4.08 g, quantitative) as a yellow oil.

Step 26) 2-(N-formyl-N-benzhydrylamino)ethanol (XXIX)

An ethyl formate (1 ml) solution of the compound (1.0 g) obtained in the above Step 25) was stirred overnight under heating. The reaction solution was concentration and subjected to azeotropic distillation after adding toluene. The residue was dried under reduced pressure to obtain the desired compound (1.13 g, quantitative) as a yellow oil.

Step 27) 2-(N-benzhydryl-N-methylamino)ethanol (XXIII-2)

Lithium aluminum hydride (235 mg) was added three times to a tetrahydrofuran anhydride (10 ml) solution of the compound (528 mg) obtained in the above Step 26) in a stream of argon gas, and the solution was heated under reflux for 2 hours. Under ice-cooling, water (0.75 ml), a 15% sodium hydroxide aqueous (0.75 ml) solution, and water (2.25 ml) were sequentially added to the reaction solution, and the solution was stirred at room temperature for 0.5 hours. After potassium carbonate (3 g) was added thereto, the solution was stirred, filtered with celite, and washed with chloroform. The thus-obtained residue was purified by silica gel column chromatography (developing solvent, ethyl acetate:hexane=1:2) to obtain the desired compound (405 mg; yield, 81%) as a colorless oil.

Step 18) N-benzhydryl-N-methyl-2-bromoethylene (VIII)

Using the compound (780 mg) obtained in the above Step 27), the reaction was performed in the same manner as in Step 18) of Example 23. The thus-obtained residue was purified by silica gel column chromatography (developing solvent, ethyl acetate:hexane=1:50) to obtain the desired compound (694 mg; yield, 71%) as a colorless oil.

Step 4) 3-[1-[2-(N-benzhydride-N-methylamino)ethyl] piperidin-4-yl]-3H-quinazolin-4-one (I)

Using the compound (694 mg) obtained in the above Step 18) and the compound (523 mg) obtained in Step 4) of Example 23. The thus-obtained residue was purified by silica gel column chromatography (developing solvent, chloroform:methanol=50:1), then recrystallized from hexane-ethyl acetate to obtain the desired compound (605 mg; yield, 59%) as a white solid.

Step 13) Using the compound (605 mg) obtained in the above Step 4), a reaction was performed in the same manner as in Step 13) of Example 1. The desired compound (702 mg, quantitative) was obtained as a white powder.

EXAMPLE 31

Synthesis of 3-[1-[2-(N,N-benzylamino)ethyl] piperidin-4-yl]-3H-quinazolin-4-one Step 28) N,N-dibenzyl-2-tert-butyldimethylsilyloxyethylamine (XXII-2)

A dimethylformamide (40 ml) solution of the compound (5.3 g) obtained in Production Example 13, benzylbromide (2.36 ml), and potassium carbonate (4.1 g) was stirred at 140° C. for 15 hours in a stream of argon gas. After the reaction solution was allowed to cool, water (400 ml) was added thereto, and the solution was extracted with ethyl acetate. The extract was washed with water and saturated brine, and dried over sodium sulfate. The thus-obtained residue was purified by silica gel column chromatography (developing solvent, ethyl acetate:hexane=1:10) to obtain the desired compound (5.1 g; yield, 72%) as a colorless, transparent oil.

Step 16) 2-(N,N-dibenzylamino)ethanol (XXIII)

A tetrahydrofuran (21.4 ml) solution of tetrabutylammonium fluoride (1 M) was added to a tetrahydrofuran (50 ml) solution of the compound (5 g) obtained in the above Step 28) at 0° C., and the solution was stirred at room temperature for 1 hour. After a saturated ammonium chloride aqueous (50 ml) solution was added to the reaction solution, the solution was extracted with ethyl acetate. The extract was washed with water and saturated brine, and dried over sodium sulfate. The thus-obtained residue was purified by silica gel column chromatography (developing solvent, ethyl acetate:hexane=1:3) to obtain the desired compound (3.96 g, quantitative) as a colorless oil.

Step 18-N,N-dibenzyl-2-bromoethylamine (VIII)

Triphenylphosphine (3.75 g) was added to a dichloromethane (70 ml) solution of the compound (3.96 g) obtained in the above Step 16) and carbon tetrabromide (5.22 g), and the solution was stirred at room temperature for 14 hours in a stream of argon gas. The reaction solution was concentrated, and the thus-obtained residue was purified by silica gel column chromatography (developing solvent, ethyl acetate:hexane=1:30) to obtain the desired compound (1.95 g; yield, 45%) as a pale yellow oil.

Step 4) Using the compound (332 mg) obtained in the above Step 18), a reaction was performed in the same manner as in Step 4) of Example 23 to obtain the desired compound (410 mg; yield, 83%) as a white solid.

EXAMPLE 32

Synthesis of 3-[2-(N-benzoyl-N-phenylamino)ethyl] piperidin-4-yl ]-3H-quinazolin-4-one hydrochloride Step 28) N-benzoyl-N-phenyl-2-tert-butyldimethyl silyloxyethylamine (XXII-2)

Benzoyl chloride (693 μl) was added to a dichloromethane (30 ml) solution of N-phenyl-2-tert-butyldimethylsilyloxy-ethylamine (1.5 g) and triethylamine (832 μl) under ice-cooling in a stream of argon gas, and the solution was stirred at room temperature for 1 hour. After water was added to the reaction solution, the solution was extracted with chloroform. The extract was washed with water and saturated brine, and dried over sodium sulfate. The thus-obtained residue was concentrated and dried to obtain the desired compound (2.20 g, quantitative) as a yellow oil.

Step 16) 2-(N-benzoyl-N-phenylamino)ethanol (XXXIII)

A tetrahydrofuran (2 ml) solution of tetrabutylammonium fluoride (1 M) was added to a tetrahydrofuran (20 ml) solution of the compound (2.2 g) obtained in the above Step 28) under ice-cooling, and the solution was stirred at room temperature for 1.5 hours. After the reaction solution was concentrated under reduced pressure, water was added thereto, and the solution was extracted with chloroform. The extract was washed with water and saturated brine, and dried over sodium sulfate. The thus-obtained residue was purified by silica gel column chromatography (developing solvent, ethyl acetate: hexane =1:1 to 2:1) to obtain the desired compound (1.35 g; yield, 94%) as a pale yellow oil.

Step 18) N-benzoyl-N-phenyl-2-chloroethylamine (VIII)

Using the compound obtained in the above Step 16), a reaction was performed in the same manner as in Step 17) of Example 6. The thus-obtained residue was purified by silica gel column chromatography (developing solvent, ethyl acetate: hexane=1:1 to 2:1) to obtain the desired compound (490 mg; yield, 54%) as a pale yellow oil.

Step 4) 3-[1-[2-(N-benzoyl-N-phenyl-amino)ethyl] piperidin-4-yl]-3H-quinazolin-4-one (I)

Using the compound (490 mg) obtained in the above Step 18) and the compound (433 mg) obtained in Step 3) of Example 1, a reaction was performed in the same manner as in Step 4) of Example 6. The thus-obtained residue was purified by silica gel column chromatography (developing solvent, chloroform: methanol=10:1) to obtain the desired compound (260 mg; yield, 30%) as a white solid. Step 13) Using the compound (255 mg) obtained in the above Step 4), a reaction was performed in the same manner as in Step 13) of Example 1. The resulting product was recrystallized from ethanol to obtain the desired compound (63 mg; yield, 23%) as a white solid.

EXAMPLE 33

Synthesis of 3-[1-[2-[N-(4-chlorophenyl)-N-pyridin-2-ylamino]-ethyl]piperidin-4-yl]-3H-quinazolin-4-one dihydrochloride Step 5) 1-Benzyl-4-tert-butoxycarbonylaminopiperidine (X)

A dichloromethane solvent of pivalic anhydride (63 g) was added to a dichloromethane (450 ml) solution of 1-benzyl-4-aminopiperidine (50 g) under ice-cooling, and the solution was stirred overnight at room temperature. The reaction solution was then concentrated and recrystallized from ether to obtain the desired compound (69 g; yield, 91%) as white crystals.

Step 6) 4-tert-butoxycarbonylaminopiperidine (XI)

Acetic acid (4 ml) was added to an ethanol (80 ml) solution of the compound (10 g) obtained in the above Step 5). 10% Palladium-on-carbon (1 g) was added thereto under an argon atmosphere. The solution was stirred at room temperature for 4 hours while hydrogen gas was blown into it at 2.8 atmospheric pressure. The reaction solution was filtered with celite, and the filtrate was concentrated. The concentrate was then subjected to azeotropic distillation after adding toluene. The thus-obtained residue was dissolved in chloroform and washed with a mixed solution of a 3N potassium hydroxide aqueous solution and brine. The aqueous phase was further extracted with chloroform. The resulting organic phase was dried over sodium sulfate and concentrated to obtain the desired compound (6.9 g, quantitative) as a white solid.

Step 7) 1-(2-Bromoethyl)-4-tert-butoxycarbonylaminopiperidine (XIII)

1,2-Dibromoethane (219 g) and potassium carbonate (16.1 g) were added to a tetrahydrofuran (400 ml) suspension of the compound (23.4 g) obtained in the above Step 6), and the solution was stirred at room temperature for 6 days. The reaction solution was then filtered, and the filtrate was concentrated. The thus-obtained residue was purified by silica gel column chromatography (developing solvent, ethyl acetate: hexane=1:3 to ethyl acetate) to obtain the desired compound (12.1 g; yield, 34%) as pale beige crystals.

Step 8) 4-tert-Butoxycarbonylamino-1-[2-[N-(4-chlorophenyl)-N-pyridine-2-yl-amino ]ethyl]piperazine (XV)

Sodium hydride (156 mg) was added to a dimethylsulfoxide anhydride (10 ml) solution of 4-chloro-N-pyridine- 2-aniline (800 mg) obtained in Production Example 14, and the solution was stirred at room temperature for 0.5 hours in a stream of argon gas. The compound (600 mg) obtained in the above Step 7) was added to the reaction solution, and the solution was stirred at room temperature for 2 hours in a stream of argon gas. Water was then added to the reaction solution, and the solution was extracted with ethyl acetate. The extract was washed with water and saturated brine, and dried over sodium sulfate. The residue thus obtained was purified by silica gel column chromatography (developing solvent, ethyl acetate: hexane=2:1 to ethyl acetate) to obtain the desired compound (680 mg; yield, 81%) as a pale yellow amorphous substance.

Step 9) 4-amino-1-[2-[N-(4-chlorophenyl)-N-pyridin-2-yl-amino]ethyl]piperidine (XVI)

Trifuoroacetic acid (6 ml) was added to a dichloromethane (6 ml) solution of the compound (680 mg) obtained in the above Step 8) under ice-cooling, and the solution was stirred at room temperature for 20 minutes. The reaction solution was concentrated and subjected to azeotropic distillation after adding toluene. After a 10% potassium carbonate aqueous solution was added to the residue, the solution was extracted with a mixed solvent of chloroform and tetrahydrofuran (10:1). The extract was washed with saturated brine and dried over sodium sulfate. The thus-obtained residue was concentrated under reduced pressure to obtain the desired compound (516 mg; yield, 99%) as a yellow oil.

Step 10) 2-amino-N-[1-[2-[N-(4-chlorophenyl)-N-pyridine-2-amino]ethyl]piperidin-4-yl]benzamide (XVIII)

1-Ethyl-3-(3-dimethylaminopropyl)carbodiimide hydrochloride (297 mg) was added to a dimethylformamide (5 ml) solution of anthranilic acid (213 mg), the compound (513 mg) obtained in the above Step 9), and 1-hydroxybenzotriazole (209 mg) under ice-cooling, and the solution was stirred at room temperature for 5 hours. After a 10% potassium carbonate aqueous solution was added to the reaction solution, the solution was extracted with chloroform. The extract was washed with saturated brine and dried over sodium sulfate. The thus-obtained residue was purified by silica gel column chromatography (developing solvent, ethyl acetate) to obtain the desired compound (670 mg; yield, 96%) as a pale yellow amorphous substance.

Step 11) 3-[1-[2-[N-(4-chlorophenyl)-N-pyridin-2-ylamino]ethyl]-piperidin-4-yl]-3 H-quinazolin-4-one (I)

A formic acid (10 ml) solution of the compound (670 mg) obtained in the above Step 10) was heated under reflux overnight. The reaction solution was concentrated and subjected to azeotropic distillation after adding toluene. After a 10% potassium carbonate aqueous solution was added to the residue, the solution was extracted with chloroform. The extract was washed with saturated brine and dried over sodium sulfate. The thus-obtained residue was recrystallized from ethyl acetate to obtain the desired compound (498 mg; yield, 73%) as a white solid.

Step 13) 4N Hydrogen chloride-ethyl acetate (1 ml) was added to a dichloromethane (5 ml) solution of the compound (494 mg) obtained in the above Step 11), and the solution was stirred at room temperature for 0.5 hours. Deposited crystals were collected by filtration, washed with ethyl acetate, and dried at 50° C. under reduced pressure to obtain the desired compound (572 mg, quantitative) as a white powder.

EXAMPLE 34

Synthesis of 3-[1-[2-(10,11-dihydro-5H-dibenzo[b,f]azepin-5-yl) ethyl]piperidin-4-yl]-3H-quinazolin-4-one Step 8) 4-tert-butoxycarbonylamino-1-[2-(10,11-dihydro-5H-dibenzo [b,f]azepin-5-yl)ethyl]piperidine (XV)

Sodium hydride (104 mg) was added to a dimethylsulfoxide anhydride (8 ml) solution of 10,11-dihydro-5H-dibenzo[b,f]azepine (508 mg) at room temperature in a stream of argon gas, and the solution was stirred for 0.5 hours. The compound (400 mg) obtained in Step 7) of Example 33 was added to the reaction solution, and the solution was stirred at room temperature for 1.5 hours. Water was then added to the reaction solution, and the solution was extracted with ethyl acetate. The extract was washed with water and saturated brine, and dried over sodium sulfate. The thus-obtained residue was purified by silica gel column chromatography (developing solvent, ethyl acetate: hexane=1:1) to obtain the desired compound (75 mg; yield, 11%) as a pale pink amorphous substance.

Step 9) 4-Amino-1-[2-(10,11-dihydro-5H-dibenzo[b,f]azepin-5-yl) ethyl]piperidine (XVI)

Trifuloroacetic acid (420 μl) was added to a dichloromethane (0.5 ml) solution of the compound (75 mg) obtained in the above Step 8), and the solution was stirred at room temperature for 2 hours. After the reaction solution was concentrated, toluene (0.5 ml) was added thereto to conduct azeotropic distillation. 10% potassium carbonate (2 ml) was added to the residue, and the solution was extracted with a mixed solvent of chloroform and tetrahydrofuran (9:1) (2 ml). The extract was dried over sodium sulfate. The resulting residue was concentrated under reduced pressure and dried to obtain the desired compound (60 mg, quantitative) as a pale brown oil.

Step 10) 2-amino-N-[1-[2-(10,11-dihydro-5H-dibenzo[b,f]azepin-5-yl) ethyl]piperidin-4-yl]benzamide (XVIII)

1-Ethyl-3-(3-dimethylaminopropyl)carbodiimide hydrochloride (35 mg) was added to a dimethylformamide (1 ml) solution of anthranilic acid (25 mg), the compound (58 mg) obtained in the above Step 9), and 1-hydroxybenzotriazole (24 mg), and the solution was stirred at room temperature for 14 hours. After 10% potassium sodium carbonate (5 ml) was added to the reaction solution, the solution was extracted with a mixed solvent of chloroform and tetrahydrofuran (9:1) (5 ml). The extract was concentrated uder reduced pressure and subjected to azeotropic distillation after adding xylene. The thus-obtained residue was purified by silica gel column chromatography (developing solvent, chloroform: methanol=20:1) to obtain the desired compound (77 mg; yield, 97%) as a pale red amorphous substance.

Step 11) A formic acid (2 ml) solution of the compound (77 mg) obtained in the above Step 10) was heated under reflux for 14 hours. The solution was allowed to cool, concentrated under reduced pressure, and subjected to azeotropic distillation after adding toluene. After a 10% sodium bicarbonate aqueous solution was added to the residue, the solution was extracted with chloroform. The extract was washed with water and saturated brine, and dried over sodium sulfate. The thus-obtained residue was purified byi silica gel column chromatography (developing solvent, chloroform: methanol=20:1) to obtain the desired compound (57 mg; yield, 74%) as a white amorphous substance.

EXAMPLE 35

Synthesis of 3-[1-[2-(10,11-dihydro-5H-dibenzo[b,f]azepin-5-yl) ethyl]piperidin-4-yl]-3H-quinazolin-4-one hydrochloride Step 13) 4N Hydrogen chloride-ethyl acetate (0.33 ml) was added to a dichloromethane (0.2 ml) solution of the compound (57 mg) obtained in Step 11) of Example 34, and the solution was stirred for 0.5 hours. The deposited solid was collected by filtration, washed with ethyl acetate, and dried to obtain the desired compound (59 mg; yield, 94%) as a white solid.

EXAMPLE 36

Synthesis of 3-[1-[2-(5,11-dihydro-dibenzo[b,e][1,4] oxazepin-5-yl) ethyl]piperidin-4-yl]-3H-quinazolin-4-one Step 8) 4-tert-butoxycarbonylamino-1-[2-(5,11-dihydrodienzo[b,e][1,4]oxazepin-5-yl)ethyl]piperidine (XV)

Sodium hydride (130 mg) was added to a dimethylsulfoxide anhydride (10 ml) solution of 5,11-dihydro-dibenzo [b,e][1,4]-oxazepine (642 mg) obtained in Production Example 15 in a stream of argon gas, and the solution was stirred at room temperature for 0.5 hours. The compound (500 mg) obtained in Step 7) of Example 33 was added to the reaction solution, and the solution was stirred at room temperature for 1.5 hours. After water was added to the solution, it was extracted with ethyl acetate. The extract was washed with water and saturated brine, and dried over sodium sulfate. The thus-obtained residue was purified by silica gel column chromatography (developing solvent, ethyl acetate: hexane=3:1 to ethyl acetate) to obtain the desired compound (324 mg; yield, 47%) as a brown solid.

Step 9) 4-amino-1-[2-(5,11-dihydrodibenzo[b,e][1,4] oxazepin-5-yl) ethyl]piperidine (XVI)

Trifluoroacetic acid (3.5 ml) was added to a dichloromethane (3.5 ml) solution of the compound (321 mg) obtained in the above Step 8), and the solution was stirred for 0.5 hours at room temperature. After the reaction solution was concentrated, it was subjected to azeotropic distillation after adding toluene. A 10% potassium carbonate aqueous solution was added to the residue, and the solution was extracted with chloroform. The extract was washed with saturated brine and dried over sodium sulfate. The thus-obtained residue was concentrated under reduced pressure to obtain the desired compound (245 mg, quantitative) as a yellow oil.

Step 10) 2-amino-N-[1-[2-(5,11-dihydrodibenzo[b,e][1, 4]-oxazepin-5-yl) ethyl]piperidin-4-yl]benzamide (XVIII)

1-Hydroxybenzotriazole (115 mg) and 1-ethyl-3-(3-dimethylaminopropyl) carbodiimide hydrochloride (162 mg) were added to a dimethylformamide (5 ml) solution containing anthranilic acid (106 mg) and the compound (249 mg) obtained in the above Step 9) under ice-cooling, and the solution was stirred overnight at room temperature. A 10% potassium carbonate aqueous solution was added thereto, and the solution was extracted with a mixed solvent of chloroform and tetrahydrofuran (10:1). The extract was washed with water and saturated brine, and dried over sodium sulfate. The thus-obtained residue was purified by silica gel column chromatography (developing solvent, ethyl acetate: hexane=2:1 to ethyl acetate) to obtain the desired compound (343 mg, quantitative) as a brown solid.

Step 11) A formic acid (10 ml) solution of the compound (338 mg) obtained in the above Step 10) was heated uder reflux overnight. The solution was then concentrated and subjected to azeotropic distillation after adding toluene. After a 10% potassium carbonate aqueous solution was added to the residue, the solution was extracted with chloroform. The extract was washed with water and saturated brine, and dried over sodium sulfate. The thus-obtained residue was purified by silica gel column chromatography (developing solvent, ethyl acetate: hexane=1:1 to ethyl acetate) to obtain the desired compound (192 mg; yield, 55%) as a pale yellow solid.

EXAMPLE 37

Synthesis of 3-[1-[2-[N-(3,5-dimethylphenyl)-N-pyridin-2-yl-amino]ethyl]piperidin-4-yl]-3H-quinazolin-4-one dihydrochloride Step 8) 4-tert-butoxylamino-1-[2-[N-(3,5-dimethylphenyl)-N-pyridine-2-ylamino]ethyl]piperidine (XV)

Sodium hydride (78 mg) was added to a dimethylsulfoxide anhydride (8 ml) solution of 3,5-dimethyl-N-pyridin-2-ylaniline (773 mg) obtained in Production Example 16 at room temperature in a stream of argon gas, and the solution was stirred for 0.5 hours. The compound (600 mg) obtained in Step 7) of Example 33 was added to the reaction solution, and the solution was stirred for 2 hours. After water was added thereto, the solution was extracted with ethyl acetate. The extract was washed with water and saturated brine, and dried over sodium sulfate. The thus-obtained residue was purified by silica gel column chromatography (developing solvent, ethyl acetate: hexane =2:1 to ethyl acetate) to obtain the desired compound (490 mg; yield, 59%) as a white amorphous substance.

Step 9) 4-amino-1-[2-[N-(3,5-dimethylphenyl)-N-pyridin-2-yl-amino]ethyl]piperidine (XVI)

Trifluoroacetic acid (2.5 ml) was added to a dichloromethane (2.5 ml) solution of the compound (480 mg) obtained in the above Step 8), and the solution was stirred for 1 hour at room temperature. After the solution was concentrated uder reduced pressure, toluene was added thereto to conduct azeotropic distillation. A 10% potassium carbonate aqueous solution was added to the residue, and the solution was extracted with a mixed solvent of chloroform and tetrahydrofuran (10:1). The extract was dried over potassium carbonate and filtered. The filtrate was concentrated under reduced pressure and dried to obtain the desired compound (320 mg; yield, 87%) as a pale yellow oil.

Step 10) 2-Amino-N-[1-[2-[N-(3,5-dimethylphenyl)-N-pyridin-2-yl-amino]ethyl]piperidin-4-yl]benzamide (XVIII)

1-Ethyl-3-(3-dimethylaminopropyl)carbodiimide hydrochloride was added to a dimethylformamide (2 ml) solution containing anthranilic acid (133 mg), the compound (315 mg) obtained in the above Step 9), and 1-hydroxybenzotriazole hydrate (131 mg) under ice-cooling, and the solution was stirred at room temperature for 15 hours. A 10% potassium carbonate aqueous solution was added thereto, and the solution was extracted with a mixed solvent of chloroform and tetrahydrofuran (9:1). After the extract was concentrated under reduced pressure, xylene was added thereto to perform azeotropic distillation. The thus-obtained residue was purified by silica gel column chromatography (developing solvent, chloroform: methanol=10:1) to obtain the desired compound (315 mg; yield, 73%) as a white amorphous substance.

Step 11) 3-[1-[2-[N-(3,5-dimethylphenyl)-N-pyridine-2-yl-amino]-ethyl]piperidin-4-yl]-3H-quinazolin-4-one (I)

A formic acid (3 ml) solution of the compound (310 mg) obtained in the above Step 10) was heated under reflux for 40 hours. After the solution was allowed to cool to room temperature, toluene was added thereto to conduct azeotropic distillation. A sodium bicarbonate aqueous solution was added to the reaction solution, and it was extracted with chloroform. The extract was washed with saturated brine and dried over sodium sulfate. The thus-obtained residue was purified by silica gel column chromatography (developing solvent, chloroform:methanol=20:1) to obtain the desired compound (272 mg; yield, 86%) as a white amorphous substance.

Step 13) Using the compound (265 mg) obtained in the above Step 11), a reaction was performed in the same manner as in Step 13) of Example 33 to obtain the desired compound (280 mg; yield, 92%) as a white solid.

EXAMPLES 38 to 71

Compounds listed in Tables 15–26 were obtained as in Example 33.

EXAMPLE 72

Synthesis of 3-[1-[2-[N-(2-propylphenyl)-N-pyridin-2-ylamino]ethyl]piperidin-4-yl]-3H-quinazolin-4-one Step 8) 4-tert-Butoxycarbonylamino-1-[2-[N-(2-propylphenyl)-N-pyridin-2-yl-amino]ethyl]piperidine (XV)

Using the compound (509 mg) obtained in Step 7) of Example 33 and 2-propyl-N-pyridin-2-yl-aniline (691 mg) obtained in Production Example 41, a reaction was performed in the same manner as in Step 8) of Example 33. The thus-obtained residue was purified by silica gel column chromatography (developing solvent, ethyl acetate: hexane =3:1 to ethyl acetate) to obtain the desired compound (453 mg; yield, 62%) as a pale yellow oil.

Step 9) 4-Amino-1-[2-[N-(2-propylphenyl)-N-pyridine-2-ylamino]ethyl]piperidine (XVII)

Using the compound (453 mg) obtained in the above Step 8), a reaction was performed in the same manner as in Step 9) of Example 33 to obtain a crude product (375 mg) as a pale yellow oil.

Step 12) 4H-3,1-Benzoxazin-4-one (169 mg) obtained in Production Example 43 was added to a toluene (5 ml) solution of the crude product (375 mg) obtained in the above Step 9), and the solution was stirred at room temperature for 15 minutes. After triethyl orthoformate (1 ml) was added thereto, the solution was heated under reflux for 2 hours. The reaction solution was then concentrated under reduced pressure and extracted with chloroform. The extract was washed with a sodium bicarbonate aqueous solution and saturated brine, and dried over sodium sulfate. The thus-obtained residue was purified by silica gel column chromatography (developing solvent, chloroform: methanol=100:1 to 100:3), and the resulting product was recrystallized from ethanol-water to obtain the desired compound (355 mg; yield, 73%) as colorless crystals.

EXAMPLES 73 and 74

Compounds listed in Table 27 were obtained as in Example 72.

EXAMPLE 75

Synthesis of 3-[1-[2-(10,11-dihydro-10-hydroxy-5H-dibenzo[b,f]-azepin-5-yl) ethyl]piperidin-4-yl]-3H-quinazolin-4-one Step 4) Using the compound obtained in Production Example 44 and the compound obtained in Step 3) of Example 1, a reaction was performed in the same manner as in Step 4) of Example 7 to obtain the desired compound (yield, 47%) as a white solid.

EXAMPLE 76

Synthesis of 3-[1-[2-(10,11-dihydro-2-hydroxy-5H-dibenzo[b,f]azepin-5-yl)ethyl]piperidin-4-yl]-3H-quinazolin-4-one To protect the hydroxyl group of the compound synthesized in Production Example 45, a hydroxyl-protective group was introduced first.

Sodium hydroxide (710 mg) was added to a dimethylformamide (40 ml) solution of the crude crystals (4.05 g) obtained in Production Example 45 under a nitrogen atmosphere and ice-cooling. Chloromethyl methyl ether (1.35 ml) was further added thereto, and the solution was stirred overnight at room temperature. After the solution was concentrated, water was added thereto, and the solution was extracted with ethyl acetate. The extract was washed with water and saturated brine, dried over anhydrous sodium sulfate, and filtered. After the filtrate was concentrated, the thus-obtained residue was purified by silica gel column chromatography (developing solvent, hexane: ethyl acetate= 5:1) to obtain N-(2-chloroethyl)-10,11-dihydro-2-methoxymethoxy-5H-dibenzo [b,f]azepine (4.64 g; yield, 99%) as a yellow oil.

Step 4) Using N-(2-chloroethyl)-10,11-dihydro-2-methoxymethoxy-5H-dibenzo [b,f]azepine obtained in the above step and the compound obtained in Step 3) of Example 1, a reaction was performed in the same manner as in Step 4) of Example 7 to obtain 3-[1-[2-(10,11-dihydro-2-methoxy-methoxy-5H-dibenzo [b,f]azepin-5-yl) ethyl] piperidin-4-yl]-3H-quinazolin-4-one (yield, 74%) as a white amorphous substance.

4N Hydrochloric acid-ethyl acetate (20 ml) was added to an ethyl acetate (20 ml) solution of the thus-obtained compound (2.00 g), and the solution was stirred at room temperature for 3 hours. After the solution was concentrated, the residue was dissolved by adding thereto a saturated sodium bicarbonate aqueous solution and a mixed solvent of chloroform and methanol (10:1) under heating. After the organic phase was extracted, the aqueous phase was extracted with chloroform, and the extract was added to the organic phase obtained above. The combined organic phase was washed with water and saturated brine, dried over anhydrous sodium sulfate, and filtered. After the filtrate was concentrated, the thus-obtained residue was purified by silica gel column chromatography (developing solvent, ethyl acetate to ethyl acetate:methanol=20:1) to obtain the desired compound (1.83 g, quantitative) as a white amorphous substance.

Compounds produced in Examples 1 to 76 are shown in Tables 3 to 28.

TABLE 3

| Example | Compound (Properties; yield from the final step) | $^1$H NMR ($\delta$) ppm | MS |
|---|---|---|---|
| 1 | 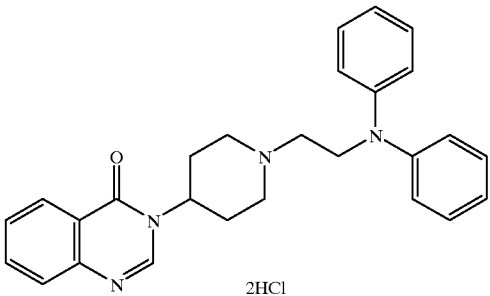<br>2HCl<br>(white crystals; 94%) | DMSO-$d_6$ 300 MHz<br>1.90–2.20(2H, m)<br>2.45–2.72(2H, m)<br>3.16–3.42(4H, m)<br>3.65–3.80(2H, m)<br>4.15–4.31(2H, m)<br>4.76–4.95(1H, m)<br>7.01(2H, t, J=7.3Hz)<br>7.02–7.15(4H, m)<br>7.26–7.38(4H, m)<br>7.53–7.62(1H, m)<br>7.69–7.76(1H, m)<br>7.82–7.91(1H, m)<br>8.18(1H, d, J=8.0Hz) | FAB$^+$ 425 |
| 2 | 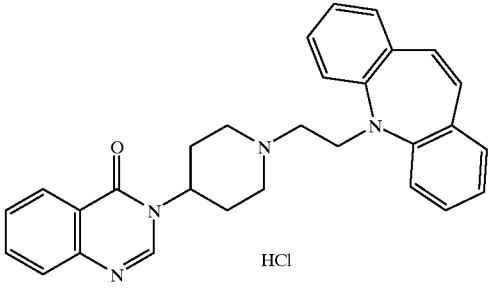<br>HCl<br>(pale yellow powder; 100%) | DMSO-$d_6$ 300 MHz<br>2.00–2.30(2H, m)<br>2.55–2.67(2H, m)<br>3.06–3.48(4H, m)<br>3.52–3.82(2H, m)<br>4.20–4.35(2H, m)<br>4.70–5.30(1H, m)<br>6.83(4H, s)<br>7.05–7.42(8H, m)<br>7.52–7.63(1H, m)<br>7.39(1H, d, J=6.8Hz)<br>7.80–7.90(1H, m)<br>8.18(1H, dd, J=8.0Hz, 1.2Hz)<br>8.33(1H, s) | FAB$^+$ 449 |
| 3 | 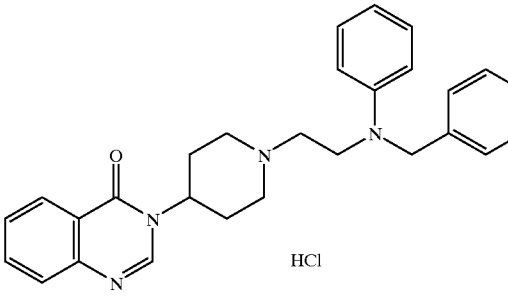<br>HCl<br>(colorless needle crystals; 89%) | DMSO-$d_6$ 300 MHz<br>2.03–2.20(2H, m)<br>2.42–2.57(2H, m)<br>3.15–3.44(4H, m)<br>3.64–3.80(2H, m)<br>3.83–3.99(2H, m)<br>4.63(2H, s)<br>4.77–4.92(1H, m)<br>6.66(1H, t, J=7.2Hz)<br>6.80(2H, d, J=8.1Hz)<br>7.10–7.39(7H, m)<br>7.58(1H, t, J=8.1Hz)<br>7.70(1H, d, J=7.8Hz)<br>7.80–7.92(1H, m)<br>8.18(1H, dd, J=8.1, 1.2Hz)<br>8.29(1H, s)<br>10.67(1H, brs) | FAB$^+$<br>439 |

TABLE 4

| Example | Compound (Properties; yield from the final step) | ¹H NMR (δ) ppm | MS |
|---|---|---|---|
| 4 | 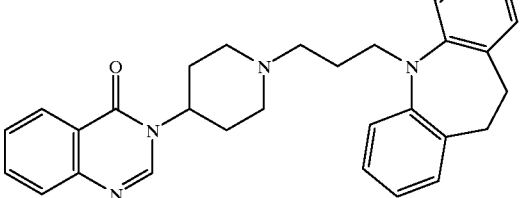<br>(white solid; 74%) | CDCl₃ 300 MHz<br>1.62–2.00(5H, m)<br>2.04–2.20(2H, m)<br>2.46(2H, t, J=7.5Hz)<br>2.92–3.06(2H, m)<br>3.17(4H, s)<br>3.79(2H, t, J=6.8Hz)<br>4.76–4.90(1H, m)<br>6.88–6.95(2H, m)<br>7.02–7.18(6H, m)<br>7.44–7.54(1H, m)<br>7.65–7.80(2H, m)<br>8.11(1H, s)<br>8.30(1H, dd, J=8.1Hz, 1.5Hz) | FAB⁺ 465 |
| 5 | 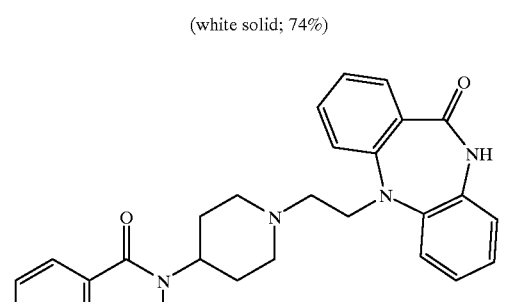<br>(white solid; 91%) | DMSO-d₆ 300 MHz<br>2.00–2.17(2H, m)<br>2.48–2.64(2H, m)<br>3.15–3.33(4H, m)<br>3.64–3.80(2H, m)<br>4.20–4.40(2H, m)<br>4.76–4.97(1H, m)<br>7.06–7.12(4H, m)<br>7.28–7.45(2H, m)<br>7.50–7.76(4H, m)<br>7.80–7.89(1H, m)<br>8.13–8.16(1H, m)<br>8.31(1H, s)<br>10.33(1H, s)<br>11.19(1H, brs) | FAB⁺ 466 |
| 6 | 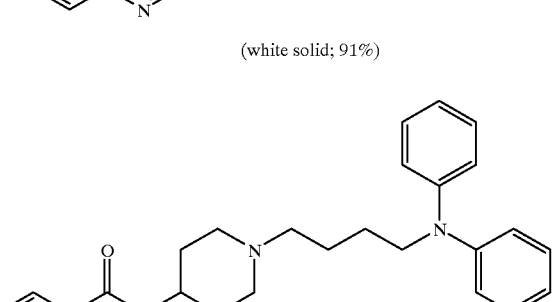<br>(white powder; 100%) | DMSO-d₆ 300 MHz<br>1.56–2.16(6H, m)<br>2.52–2.69(2H, m)<br>3.03–3.23(3H, m)<br>3.35–3.43(1H, m)<br>3.55–3.65(2H, m)<br>3.68–3.80(2H, m)<br>6.90–7.05(6H, m)<br>7.25–7.33(4H, m)<br>7.57–7.64(1H, m)<br>7.71–7.80(1H, m)<br>7.84–7.92(1H, m)<br>8.19(1H, dd, J=8.1Hz, 1.5Hz)<br>8.37(1H,s)<br>10.68(1H, brs) | FAB⁺ 453 |

TABLE 5

| Example | Compound (Properties; yield from the final step) | ¹H NMR (δ) ppm | MS |
|---|---|---|---|
| 7 | 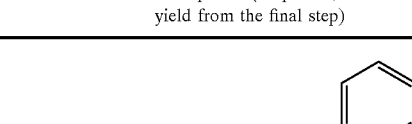<br>(white solid; 65%) | CDCl₃ 300 MHz<br>1.80–2.02(4H, m)<br>2.13(3H, s)<br>2.20–2.37(2H, m)<br>2.73(2H, t, J=7.2Hz)<br>3.04–3.12(2H, m)<br>3.80(2H, t, J=7.2Hz)<br>4.76–4.95(1H, m)<br>6.51(4H, d, J=8.1Hz)<br>6.70(1H, t, J=7.5Hz)<br>7.09–7.27(6H, m)<br>7.46–7.56(1H, m)<br>7.65–7.80(2H, m)<br>8.13(1H, s)<br>8.31(1H, dd, J=8.1Hz, 1.5Hz) | FAB⁺ 439 |

TABLE 5-continued

| Example | Compound (Properties; yield from the final step) | $^1$H NMR (δ) ppm | MS |
|---|---|---|---|
| 8 | 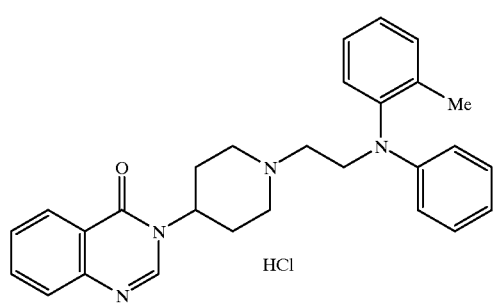<br>HCl<br>(white solid; 96%) | DMSO-$d_6$ 300 MHz<br>2.06(3H, s)<br>2.12(2H, brs)<br>2.35–2.65(2H, m)<br>3.15–3.75(5H, m)<br>3.70–3.80(2H, m)<br>4.00–4.15(2H, m)<br>4.75–4.90(1H, m)<br>6.56(2H, d, J=8.4Hz)<br>6.70(1H, t, J=7.3Hz)<br>7.10–7.42(6H, m)<br>7.57(1H, t, J=7.5Hz)<br>7.70(1H, d, J=8.4Hz)<br>7.85(1H, t, J=7.7Hz)<br>8.17(1H, d, J=7.0Hz)<br>8.29(1H, s)<br>10.95(1H, brs) | FAB$^+$<br>439 |
| 9 | 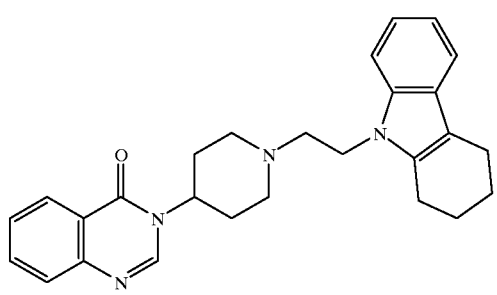<br>(white solid; 13%) | CDCl$_3$ 300 MHz<br>1.80–2.10(8H, m)<br>2.25–2.43(2H, m)<br>2.64–2.80(6H, m)<br>3.00–3.16(2H, m)<br>4.18(2H, t, J=7.2Hz)<br>4.80–4.94(1H, m)<br>7.00–7.10(2H, m)<br>7.20–7.32(1H, m)<br>7.40–7.55(2H, m)<br>7.63–7.80(2H, m)<br>8.15(1H, s)<br>8.31(1H, dd, J=8.1Hz, 1.2Hz) | FAB$^+$<br>427 |

TABLE 6

| Example | Compound (Properties; yield from the final step) | $^1$H NMR (δ) ppm | MS |
|---|---|---|---|
| 10 | 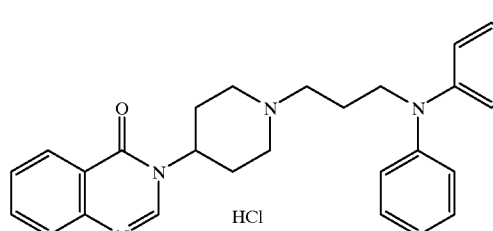<br>HCl<br>(white solid; 100%) | DMSO-d6 300 MHz<br>1.92–2.15(4H, m)<br>2.48–2.52(2H, m)<br>3.06–3.27(4H, m)<br>3.52–3.67(2H, m)<br>3.78(2H, t, J=7.2Hz)<br>4.82–4.97(1H, m)<br>6.95–7.07(6H, m)<br>7.24–7.38(4H, m)<br>7.52–7.64(1H, m)<br>7.68–7.78(1H, m)<br>7.82–7.92(1H, m)<br>8.12–8.22(1H, m)<br>8.32(1H, s)<br>10.68(1H, brs) | FAB$^+$ 439 |

TABLE 6-continued

| Example | Compound (Properties; yield from the final step) | $^1$H NMR ($\delta$) ppm | MS |
|---|---|---|---|
| 11 | 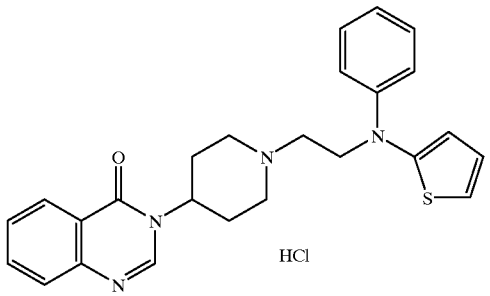<br>(pale purple solid; 100%) | DMSO-$d_6$ 300MHz<br>1.90–2.22(2H, m)<br>2.46–2.70(2H, m)<br>3.20–3.45(4H, m)<br>3.60–3.90(2H, m)<br>4.08–4.25(2H, m)<br>4.74–5.00(1H, m)<br>6.87–6.96(2H, m)<br>6.96–7.05(3H, m)<br>7.21–7.32(2H, m)<br>7.58(1H, t, J=7.2Hz)<br>7.71(1H, d, J=8.1Hz)<br>7.81–7.91(1H, m)<br>8.14–8.22(1H, m)<br>8.30(1H, brs)<br>11.03(1H, brs) | FAB$^+$ 431 |
| 12 | 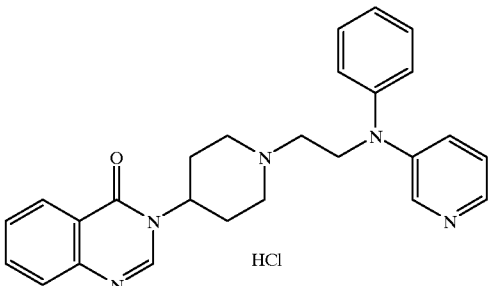<br>(pale yellow solid; 88%) | DMSO-$d_6$ 300 MHz<br>1.94–2.25(2H, m)<br>2.45–2.80(2H, m)<br>3.15–3.60(4H, m)<br>3.62–3.85(2H, m)<br>4.25–4.50(2H, m)<br>4.76–5.00(1H, m)<br>7.38–7.52(3H, m)<br>7.55–7.65(3H, m)<br>7.72(1H, d, J=8.1Hz)<br>7.77–7.94(3H, m)<br>8.18(1H, d, J=7.8Hz)<br>8.25(1H, d, J=5.1Hz)<br>8.32(1H, s)<br>8.40–8.46(1H, m)<br>11.60(1H, brs) | FAB$^+$ 426 |

TABLE 7

| Example | Compound (Properties; yield from the final step) | $^1$H NMR ($\delta$) ppm | MS |
|---|---|---|---|
| 13 | 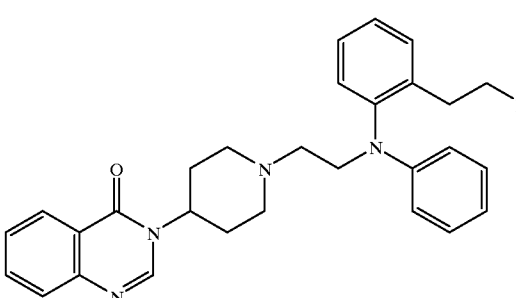<br>(white solid; 42%) | CDCl$_3$ 300 MHz<br>0.88(3H, t, J=7.1Hz)<br>1.50–1.68(2H, m)<br>1.86–2.05(4H, m)<br>2.22–2.38(2H, m)<br>2.46(2H, t, J=7.9Hz)<br>2.75(2H, t, J=7.7Hz)<br>3.03–3.14(2H, m)<br>3.76(2H, t, J=7.7Hz)<br>4.80–4.95(1H, m)<br>6.51(2H, d, J=7.7Hz)<br>6.69(1H, t, J=7.3Hz)<br>7.12–7.38(6H, m)<br>7.47–7.53(1H, m)<br>7.68–7.79(2H, m)<br>8.14(1H, s)<br>8.31(1H, d, J=8.1Hz) | FAB$^+$ 467 |

TABLE 7-continued

| Example | Compound (Properties; yield from the final step) | $^1$H NMR ($\delta$) ppm | MS |
|---|---|---|---|
| 14 | 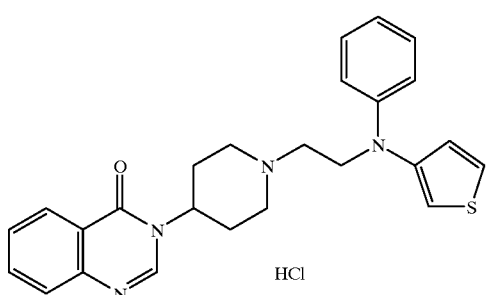<br>HCl<br>(white solid; 80%) | DMSO-d$_6$ 300 MHz<br>1.90–2.26(2H, m)<br>2.45–2.65(2H, m)<br>3.18–3.45(4H, m)<br>3.55–3.85(2H, m)<br>4.10–4.25(2H, m)<br>4.75–4.95(1H, m)<br>6.91(1H, dd, J=5.1Hz, 1.5Hz)<br>6.96(1H, d, J=7.5Hz)<br>7.05(2H, d, J=8.1Hz)<br>7.08–7.16(1H, m)<br>7.23–7.34(2H, m)<br>7.52–7.63(2H, m)<br>7.71(1H, d,J=7.8Hz)<br>7.82–7.90(1H, m)<br>8.15–8.22(1H, m)<br>8.30(1H, s)<br>10.99(1H, brs) | FAB$^+$ 431 |
| 15 | 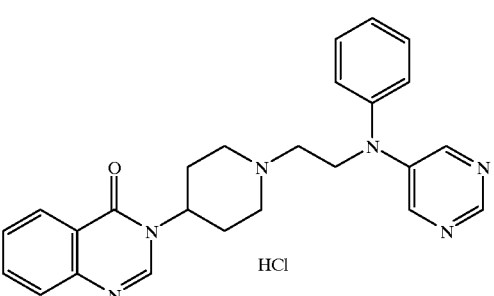<br>HCl<br>(yellow solid; 100%) | DMSO-d$_6$ 300 MHz<br>2.06–2.20(2H, m)<br>2.50–2.65(2H, m)<br>3.10–3.48(4H, m)<br>3.65–3.85(2H, m)<br>4.20–4.40(2H, m)<br>4.75–4.93(1H, m)<br>7.22–7.38(3H, m)<br>7.48(2H, t, J=7.8Hz)<br>7.59(1H, t, J=6.9Hz)<br>7.72(1H, d, J=8.1Hz)<br>7.81–7.92(1H, m)<br>8.19(1H, d, J=6.3Hz)<br>8.34(1H,s)<br>8.47(2H, s)<br>8.72(1H, s)<br>11.15(1H, brs) | FAB$^+$ 427 |

TABLE 8

| Example | Compound (Properties; yield from the final step) | $^1$H NMR ($\delta$) ppm | MS |
|---|---|---|---|
| 16 | 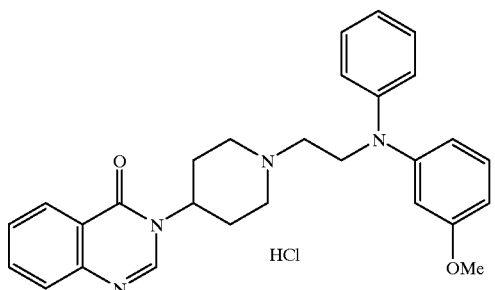<br>HCl<br>(white solid; 67%) | DMSO-d$_6$ 300 MHz<br>1.90–2.22(2H, m)<br>2.50–2.68(2H, m)<br>3.20–3.42(4H, m)<br>3.65–3.80(2H, m)<br>3.74(3H, s)<br>4.17–4.30(2H, m)<br>4.78–7.96(1H, m)<br>6.52–6.64(3H, m)<br>7.04(1H, t, J=7.2Hz)<br>7.12(2H, d, J=7.5Hz)<br>7.14–7.24(1H, m)<br>7.34(2H, t, J=7.8Hz)<br>7.59(1H, t, J=8.1Hz)<br>7.73(1H,d, J=8.1Hz)<br>7.82–7.94(1H, m)<br>8.19(1H, d, J=6.0Hz)<br>8.37(1H, s)<br>11.30(1H, brs) | FAB$^+$ 455 |

TABLE 8-continued

| Example | Compound (Properties; yield from the final step) | $^1$H NMR ($\delta$) ppm | MS |
|---|---|---|---|
| 17 | 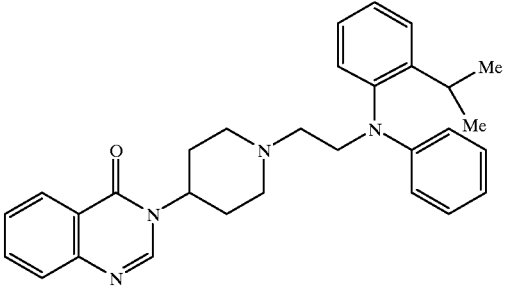<br>(white solid; 40%) | CDCl$_3$ 300 MHz<br>1.05–1.25(6H, m)<br>1.90–2.10(4H, m)<br>2.22–2.40(2H, m)<br>2.68–2.84(2H, m)<br>3.00–3.18(3H, m)<br>3.68–3.85(2H, m)<br>4.79–5.00(1H, m)<br>6.43–6.56(2H, m)<br>6.62–6.74(1H, m)<br>7.06–7.57(7H, m)<br>7.65–7.82(2H, m)<br>8.09–8.19(1H, m)<br>8.24–8.37(1H, m) | FAB$^+$<br>467 |
| 18 | 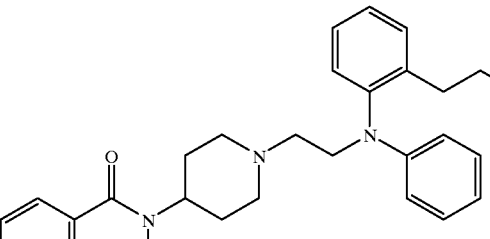<br>(white solid; 38%) | CDCl$_3$ 300 MHz<br>0.84(3H, t, J=7.1Hz)<br>1.21–1.36(2H, m)<br>1.48–1.60(2H, m)<br>1.86–2.04(4H, m)<br>2.22–2.38(2H, m)<br>2.47(2H, t, J=7.9Hz)<br>2.75(2H, t, J=7.7Hz)<br>3.04–3.16(2H, m)<br>3.76(2H, t, J=7.5Hz)<br>4.80–4.94(1H, m)<br>6.51(2H, d, J=7.7Hz)<br>6.69(1H, t, J=7.1Hz)<br>7.20–7.38(6H, m)<br>7.47–7.53(1H, m)<br>7.68–7.80(2H, m)<br>8.14(1H, s)<br>8.31(1H, dd, J=8.1Hz, 1.5Hz) | FAB$^+$<br>481 |

TABLE 9

| Example | Compound (Properties; yield from the final step) | $^1$H NMR ($\delta$) ppm | MS |
|---|---|---|---|
| 19 | 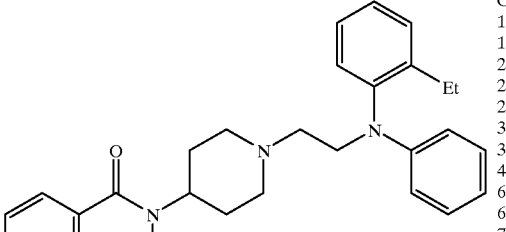<br>(white solid; 46%) | CDCl$_3$ 300 MHz<br>1.15(3H, t, J=7.5Hz)<br>1.85–2.00(4H, m)<br>2.20–2.38(2H, m)<br>2.51(2H, q, J=7.5Hz)<br>2.74(2H, t, J=7.5Hz)<br>3.03–3.14(2H, m)<br>3.78(2H, t, J=7.5Hz)<br>4.80–4.95(1H, m)<br>6.50(2H, d, J=8.1Hz)<br>6.69(1H, t, J=7.4Hz)<br>7.12–7.38(6H, m)<br>7.47–7.53(1H, m)<br>7.68–7.79(2H, m)<br>8.14(1H, s)<br>8.31(1H, dd, J=8.3Hz, 1.4Hz) | FAB$^+$ 453 |

TABLE 9-continued

| Example | Compound (Properties; yield from the final step) | $^1$H NMR ($\delta$) ppm | MS |
|---|---|---|---|
| 20 | 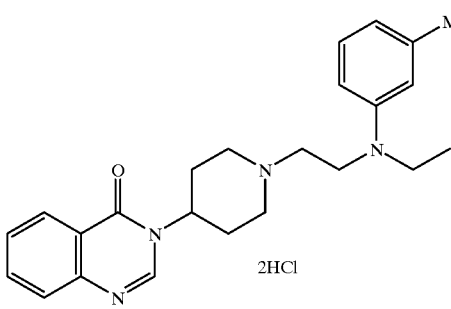<br>2HCl<br>(white solid; 96%) | CDCl$_3$ 400 MHz<br>1.09(3H, t, J=5.2Hz)<br>2.05–2.19(2H, m)<br>2.30(3H, s)<br>2.50–2.73(2H, m)<br>3.15–3.55(6H, m)<br>3.59–3.77(2H, m)<br>3.79–3.98(2H, m)<br>4.81–5.00(1H, m)<br>6.56–7.26(4H, m)<br>7.60(1H, t, J=5.6Hz)<br>7.75(1H, d, J=6.1Hz)<br>7.82–7.95(1H, m)<br>8.20(1H, d, J=5.9Hz)<br>8.47(1H, brs)<br>11.39(1H, brs) | FAB$^+$ 391 |
| 21 | 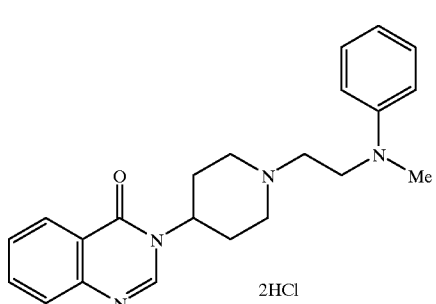<br>2HCl<br>(white solid; 100%) | DMSO-d$_6$ 400 MHz<br>2.00–2.23(2H, m)<br>2.50–2.74(2H, m)<br>2.96(3H, s)<br>3.09–3.44(4H, m)<br>3.57–3.79(2H, m)<br>3.80–3.96(2H, m)<br>4.84–5.01(1H, m)<br>6.75(1H, t, J=5.4Hz)<br>6.94(2H, d, J=6.0Hz)<br>7.24(2H, t, J=5.8Hz)<br>7.62(1H, t, J=5.6Hz)<br>7.78(1H, d, J=6.1Hz)<br>7.90(1H, t, J=5.4Hz)<br>8.20(1H, d, J=5.9Hz)<br>8.52(1H, brs)<br>11.44(1H, brs) | FAB$^+$ 363 |

TABLE 10

| Example | Compound (Properties; yield from the final step) | $^1$H NMR ($\delta$) ppm | MS |
|---|---|---|---|
| 22 | 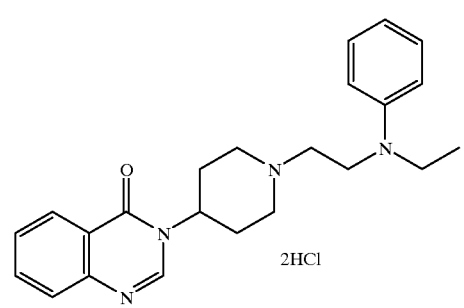<br>2HCl<br>(white solid; 91%) | DMSO-d$_6$ 300 MHz<br>1.10(3H, t, J=6.9Hz)<br>2.00–2.24(2H, m)<br>2.49–2.78(2H, m)<br>3.12–3.40(4H, m)<br>3.45(2H, q, J=6.9Hz)<br>3.54–3.98(4H, m)<br>4.85–5.02(1H, m)<br>6.62–7.10(3H, m)<br>7.12–7.38(2H, m)<br>7.60(1H, t, J=8.1Hz)<br>7.75(1H, d, J=8.1Hz)<br>7.89(1H, t, J=7.2Hz)<br>8.20(1H, d, J=6.9Hz)<br>8.46(1H, brs)<br>11.28(1H, brs) | FAB$^+$ 377 |

TABLE 10-continued

| Example | Compound (Properties; yield from the final step) | ¹H NMR (δ) ppm | MS |
|---|---|---|---|
| 23 | 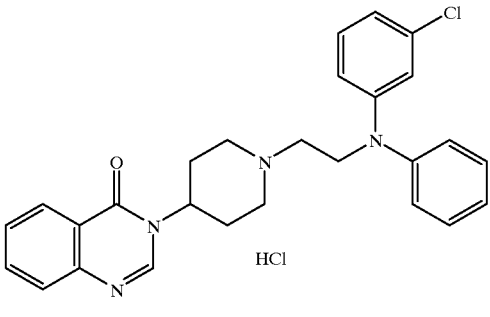<br>HCl<br>(white powder; 90%) | DMSO-$d_6$ 300 MHz<br>2.06–2.20(2H, m)<br>2.50–2.70(2H, m)<br>3.20–3.40(4H, m)<br>3.65–3.78(2H, m)<br>4.20–4.34(2H, m)<br>4.77–4.90(1H, m)<br>6.84–7.00(3H, m)<br>7.20–7.32(4H, m)<br>7.43(2H, t, J=7.7Hz)<br>7.60(1H, t, J=7.5Hz)<br>7.75(1H, d, J=8.1Hz)<br>7.88(1H, t, J=7.7Hz)<br>8.19(1H, d, J=7.2Hz)<br>8.40(1H, s)<br>11.34(1H, brs) | FAB⁺<br>459 |
| 24 | 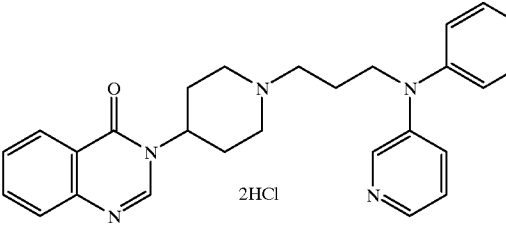<br>2HCl<br>(white powder; 100%) | DMSO-$d_6$ 300 MHz<br>2.10(4H, brd, J=10.2Hz)<br>2.50–2.70(2H, m)<br>3.10–3.25(4H, m)<br>3.61(2H, brd, J=12.3Hz)<br>3.93(2H, t, J=7.5Hz)<br>4.88–5.04(1H, m)<br>7.39–7.89(10H, m)<br>8.17–8.80(4H, m)<br>11.02(1H, brs) | FAB⁺<br>440 |

TABLE 11

| Example | Compound (Properties; yield from the final step) | ¹H NMR (δ) ppm | MS |
|---|---|---|---|
| 25 | 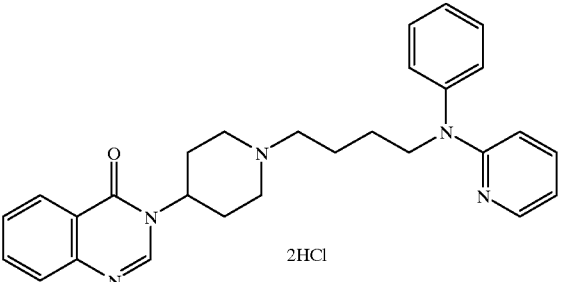<br>2HCl<br>(white powder; 91%) | DMSO-$d_6$ 300 MHz<br>1.56–2.18(6H, m)<br>2.55–2.70(2H, m)<br>3.00–3.70(6H, m)<br>3.96–4.12(2H, m)<br>4.85–5.05(1H, m)<br>6.69(1H, d, J=9.3Hz)<br>7.01(1H, t, J=6.6Hz)<br>7.42–7.78(7H, m)<br>7.82–7.96(2H, m)<br>8.08(1H, d, J=5.2Hz)<br>8.18(1H, dd, J=8.0Hz, 1.2Hz) | FAB⁺ 454 |
| 26 | 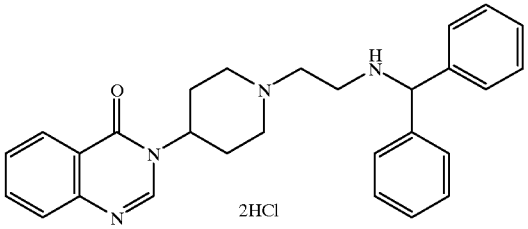<br>2HCl<br>(white powder; 100%) | DMSO-$d_6$ 300MHz<br>2.02–2.20(2H, m)<br>2.40–2.60(2H, m)<br>3.10–3.75(8H, m)<br>4.80–5.00(1H, m)<br>5.69(1H, brs)<br>7.30–7.55(6H, m)<br>7.59(1H, t, J=7.5Hz)<br>7.65–7.80(5H, m)<br>7.87(1H, t, J=7.5Hz)<br>8.18(1H, d, J=6.3Hz)<br>8.29(1H, s)<br>10.5–11.00(2H, brs) | FAB⁺ 439 |

TABLE 11-continued

| Example | Compound (Properties; yield from the final step) | ¹H NMR (δ) ppm | MS |
|---|---|---|---|
| 27 | 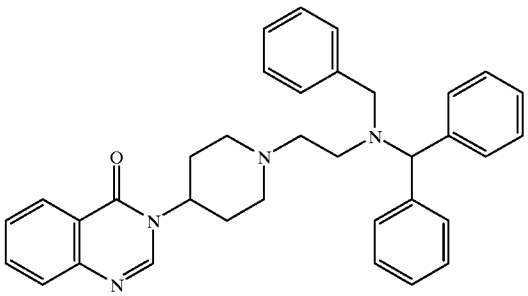<br>(colorless crystals; 37%) | CDCl₃ 300 MHz<br>1.75–1.95(4H, m)<br>2.02–2.11(2H, m)<br>2.45–2.50(2H, m)<br>2.65–2.71(2H, m)<br>2.81(2H, d, J=11.7Hz)<br>3.67(2H, s)<br>4.73–4.84(1H, m)<br>4.92(1H, s)<br>7.20–7.51(16H, m)<br>7.67–7.77(2H, m)<br>8.10(1H, s)<br>8.30(1H, d, J=8.1Hz) | FAB⁺ 529 |

TABLE 12

| Example | Compound (Properties; yield from the final step) | ¹H NMR (δ) ppm | MS |
|---|---|---|---|
| 28 | 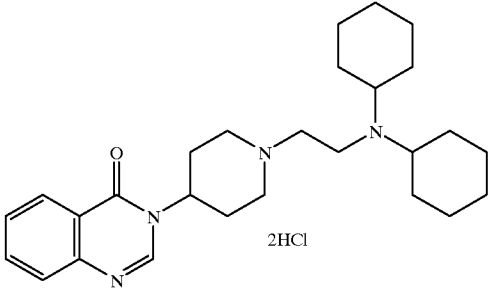<br>(white solid; 71%) | DMSO-d₆ 300 MHz<br>1.10–1.50(6H, m)<br>1.50–1.74(6H, m)<br>1.76–1.80(4H, m)<br>2.00–2.25(6H, m)<br>2.48–2.65(2H, m)<br>3.18–3.52(4H, m)<br>3.55–3.85(6H, m)<br>4.70–4.95(1H, m)<br>7.55–7.64(1H, m)<br>7.69–7.75(1H, m)<br>7.83–7.90(1H, m)<br>8.19(1H, dd, J=8.1Hz, 0.9Hz)<br>8.29(1H, s)<br>10.46(1H, brs)<br>11.50(1H, brs) | FAB⁺ 437 |
| 29 | 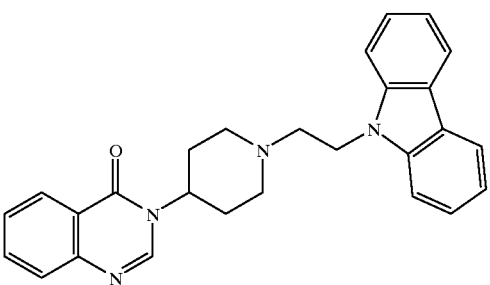<br>(white solid; 34%) | CDCl₃ 300 MHz<br>1.84–2.08(4H, m)<br>2.26–2.48(2H, m)<br>2.86(2H, t, J=7.4Hz)<br>3.05–3.22(2H, m)<br>4.48(2H, t, J=7.4Hz)<br>4.78–4.96(1H, m)<br>7.20–7.30(2H, m)<br>7.40–7.55(5H, m)<br>7.66–7.80(2H, m)<br>8.05–8.12(3H, m)<br>8.26–8.33(1H, m) | FAB+ 423 |

TABLE 12-continued

| Compound (Properties; | ¹H NMR (δ) ppm | MS |
|---|---|---|
| 30 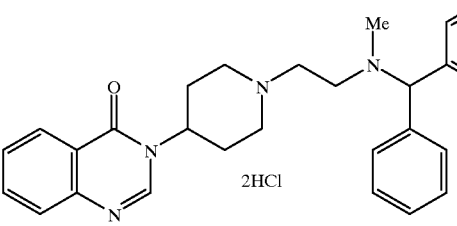<br>2HCl<br>(white powder; 100%) | DMSO-d₆ 400MHz<br>2.02–2.20(2H, m)<br>2.43–2.50(2H, m)<br>2.55–2.85(3H, m)<br>3.21(2H, brs)<br>3.52(4H, brs)<br>3.81(2H, brs)<br>4.76–4.92(1H, m)<br>5.74(1H, brs)<br>7.30–7.50(6H, m)<br>7.58(1H, t, J=5.6Hz)<br>7.72(1H, d, J=6.1Hz)<br>7.75–8.00(5H, m)<br>8.17(1H, d, J=5.5Hz)<br>8.30(1H, brs)<br>11.00(1H, brs)<br>12.46(1H, brs) | FAB⁺<br>453 |

TABLE 13

| Example | Compound (Propeties; yield from the final step) | ¹H NMR (δ) ppm | MS |
|---|---|---|---|
| 31 | 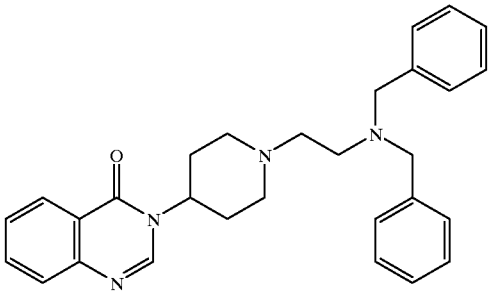<br>(white solid; 83%) | CDCl₃ 300 MHz<br>1.80–2.05(4H, m)<br>2.09–2.28(2H, m)<br>2.50–2.71(4H, m)<br>2.90–3.14(2H, m)<br>3.62(4H, s)<br>4.75–4.93(1H, m)<br>7.12–7.43(10H, m)<br>7.43–7.56(1H, m)<br>7.62–7.82(2H, m)<br>8.13(1H, s)<br>8.24–8.33(1H, m) | FAB+<br>453 |
| 32 | 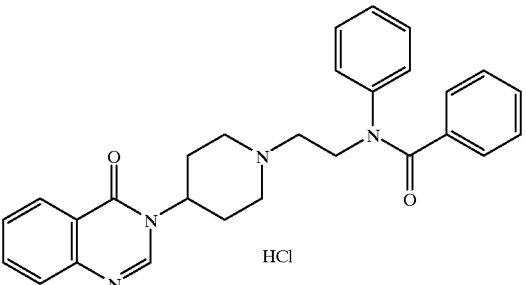<br>HCl<br>(white solid; 23%) | DMSO-d₆ 300 MHz<br>2.00–2.08(2H, m)<br>2.48–2.70(2H, m)<br>3.18–3.42(4H, m)<br>3.70–3.85(2H, m)<br>4.14–4.35(2H, m)<br>4.85–5.00(1H, m)<br>7.10–7.45(10H, m)<br>7.59(1H, t, J=6.9Hz)<br>7.72(1H, d, J=8.1Hz)<br>7.85–7.95(1H, m)<br>8.10–8.24(1H, m)<br>8.34(1H, s)<br>10.68(1H, brs) | FAB⁺<br>453 |

TABLE 13-continued

| Example | Compound (Propeties; yield from the final step) | $^1$H NMR ($\delta$) ppm | MS |
|---|---|---|---|
| 33 | 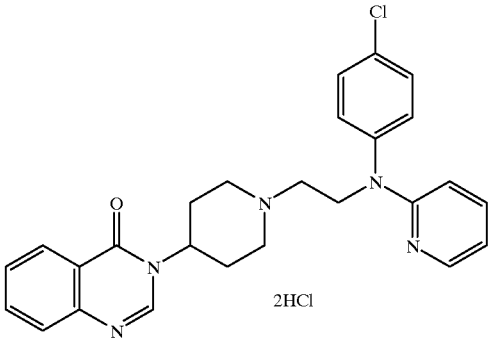<br>2HCl<br>(white powder; 100%) | DMSO-$d_6$ 300 MHz<br>2.04–2.20(2H, m)<br>2.50–2.70(2H, m)<br>3.22–3.56(4H, m)<br>3.63–3.80(2H, m)<br>4.38–4.50(2H, m)<br>4.82–5.00(1H, m)<br>6.80(1H, d, J=8.7Hz)<br>6.97(1H, t, J=6.3Hz)<br>7.46–7.94(8H, m)<br>8.16–8.22(2H, m)<br>8.47(1H, brs) | FAB$^+$<br>460 |

TABLE 14

| Example | Compound (Properties; yield from the final step) | $^1$H NMR ($\delta$) ppm | MS |
|---|---|---|---|
| 34 | 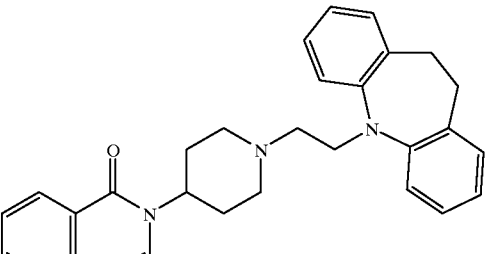<br>(white amorphous; 74%) | CDCl$_3$ 300 MHz<br>1.82–2.04(4H, m)<br>2.15–2.30(2H, m)<br>2.60(2H, t, J=7.1Hz)<br>2.92–3.06(2H, m)<br>3.18(4H, s)<br>3.94(2H, t, J=7.2Hz)<br>4.74–4.90(1H, m)<br>6.88–6.98(2H, m)<br>7.08–7.20(6H, m)<br>7.46–7.56(1H, m)<br>7.68–7.82(2H, m)<br>8.29(1H, s)<br>8.30(1H, dd, J=8.1Hz, 0.9Hz) | FAB$^+$<br>451 |
| 35 | 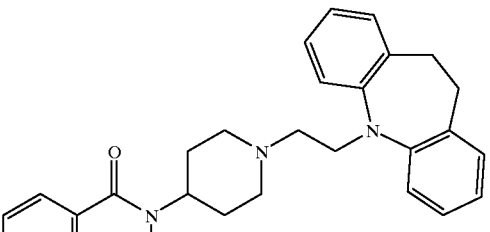<br>HCl<br>(white solid; 94%) | DMSO-$d_6$ 300 MHz<br>2.05–2.15(2H, m)<br>2.45–2.70(2H, m)<br>3.10–3.40(4H, m)<br>3.60–3.82(2H, m)<br>4.10–4.47(6H, m)<br>4.80–4.95(1H, m)<br>6.90–7.10(2H, m)<br>7.10–7.40(6H, m)<br>7.59(1H, t, J=7.8Hz)<br>7.72(1H, d, J=7.5Hz)<br>7.85(1H, t, J=1.2Hz)<br>8.18(1H, d, J=8.1Hz)<br>8.33(1H, s)<br>11.11(1H, brs) | FAB$^+$<br>451 |

TABLE 14-continued

| Example | Compound (Properties; yield from the final step) | $^1$H NMR ($\delta$) ppm | MS |
|---|---|---|---|
| 36 | 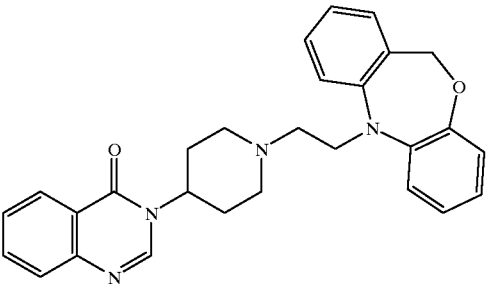<br>(pale yellow solid; 55%) | CDCl$_3$ 300 MHz<br>1.80–1.98(4H, m)<br>2.18–2.30(2H, m)<br>2.67(2H, t, J=6.8Hz)<br>2.98–3.06(2H, m)<br>3.95(2H, t, J=6.8Hz)<br>4.78–4.90(1H, m)<br>5.34(2H, s)<br>6.76–6.88(3H, m)<br>7.00–7.20(3H, m)<br>7.24–7.36(2H, m)<br>7.46–7.54(1H, m)<br>7.66–7.80(2H, m)<br>8.12(1H, s)<br>8.30(1H, dd, J=8.0Hz, 1.4Hz) | FAB$^+$ |

TABLE 15

| Example | Compound (Properties; yield from the final step) | $^1$H NMR ($\delta$) ppm | MS |
|---|---|---|---|
| 37 | 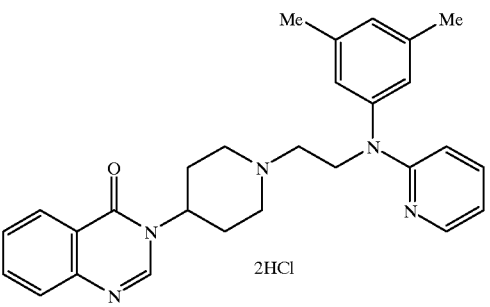<br>(white solid; 92%) | DMSO-d$_6$ 300MHz<br>2.04–2.22(2H, m)<br>2.34(6H, s)<br>2.50–2.72(2H, m)<br>3.17–3.58(4H, m)<br>3.61–3.82(2H, m)<br>4.32–4.50(2H, m)<br>4.76–5.00(1H, m)<br>6.70–6.88(1H, m)<br>6.98(1H, t, J=6.2Hz)<br>7.11(3H,s)<br>7.58(1H, t, J=10.5Hz)<br>7.58(1H, t, J=10.5Hz)<br>7.73–7.95(2H, m)<br>7.74(1H, d, J=7.8Hz)<br>8.08–8.27(2H, m)<br>8.44(1H, brs) | FAB$^+$<br>454 |
| 38 | 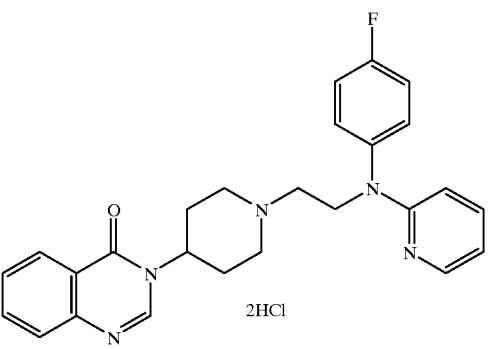<br>(white powder; 100%) | DMSO-d$_6$ 300MHz<br>2.12(2H, d, J=12.0Hz)<br>2.50–2.62(2H, m)<br>3.20–3.40(2H, m)<br>3.44(2H, brs)<br>3.73(2H, d, J=11.7Hz)<br>4.35–4.41(2H, m)<br>4.80–4.96(1H, m)<br>6.61(1H, brs)<br>6.86–6.96(1H, m)<br>7.41(2H, t,J=8.7Hz)<br>7.50–7.74(5H, m)<br>7.87(1H, t, J=6.6Hz)<br>8.19(2H, d, J=6.6Hz)<br>8.40(1H, brs) | FAB$^+$<br>444 |

TABLE 15-continued

| Example | Compound (Properties; yield from the final step) | ¹H NMR (δ) ppm | MS |
|---|---|---|---|
| 39 | (structure shown) HCl (white powder; 100%) | DMSO-d₆ 300MHz<br>2.05–2.20(2H, m)<br>2.44–2.67(2H, m)<br>3.25–3.54(4H, m)<br>3.66–3.78(2H, m)<br>4.32–4.53(2H, m)<br>4.80–4.96(1H, m)<br>6.68(1H, d, J=8.7Hz)<br>6.95(1H, t, J=6.3Hz)<br>7.41–7.64(6H, m)<br>7.69–7.81(2H, m)<br>7.83–7.92(1H, m)<br>8.19(1H, d, J=6.9Hz)<br>8.19(1H, d, J=7.2Hz)<br>8.43(1H, s) | FAB⁺<br>426 |

TABLE 16

| Example | Compound (Properties; yield from the final step) | ¹H NMR (δ) ppm | MS |
|---|---|---|---|
| 40 | (structure shown) HCl (white powder; 100%) | DMSO-d₆ 300MHz<br>2.07–2.22(2H, m)<br>2.48–2.69(2H, m)<br>3.24–3.50(4H, m)<br>3.72–3.86(2H, m)<br>4.48–4.68(2H, m)<br>4.80–4.98(1H, m)<br>7.14(2H, dd, J=7.2Hz, 5.1Hz)<br>7.33(2H, d, J=8.7Hz)<br>7.60(1H, t, J=7.2Hz)<br>7.74(1H, d, J=8.1Hz)<br>7.76–7.92(3H, m)<br>8.20(1H, d, J=8.1Hz)<br>8.38–8.52(3H, m)<br>10.83(1H, brs) | FAB⁺<br>427 |
| 41 | (structure shown) HCl (white powder; 93%) | DMSO-d₆ 300MHz<br>2.05–2.18(2H, m)<br>2.48–2.67(2H, m)<br>3.22–3.58(4H, m)<br>3.63–3.87(2H, m)<br>4.04–4.30(2H, m)<br>4.89(2H, s)<br>4.86–4.98(1H, m)<br>6.82–6.95(1H, m)<br>6.97–7.17(1H, m)<br>7.22–7.42(5H, m)<br>7.58(1H, t, J=7.5Hz)<br>7.72(1H, d, J=7.5Hz)<br>7.73–7.91(2H, m)<br>8.10–8.23(2H, m)<br>8.36(1H, s) | FAB⁺<br>440 |
| 42 | (structure shown) 2HCl (white solid; 72%) | DMSO-d₆ 300MHz<br>1.95–2.26(4H, m)<br>2.50–2.72(2H, m)<br>3.08–3.32(4H, m)<br>3.45–3.73(2H, m)<br>4.05–4.15(2H, m)<br>4.85–5.08(1H, m)<br>6.60–6.72(1H, m)<br>6.95–7.08(1H, m)<br>7.48–7.68(6H, m)<br>7.72(1H, d, J=7.9Hz)<br>7.80–7.94(2H, m)<br>8.08–8.16(1H, m)<br>8.18(1H, dd, J=8.0Hz, 1.1Hz)<br>8.30(1H, brs) | FAB⁺<br>440 |

TABLE 17

| Example | Compound (Properties; yield from the final step) | $^1$H NMR (δ) ppm | MS |
|---|---|---|---|
| 43 | 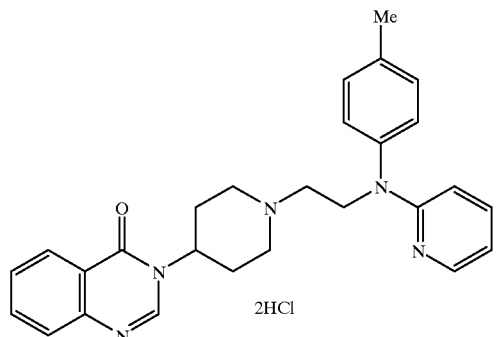<br>2HCl<br>(white powder; 100%) | DMSO-d$_6$ 300MHz<br>2.09–2.14(2H, m)<br>2.39(3H, s)<br>2.52–2.64(2H, m)<br>3.28–3.50(4H, m)<br>3.69–3.73(2H, m)<br>4.42–4.47(2H, m)<br>4.85–4.94(1H, m)<br>6.75–6.81(1H, m)<br>6.98(1H, t, J=6.3Hz)<br>7.37–7.43(4H,m)<br>7.58(1H, t, J=6.9Hz)<br>7.75(1H, d, J=8.1Hz)<br>7.80–7.91(2H, m)<br>8.12–8.21(2H, m)<br>8.46(1H, brs)<br>11.18(1H, brs) | FAB$^+$<br>440 |
| 44 | 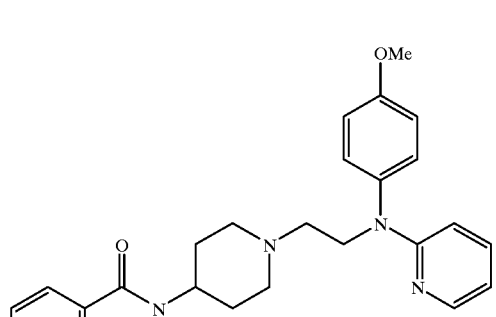<br>2HCl<br>(white powder; 100%) | DMSO-d$_6$ 300MHz<br>2.02–2.18(2H, m)<br>2.50–2.70(2H, m)<br>3.25–3.52(4H, m)<br>3.65–3.75(2H, m)<br>3.84(3H, s)<br>4.32–4.50(2H, m)<br>4.80–4.98(1H, m)<br>6.76–6.88(1H, m)<br>6.98(1H, t, J=6.6Hz)<br>7.12–7.20(2H,m)<br>7.45(2H, d, J=8.7Hz)<br>7.56–7.68(1H, m)<br>7.74(1H, d, J=7.2Hz)<br>7.78–7.96(2H, m)<br>8.09–8.13(1H, m)<br>8.19(1H, dd, J=8.0Hz, 1.4Hz)<br>8.75(1H, brs) | FAB$^+$<br>456 |
| 45 | 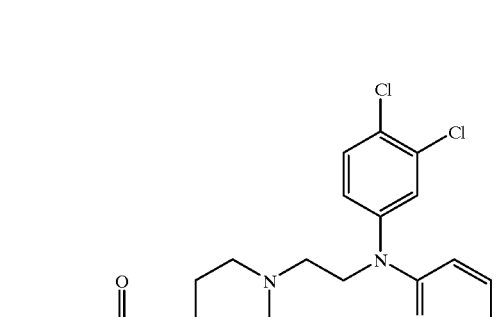<br>2HCl<br>(white powder; 100%) | DMSO-d$_6$ 300MHz<br>2.08–2.18(2H, m)<br>2.50–2.67(2H, m)<br>3.23–3.50(4H, m)<br>3.70–3.80(2H, m)<br>4.38–4.48(2H, m)<br>4.83–4.98(1H, m)<br>6.87(1H, d, J=8.7Hz)<br>6.98(1H, t, J=6.3Hz)<br>7.47–7.53(1H, m)<br>7.60(1H, t,J=7.5Hz)<br>7.71–7.92(5H, m)<br>8.18–8.25(2H, m)<br>8.46(1H, brs)<br>11.07(1H, brs) | FAB$^+$<br>494 |

TABLE 18

| Example | Compound (Properties; yield from the final step) | ¹H NMR (δ) ppm | MS |
|---|---|---|---|
| 46 | 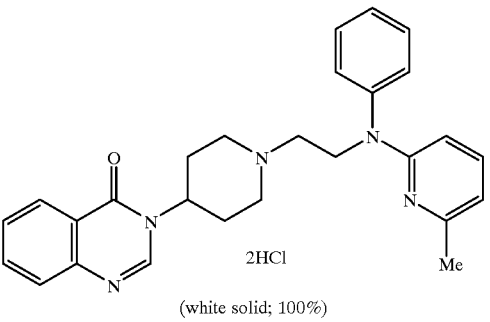<br>2HCl<br>(white solid; 100%) | DMSO-$d_6$ 300MHz<br>2.05–2.20(2H, m)<br>2.50(3H, s)<br>2.50–2.72(2H, m)<br>3.20–3.57(4H, m)<br>3.64–3.85(2H, m)<br>4.36–4.55(2H, m)<br>4.80–5.00(1H, m)<br>6.32(1H, d, J=8.4Hz)<br>6.74(1H, d, J=7.2Hz)<br>7.35–7.70(7H,m)<br>7.75(1H, d, J=7.8Hz)<br>7.80–7.95(1H, m)<br>8.19(1H, dd, J=8.1Hz, 1.5Hz)<br>8.46(1H, brs) | FAB⁺<br>440 |
| 47 | 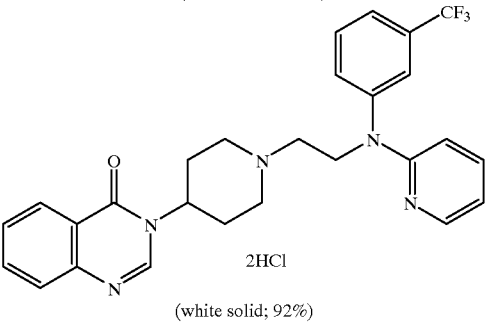<br>2HCl<br>(white solid; 92%) | DMSO-$d_6$ 300MHz<br>2.06–2.14(2H, m)<br>2.50–2.70(2H, m)<br>3.12–3.60(3H, m)<br>3.62–3.82(2H, m)<br>4.49(2H, t, J=6.9Hz)<br>4.80–5.00(1H, m)<br>6.81(1H, d, J=8.4Hz)<br>7.00(1H, t, J=6.6Hz)<br>7.61(1H, t, J=7.2Hz)<br>7.68–7.95(8H,m)<br>816–8.30(2H, m)<br>8.53(1H, brs) | FAB⁺<br>494 |
| 48 | 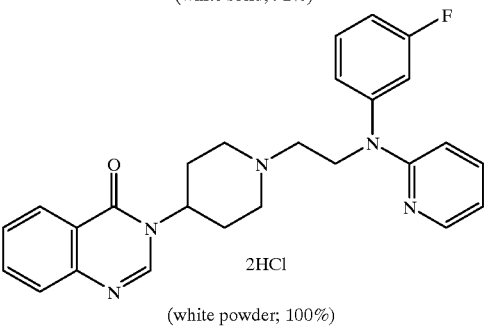<br>2HCl<br>(white powder; 100%) | DMSO-$d_6$ 300MHz<br>2.02–2.18(2H, m)<br>2.50–2.70(2H, m)<br>3.22–3.52(4H, m)<br>3.65–3.80(2H, m)<br>4.40–4.50(2H, m)<br>4.80–4.98(1H, m)<br>6.81(1H, d, J=8.7Hz)<br>6.97(1H, t, J=6.2Hz)<br>7.21–7.46(3H, m)<br>7.56–7.64(2H,m)<br>7.70–7.80(2H, m)<br>7.83–7.92(1H, m)<br>8.16–8.26(2H, m)<br>8.47(1H, brs) | FAB⁺<br>444 |

TABLE 19

| Example | Compound (Properties; yield from the final step) | ¹H NMR (δ) ppm | MS |
|---|---|---|---|
| 49 | 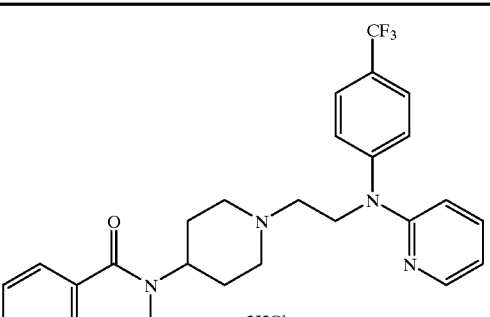<br>2HCl<br>(white powder; 100%) | DMSO-$d_6$ 300MHz<br>2.02–2.20(2H, m)<br>2.50–2.70(2H, m)<br>3.20–3.50(4H, m)<br>3.67–3.82(2H, m)<br>4.40–4.58(2H, m)<br>4.80–4.98(1H, m)<br>6.89(1H, d, J=8.4Hz)<br>7.00(1H, t, J=6.3Hz)<br>7.56–7.94(8H, m)<br>8.19(1H, d,J=6.6Hz)<br>8.26–8.36(1H, m)<br>8.47(1H, brs) | FAB⁺<br>494 |

TABLE 19-continued

| Example | Compound (Properties; yield from the final step) | $^1$H NMR (δ) ppm | MS |
|---|---|---|---|
| 50 | 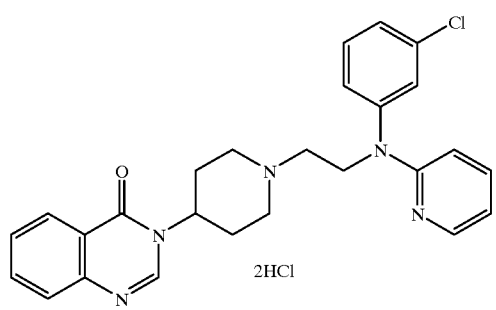<br>2HCl<br>(white powder; 100%) | DMSO-$d_6$300MHz<br>2.07–2.18(2H, m)<br>2.50–2.68(2H, m)<br>3.25–3.50(4H, m)<br>3.68–3.80(2H, m)<br>4.38–4.48(2H, m)<br>4.82–4.98(1H, m)<br>6.78(1H, d, J=9.3Hz)<br>6.97(1H, t, J=6.3Hz)<br>7.44–7.50(2H, m)<br>7.55–7.65(3H,m)<br>7.70–7.80(2H, m)<br>7.88(1H, t, J=7.5Hz)<br>8.17–8.25(2H, m)<br>8.47(1H, brs)<br>11.06(1H, brs) | FAB$^+$<br>460 |
| 51 | 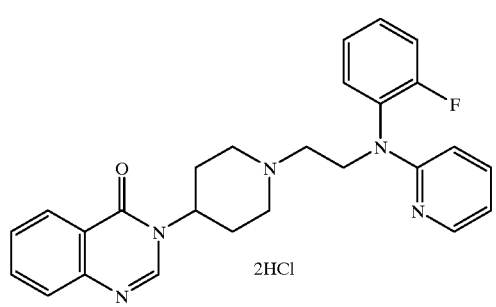<br>2HCl<br>(white powder; 100%) | DMSO-$d_6$300MHz<br>2.06–2.20(2H, m)<br>2.50–2.68(2H, m)<br>3.22–3.58(4H, m)<br>3.70–3.80(2H, m)<br>4.30–4.46(2H, m)<br>4.80–5.00(1H, m)<br>6.46–6.58(1H, m)<br>6.87–6.96(1H, m)<br>7.36–7.80(7H,m)<br>7.84–7.93(1H, m)<br>8.17–8.27(2H, m)<br>8.45(1H, brs)<br>11.09(1H, brs) | FAB$^+$<br>444 |

TABLE 20

| Example | Compound (Properties; yield from the final step) | $^1$H NMR (δ) ppm | MS |
|---|---|---|---|
| 52 | 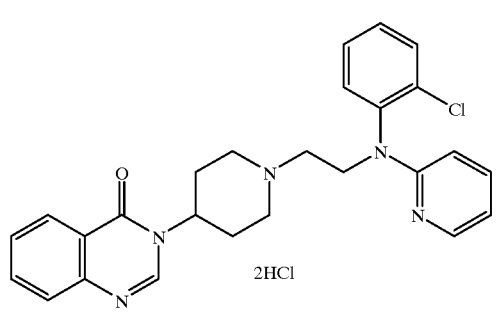<br>2HCl<br>(white solid; 99%) | DMSO-$d_6$300MHz<br>2.09–2.23(2H, m)<br>2.52–2.71(2H, m)<br>3.18–3.59(4H, m)<br>3.66–3.85(2H, m)<br>4.20–4.45(2H, m)<br>4.77–5.00(1H, m)<br>6.31(1H, brs)<br>6.89(1H, t, J=6.0Hz)<br>7.45–7.82(7H, m)<br>7.84–7.95(1H,m)<br>8.14–8.30(2H, m)<br>8.46(1H, brs) | FAB$^+$<br>460 |

TABLE 20-continued

| Example | Compound (Properties; yield from the final step) | $^1$H NMR ($\delta$) ppm | MS |
|---|---|---|---|
| 53 | 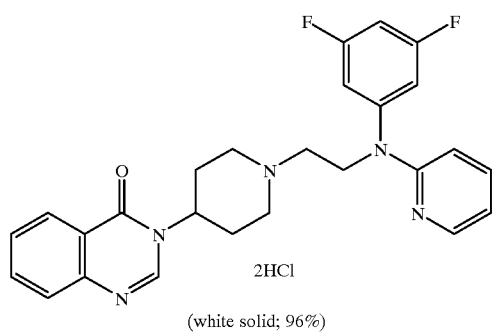<br>2HCl<br>(white solid; 96%) | DMSO-$d_6$300MHz<br>2.05–2.15(2H, m)<br>2.50–2.70(2H, m)<br>3.20–3.55(4H, m)<br>3.60–3.92(2H, m)<br>4.40–4.52(2H, m)<br>4.80–4.95(1H, m)<br>6.93(1H, d, J=8.4Hz)<br>7.00(1H, t, J=6.6Hz)<br>7.10–7.35(3H, m)<br>7.60(1H, t, J=6.9Hz)<br>7.64–7.80(2H,m)<br>7.86–7.94(1H, m)<br>8.19(1H, d, J=7.5Hz)<br>8.23–8.33(1H, m)<br>8.40(1H, brs)<br>11.03(1H, brs) | FAB$^+$<br>462 |
| 54 | 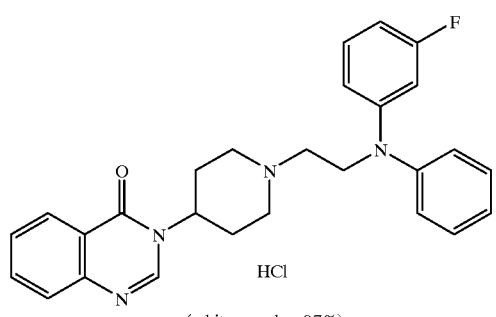<br>HCl<br>(white powder; 97%) | DMSO-$d_6$300MHz<br>2.06–2.20(2H, m)<br>2.50–2.70(2H, m)<br>3.20–3.40(4H, m)<br>3.65–3.78(2H, m)<br>4.20–4.34(2H, m)<br>4.78–4.95(1H, m)<br>6.64–6.80(3H, m)<br>7.16–7.26(4H, m)<br>7.41(2H, t, J=7.7Hz)<br>7.58(1H, t,J=7.5Hz)<br>7.72(1H, d, J=8.1Hz)<br>7.87(1H, t, J=6.8Hz)<br>8.17(1H, dd, J=7.8Hz, 0.9Hz)<br>8.39(1H, s)<br>11.28(1H, brs) | FAB$^+$<br>443 |

TABLE 21

| Example | Compound (Properties; yield from the final step) | $^1$H NMR ($\delta$) ppm | MS |
|---|---|---|---|
| 55 | 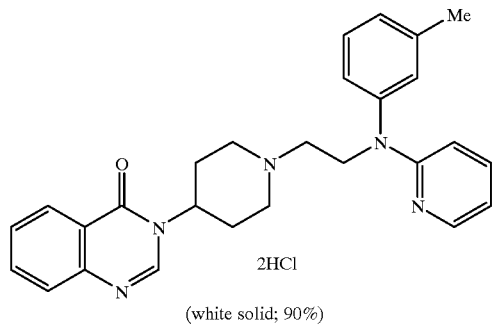<br>2HCl<br>(white solid; 90%) | DMSO-$d_6$300MHz<br>2.02–2.20(2H, m)<br>2.37(3H, s)<br>2.50–2.68(2H, m)<br>3.24–3.52(4H, m)<br>3.64–3.82(2H, m)<br>4.32–4.44(2H, m)<br>4.75–4.94(1H, m)<br>6.26–6.71(1H, m)<br>6.92(1H, t, J=6.6Hz)<br>7.20–7.31(3H,m)<br>7.46(1H, t, J=7.5Hz)<br>7.59(1H, t, J=6.9Hz)<br>7.68–7.80(2H, m)<br>7.82–7.92(1H, m)<br>8.12–8.22(2H, m)<br>8.40(1H, brs) | FAB$^+$<br>440 |

TABLE 21-continued

| Example | Compound (Properties; yield from the final step) | $^1$H NMR (δ) ppm | MS |
|---|---|---|---|
| 56 | 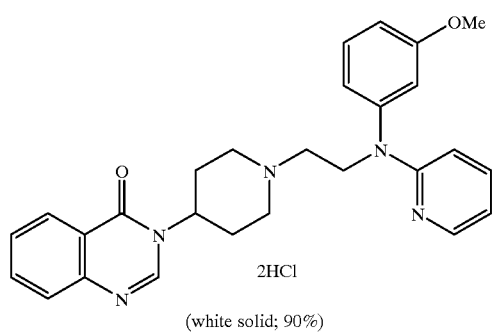<br>2HCl<br>(white solid; 90%) | DMSO-$d_6$ 300MHz<br>2.05–2.20(2H, m)<br>2.50–2.71(2H, m)<br>3.24–3.54(4H, m)<br>3.63–3.80(2H, m)<br>3.81(3H, s)<br>4.32–4.52(2H, m)<br>4.78–4.94(1H, m)<br>6.69–6.82(1H, m)<br>6.95(1H, t, J=6.3Hz)<br>6.98–7.13(3H,m)<br>7.48(1H, t, J=8.1Hz)<br>7.59(1H, t, J=7.8Hz)<br>7.68–7.81(2H, m)<br>7.88(1H, t, J=6.6Hz)<br>8.11–8.24(2H, m)<br>8.41(1H, brs) | FAB$^+$<br>456 |
| 57 | 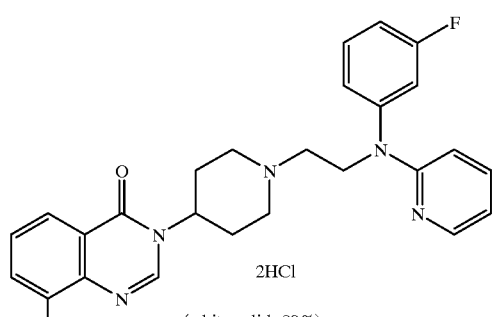<br>2HCl<br>(white solid; 89%) | DMSO-$d_6$ 300MHz<br>2.05–2.20(2H, m)<br>2.50–2.72(2H, m)<br>2.55(3H, s)<br>3.20–3.57(4H, m)<br>3.62–3.86(2H, m)<br>4.35–4.52(2H, m)<br>4.80–4.98(1H, m)<br>6.72–6.90(1H, m)<br>6.98(1H, t, J=5.9Hz)<br>7.20–7.38(2H,m)<br>7.40–7.51(2H, m)<br>7.59(1H, q, J=8.0Hz)<br>7.72(1H, d, J=3.7Hz)<br>7.68–7.81(1H, m)<br>8.02(1H, d, J=7.0Hz)<br>8.23(1H, d, J=5.5Hz)<br>8.38(1H, brs) | FAB$^+$<br>458 |

TABLE 22

| Example | Compound (Properties; yield from the final step) | $^1$H NMR (δ) ppm | MS |
|---|---|---|---|
| 58 | 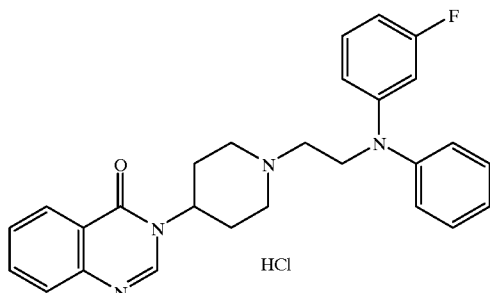<br>HCl<br>(white powder; 95%) | DMSO-$d_6$ 300MHz<br>2.07–2.17(2H, m)<br>2.52–2.65(2H, m)<br>3.27–3.36(4H, m)<br>3.69(2H, brs)<br>4.20–4.32(2H, m)<br>4.77–4.90(1H, m)<br>6.82–7.04(6H, m)<br>7.34(2H, q, J=7.8Hz)<br>7.58(1H, t, J=7.5Hz)<br>7.69–7.76(1H,m)<br>7.82–7.91(1H, m)<br>8.16–8.72(1H, m)<br>8.36(1H, s)<br>11.26(1H, brs) | FAB$^+$<br>461 |

TABLE 22-continued

| Example | Compound (Properties; yield from the final step) | $^1$H NMR (δ) ppm | MS |
|---|---|---|---|
| 59 | 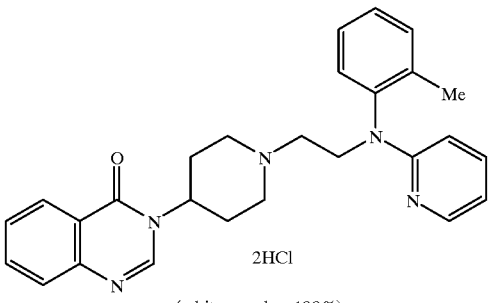<br>2HCl<br>(white powder; 100%) | DMSO-$d_6$300MHz<br>2.00–2.46(2H, m)<br>2.49(3H, s)<br>2.50–2.66(2H, m)<br>3.20–3.38(2H, m)<br>3.42–3.56(2H, m)<br>3.64–3.80(2H, m)<br>4.80–4.96(1H, m)<br>6.90–7.00(1H, m)<br>7.32–7.92(8H, m)<br>8.08–8.22(2H,m)<br>8.44(1H, brs) | FAB$^+$<br>440 |
| 60 | 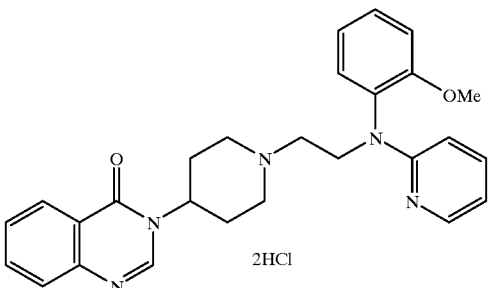<br>2HCl<br>(white powder; 92%) | DMSO-$d_6$300MHz<br>2.06–2.18(2H, m)<br>2.50–2.68(2H, m)<br>3.22–3.52(4H, m)<br>3.66–3.78(2H, m)<br>3.84(3H, s)<br>4.26–4.42(2H, m)<br>4.82–4.96(1H, s)<br>6.90–7.00(1H, m)<br>7.15(1H, t, J=7.5Hz)<br>7.30(1H, d,J=8.1Hz)<br>7.44–7.64(3H, m)<br>7.72–7.92(3H, m)<br>8.12–8.22(2H, m)<br>8.42(1H, brs)<br>11.12(1H, brs) | FAB$^+$<br>456 |

TABLE 23

| Example | Compound (Properties; yield from the final step) | $^1$H NMR (δ) ppm | MS |
|---|---|---|---|
| 61 | 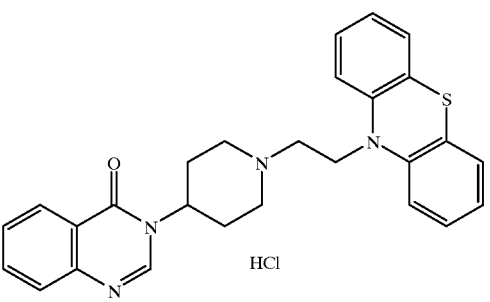<br>HCl<br>(pale purple solid; 100%) | DMSO-$d_6$300MHz<br>2.02–2.10(2H, m)<br>2.20–2.36(2H, m)<br>3.18–3.64(4H, m)<br>3.70–3.84(2H, m)<br>4.47(2H, t, J=7.0Hz)<br>4.70–5.00(1H, m)<br>7.04(2H, t, J=7.1Hz)<br>7.20–7.40(6H, m)<br>7.58(1H, t, J=7.5Hz)<br>7.72(1H, d,J=8.4Hz)<br>7.86(1H, t, J=7.3Hz)<br>8.18(1H, d, J=7.7Hz)<br>8.33(1H, s)<br>11.27(1H, brs) | FAB$^+$<br>455 |

TABLE 23-continued

| Example | Compound (Properties; yield from the final step) | ¹H NMR (δ) ppm | MS |
|---|---|---|---|
| 62 | 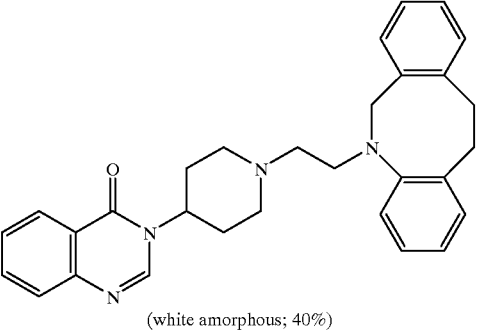<br>(white amorphous; 40%) | CDCl₃300MHz<br>1.65–1.94(4H, m)<br>2.02–2.20(2H, m)<br>2.49(2H, t, J=6.7Hz)<br>2.80–2.98(2H, m)<br>3.05–3.18(2H, m)<br>3.22–3.35(2H, m)<br>3.41(2H, t, J=6.7Hz)<br>4.24(2H, s)<br>4.70–4.88(1H, m)<br>6.80–6.92(1H,m)<br>7.00–7.22(6H, m)<br>7.45–7.56(1H, m)<br>7.65–7.80(2H, m)<br>8.10(1H, s)<br>8.29(1H, dd, J=8.0Hz, 1.0Hz) | FAB⁺<br>465 |
| 63 | 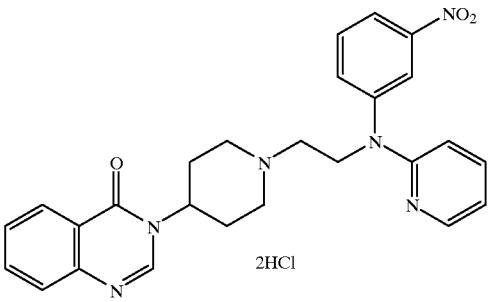<br>(yellow solid; 92%) | DMSO-d₆300MHz<br>2.08–2.20(2H, m)<br>2.50–2.70(2H, m)<br>3.23–3.52(4H, m)<br>3.62–3.86(2H, m)<br>4.47(2H, t, J=6.6Hz)<br>4.81–4.96(1H, m)<br>6.82(1H, d, J=8.4Hz)<br>6.97(1H, t, J=6.9Hz)<br>7.63(1H, t, J=7.2Hz)<br>7.67–8.00(5H,m)<br>8.12–8.24(2H, m)<br>8.26–8.32(2H, m)<br>8.43(1H, brs) | FAB⁺<br>471 |

TABLE 24

| Example | Compound (Properties; yield from the final step) | ¹H NMR (δ) ppm | MS |
|---|---|---|---|
| 64 | 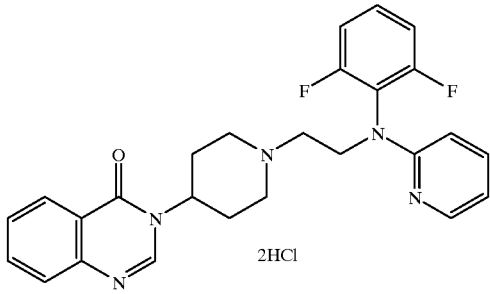<br>(white solid; 100%) | DMSO-d₆300MHz<br>2.06–2.19(2H, m)<br>2.33–2.60(2H, m)<br>3.10–3.50(4H, m)<br>3.60–3.85(2H, m)<br>4.29(2H, t, J=8.1Hz)<br>4.80–4.98(1H, m)<br>6.51(1H, d, J=8.4Hz)<br>6.80–6.92(1H, m)<br>7.34(2H, t, J=8.4Hz)<br>7.45–7.70(3H,m)<br>7.75(1H, d, J=9.0Hz)<br>7.80–7.92(1H, m)<br>8.10–8.20(2H, m)<br>8.43(1H, brs)<br>11,10(1H, brs) | FAB⁺<br>462 |

TABLE 24-continued

| Example | Compound (Properties; yield from the final step) | ¹H NMR (δ) ppm | MS |
|---|---|---|---|
| 65 | 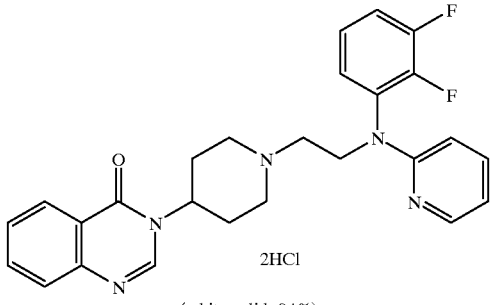<br>2HCl<br>(white solid; 94%) | DMSO-d₆300MHz<br>2.04–2.22(2H, m)<br>2.49–2.68(2H, m)<br>3.22–3.53(4H, m)<br>3.64–3.84(2H, m)<br>4.36(2H, t, J=7.5Hz<br>4.80–4.93(1H, m)<br>6.57(1H, d, J=8.4Hz)<br>6.89(1H, t, J=5.1Hz)<br>7.30–7.68(5H, m)<br>7.74('1H, d,J=7.8Hz)<br>7.81–7.92(1H, m)<br>8.14–8.30(2H, m)<br>8.42(1H, brs) | FAB⁺<br>462 |
| 66 | 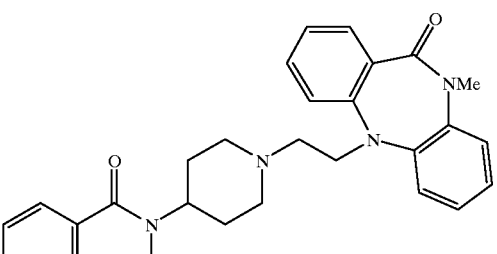<br>(white amorphous; 80%) | CDCL₃300MHz<br>1.88–2.02(4H, m)<br>2.22–2.38(2H, m)<br>2.70(2H, t, J=7.2Hz)<br>3.02–3.14(2H, m)<br>3.57(3H, s)<br>3.80–4.00(2H, m)<br>4.74–4.91(1H, m)<br>7.02–7.24(6H, m)<br>7.32–7.42(1H, m)<br>7.44–7.58(1H,m)<br>7.68–7.80(3H, m)<br>8.15(1H, s)<br>8.27–8.32(1H, m) | FAB⁺<br>480 |

TABLE 25

| Example | Compound (Properties; yield from the final step) | ¹H NMR (δ) ppm | MS |
|---|---|---|---|
| 67 | 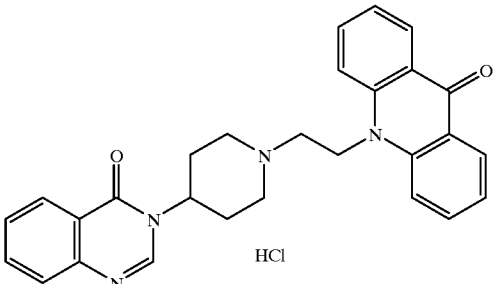<br>HCl<br>(yellow solid; 100%) | DMSO-d₆300MHz<br>2.05–2.38(2H, m)<br>2.42–2.78(2H, m)<br>3.30–3.98(6H, m)<br>4.50–5.50(3H, m)<br>7.41(2H, t, J=5.6Hz)<br>7.56–8.50(10H, m)<br>12.08(1H, brs) | FAB⁺<br>451 |
| 68 | 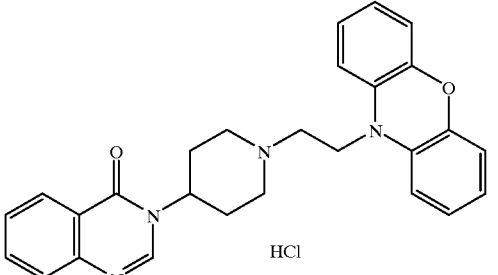<br>HCl<br>(pale yellowish white solid; 83%) | DMSO-d₆300MHz<br>2.08–2.26(2H, m)<br>2.50–2.70(2H, m)<br>3.14–3.46(4H, m)<br>3.70–3.89(2H, m)<br>4.10–4.22(2H, m)<br>4.75–4.92(1H, m)<br>6.55–6.80(4H, m)<br>6.80–7.02(4H, m)<br>7.59(1H, t, J=8.1Hz)<br>7.73(1H, d,J=8.1Hz)<br>7.84–7.92(1H, m)<br>8.20(1H, d, J=8.1Hz)<br>8.35(1H, s)<br>11.40(1H, brs) | FAB⁺<br>439 |

TABLE 25-continued

| Example | Compound (Properties; yield from the final step) | $^1$H NMR ($\delta$) ppm | MS |
|---|---|---|---|
| 69 | 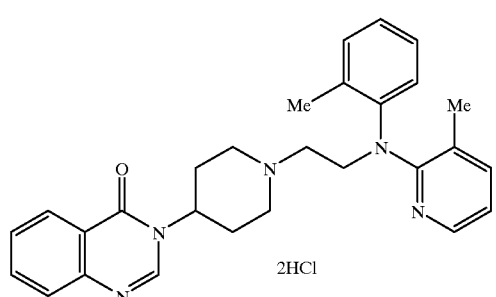<br>2HCl<br>(white solid; 80%) | DMSO-$d_6$ 300MHz<br>1.50(3H, s)<br>2.04–2.23(2H, m)<br>2.29(3H, s)<br>2.50–2.70(2H, m)<br>3.20–3.48(4H, m)<br>3.64–3.82(2H, m)<br>4.06–4.19(2H, m)<br>4.76–5.00(1H, m)<br>6.85–6.96(1H, m)<br>7.00–7.09(1H, m)<br>7.11–7.26(2H, m)<br>7.28–7.39(1H, m)<br>7.50–7.76(2H, m)<br>7.74(1H, d, J=8.1Hz)<br>7.82–7.95(1H, m)<br>8.20(1H, d, J=8.0Hz)<br>8.25–8.34(1H, m)<br>8.43(1H, brs) | FAB$^+$<br>454 |

TABLE 26

| Example | Compound (Properties; yield from the final step) | $^1$H NMR ($\delta$) ppm | MS |
|---|---|---|---|
| 70 | 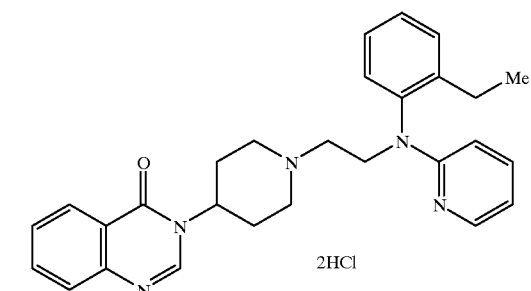<br>2HCl<br>(white solid; 95%) | DMSO-$d_6$ 300MHz<br>1.18(3H, t, J=7.2Hz)<br>2.04–2.20(2H, m)<br>2.40–2.68(4H, m)<br>3.22–3.62(4H, m)<br>3.68–3.82(2H, m)<br>3.85–4.80(2H, m)<br>4.80–4.94(1H, m)<br>6.86–7.00(1H, m)<br>7.32–7.68(6H, m)<br>7.73(2H, d, J=7.8Hz)<br>7.82–7.91(1H, m)<br>8.11–8.24(2H, m)<br>8.42(1H, brs) | FAB$^+$<br>454 |
| 71 | 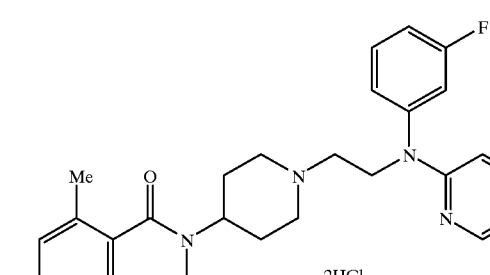<br>2HCl<br>(white solid; 100%) | DMSO-$d_6$ 300MHz<br>2.04–2.19(2H, m)<br>2.48–2.65(2H, m)<br>2.80(3H, s)<br>3.20–3.54(4H, m)<br>3.65–3.80(2H, m)<br>4.36–4.50(2H, m)<br>4.75–4.94(1H, m)<br>6.76(1H, d, J=8.7Hz)<br>6.94(1H, t, J=6.0Hz)<br>7.12–7.45(4H, m)<br>7.52–7.62(2H, m)<br>7.66–7.78(2H, m)<br>8.22–8.29(1H, m)<br>8.49(1H, brs) | FAB$^+$<br>458 |

TABLE 26-continued

| Example | Compound (Properties; yield from the final step) | $^1$H NMR (δ) ppm | MS |
|---|---|---|---|
| 72 | 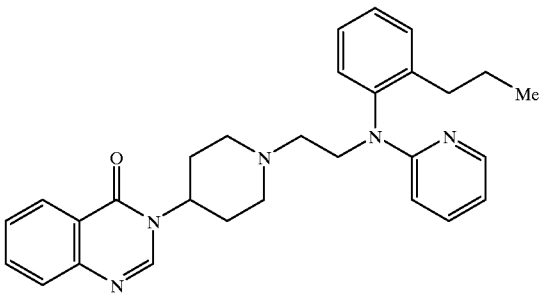<br>(colorless crystals; 73%) | CDCl$_3$ 300MHz<br>0.89(3H, t, J=7.5Hz)<br>1.52–1.64(2H, m)<br>1.85–2.00(4H, m)<br>2.20–2.35(2H, m)<br>2.47(2H, t, J=7.8Hz)<br>2.75(2H, t, J=7.2Hz)<br>3.14(2H, d, J=11.7Hz)<br>3.70(1H, brs)<br>4.40(1H, brs)<br>4.80–4.95(1H, m)<br>5.94(1H, d, J=9.0Hz)<br>6.54(1H, dd, J=6.3, 5.1Hz)<br>7.18–7.39(5H, m)<br>7.45–7.52(1H, m)<br>7.68–7.78(2H, m)<br>8.12(1H, s)<br>8.18(1H, d, J=5.1Hz)<br>8.31(1H, d, J=7.8Hz) | FAB$^+$<br>468 |

TABLE 27

| Example | Compound (Properties; yield from the final step) | $^1$H NMR (δ) ppm | MS |
|---|---|---|---|
| 73 | 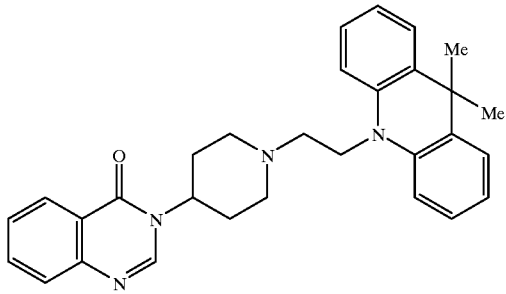<br>(white solid; 60%) | CDCl$_3$ 300MHz<br>1.55(3H, s)<br>1.57(3H, s)<br>1.96–2.12(4H, m)<br>2.31–2.45(2H, m)<br>2.86(2H, t, J=7.7Hz)<br>3.16–3.27(2H, m)<br>4.17(2H, t, J=7.0Hz)<br>4.82–5.00(1H, m)<br>6.98(1H, t, J=7.7Hz)<br>7.03(1H, d, J=8.1Hz)<br>7.18–7.27(1H, m)<br>7.42(1H, dd, J=7.7Hz, 1.5Hz)<br>7.48–7.56(1H, m)<br>7.67–7.81(1H, m)<br>8.17(1H, s)<br>8.30–8.38(1H, brs) | FAB$^+$<br>465 |
| 74 | 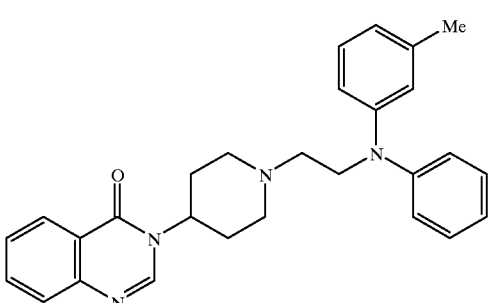<br>(white amorphous; 61%) | CDCl$_3$ 300MHz<br>1.86–2.02(4H, m)<br>2.23–2.38(2H, m)<br>2.30(3H, s)<br>2.71(2H, t, J=7.8Hz)<br>3.04–3.15(2H, m)<br>3.89(2H, t, J=7.8Hz)<br>4.78–4.94(1H, m)<br>6.75–6.85(3H, m)<br>6.94(1H, t, J=7.5Hz)<br>7.00(2H, d, J=7.5Hz)<br>7.17(1H, t, J=7.5Hz)<br>7.20–7.32(2H, m)<br>7.40–7.53(1H, m)<br>7.65–7.82(2H, m)<br>8.14(1H, s)<br>8.31(1H, dd, J=8.1Hz, 1.5Hz) | FAB$^+$<br>439 |

TABLE 27-continued

| Example | Compound (Properties; yield from the final step) | $^1$H NMR ($\delta$) ppm | MS |
|---|---|---|---|
| 75 | 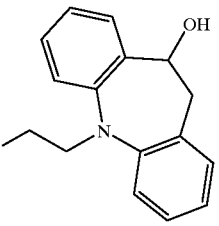<br>(white crystals; 47%) | CDCl$_3$300MHz<br>1.70–1.88(2H, m)<br>1.96–2.24(4H, m)<br>2.50–2.68(2H, m)<br>2.70–2.96(2H, m)<br>3.34(1H, dd, J=17.3Hz, 3.8Hz)<br>3.51(1H, dd, J=17.4Hz, 3.8Hz)<br>3.76–3.88(1H, m)<br>3.92–4.06(1H, m)<br>4.76–4.96(2H, m)<br>6.22(1H,brs)<br>6.85–6.96(1H, m)<br>7.00–7.32(7H, m)<br>7.43–7.54(1H, m)<br>7.65–7.78(2H, m)<br>8.24–8.36(2H, m) | FAB$^+$<br>467 |

TABLE 28

| Example | Compound (Properties; yield from the final step) | $^1$H NMR ($\delta$) ppm | MS |
|---|---|---|---|
| 76 | 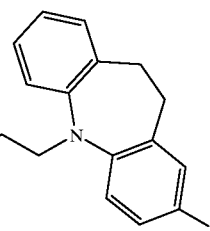<br>(white amorphous; 96%) | CDCl$_3$400MHz<br>1.87–2.03(4H, m)<br>2.15–2.29(2H, m)<br>2.60(2H, t, J=5.3Hz)<br>2.98–3.18(6H, m)<br>3.89(2H, t, J=5.4Hz)<br>4.80–4.92(1H, m)<br>6.52(1H, dd, J=6.4Hz, 2.2Hz)<br>6.64(1H, d, J=2.2Hz)<br>6.71(1H, brs)<br>6.84–6.90(1H,m)<br>6.93(1H, d, J=6.5Hz)<br>7.02–7.14(3H, m)<br>7.46–7.53(1H, m)<br>7.67–7.78(2H, m)<br>8.14(1H, s)<br>8.56(1H, dd, J=6.0Hz, 1.0Hz) | FAB$^+$<br>467 |

The following shows the test results of MTP inhibitory activity of the compounds of the present invention. The following Test Examples were conducted with reference to Chemistry and Physics of Lipids, 38, 205–222 (1985).

Test Example

Test Example 1.

Effect (in vitro) on secretion of apolipoprotein B (Apo B) from human hepatoma cells (HepG2 cells)

HepG2 cells were seeded onto a 48- or 96-well plate and cultured for several days. The culture medium was replaced with DMEM culture medium supplemented with 1.5% bovine serum albumin. After 24 hours, the culture medium was replaced with DMEM medium supplemented with 1.5% bovine serum albumin and 0.8 mM sodium oleate as an assay medium. Each of the test compounds was dissolved in dimethylsulfoxide and added to the assay medium to produce a final dimethylsulfoxide concentration of 1%. After 5 hours, the culture medium was collected, and Apo B in the culture medium was measured by the sandwich ELISA method. The results are shown in Tables 29 and 30.

Test Example 2.

Effect (in vitro) on transfer of triglycerides (TG) between liposomes of small-unilamellar-vesicles (SUV)

SUV liposomes composed of triolein, [$^{14}$C]triolein, phosphatidylcholine (PC), and cardiolipin were prepared as donors, while SUV liposomes composed of triolein, PC, and [$^3$H]PC were prepared as acceptors. The donors and the acceptors were mixed to a ratio of 1:5. A dimethylsulfoxide solution of test compounds that was adjusted to have a final dimethylsulfoxide concentration of 1%, crude MTP purified by FPLC from a microsome fraction of bovine liver, and the donor and acceptor mixture prepared above were added to an assay buffer. After the assay buffer was incubated for 1 hour at 37° C., a diethylaminoethylcellulose (DEAE-cellulose) suspension was added thereto. The buffer was shaken for 4 minutes and centrifuged to collect a supernatant. Residual [$^{14}$C]triolein in the supernatant was measured with a liquid scintillation counter. Taking this [$^{14}$C]triolein count as the TG-transferring activity of MTP, inhibitory activities of test compounds were calculated. The results are shown in Tables 29 and 30.

Test Example 3.

Effect (in vivo) on increasing TG after olive oil was loaded orally

Olive oil was administered orally to 10- to 11-week-old syrian hamsters at a dose of 2 ml/kg, and the blood was collected after 4 hours. Blood was collected from the orbital venous plexus under light anesthesia with ether using a heparin-treated glass capillary in an amount of 100 μl/head at a time. Test compounds were dissolved or suspended in 0.5% methylcellulose and administered orally 30 minutes before the administration of olive oil. Collected blood was immediately cooled with ice, and plasma was collected by centrifugation at 12,000 rpm for 5 minutes. A plasma TG value was measured using a measuring kit and an automatic blood analyzer.

The results are shown in Tables 29 and 30.

Test Example 4.

Effect (in vivo) on hepatic TG Output Rate (TGOR) after administration of Triton WR-1339

Ten- to eleven-week-old Syrian hamsters were used after 24-hour fasting. (Water was administered ad libitum.) Under light anesthesia with ether, Triton WR-1339 was administered via the penile vein at a dose of 400 mg/kg, and blood was collected at 0 (before administration), 1, 2, and 3 hours after administration. Blood was collected via the orbital venous plexus under light ether anesthesia using a heparin-treated glass capillary in an amount of 100–250 μl/head at a time. Test compounds were suspended in 0.5% methylcellulose and administered orally 30 minutes before administration of Triton WR-1339. Collected blood was immediately cooled with ice, and plasma was collected by centrifugation at 12,000 rpm for 5 minutes. The plasma TG value was measured using a measuring kit and an automatic blood analyzer. TGOR was calculated from time-course changes of plasma TG values of each test compound.

The results are shown in Tables 29 and 30.

TABLE 29

| | Test Example | | | |
|---|---|---|---|---|
| | in vitro; $IC_{50}$ (μM) | | in vivo; (mg/kg) | |
| Example | Inhibition of Apo B secretion | Inhibition of TG transfer | Inhibition of TG increase | Inhibition of hepatic TGOR |
| 1 | 0.1 | 0.6 | 10 | |
| 3 | 0.7 | 0.6 | | |
| 4 | 0.7 | 0.8 | | |
| 5 | 0.7 | 0.1 | | |
| 7 | 0.03 | 0.1 | 10 | |
| 8 | 0.03 | 0.1 | 3 | |
| 10 | 0.2 | 0.2 | | |
| 11 | 0.2 | 0.6 | | |
| 12 | 0.08 | 0.07 | | |
| 13 | 0.03 | 0.06 | 10 | |
| 14 | 0.2 | 0.2 | | |
| 16 | 0.3 | 5 | | |
| 17 | 0.05 | 0.06 | 10 | |
| 18 | 0.09 | 0.2 | 10 | |
| 19 | 0.04 | 0.1 | 10 | |
| 22 | 0.3 | 0.6 | | |
| 23 | 0.3 | 0.5 | 10 | |
| 24 | 0.1 | 0.2 | | |
| 25 | 0.6 | 0.2 | | |
| 30 | 0.4 | 0.9 | | |
| 34 | 0.1 | 0.02 | 3 | 10 |
| 35 | 0.2 | 0.02 | 10 | |

TABLE 30

| | Test Example | | | |
|---|---|---|---|---|
| | in vitro; $IC_{50}$ (μM) | | in vivo; (mg/kg) | |
| Example | Inhibition of Apo B secretion | Inhibition of TG transfer | Inhibition of TG increase | Inhibition of hepatic TGOR |
| 36 | 0.07 | 0.02 | 3 | 30 |
| 39 | 0.2 | 0.2 | 30 | |
| 40 | 0.2 | 0.8 | | |
| 42 | 0.03 | 0.04 | | |
| 48 | 0.04 | 0.2 | 10 | 30 |
| 50 | 0.07 | 0.3 | 30 | |
| 51 | 0.03 | 0.3 | | |
| 52 | 0.03 | 0.1 | 10 | |
| 53 | 0.3 | 0.6 | | |
| 54 | 0.2 | 0.3 | 30 | |
| 55 | 0.3 | 0.2 | 30 | |
| 56 | 0.2 | 0.1 | 30 | |
| 59 | 0.03 | 0.07 | | |
| 60 | 0.2 | 0.2 | | |
| 64 | 0.03 | 0.2 | 30 | |
| 65 | 0.03 | 0.1 | 30 | |
| 66 | 0.3 | | | |
| 69 | 0.5 | 0.5 | | |
| 70 | 0.03 | 0.06 | | |
| 72 | 0.02 | 0.03 | 10 | |
| 73 | 0.4 | 0.2 | | |
| 75 | 0.3 | | | |

INDUSTRIAL APPLICABILITY

The above test results indicate that compounds (I) of the present invention have excellent MTP-inhibitory activity. The compounds also increase HDL. Thus, these compounds not only inhibit formation of LDL that is a cause of arteriosclerotic diseases but also regulate TG, cholesterol, and lipoproteins such as LDL in the blood and regulate cellular lipids through regulation of MTP activity. They can also be used as a new type of preventive or therapeutic agents for hyperlipemia or arteriosclerotic diseases. Furthermore, they can be used as therapeutic or preventive agents for pancreatitis, obesity, hypercholesterolemia, and hypertriglyceridemia.

What is claimed is:

1. A compound represented by the formula (I):

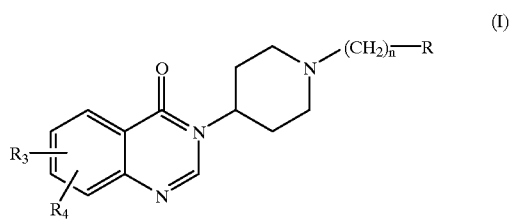

wherein R represents the formula (i):

wherein each of $R_1$ and $R_2$, which may be the same or different, represents a cycloalkyl group with 3 to 7 carbon atoms; an aryl group; or a heteroaryl group with 1 to 3 heteroatoms selected from the group consisting of nitrogen, sulfur, and oxygen atoms, where each of the cycloalkyl, aryl, and heteroaryl group may be substituted with 1 to 3 substituents selected from the group consisting of a halogen atom, a lower alkyl group with 1 to 4 carbon atoms, a lower haloalkyl group with 1 to 4 carbon atoms, a nitro group, a lower alkoxy group with 1 to 4 carbon atoms, an amino group, an amino group substituted with a lower alkyl group with 1 to 4 carbon atoms, a hydroxyl group, a phenoxy group, and a sulfo group, or the formula (ii):

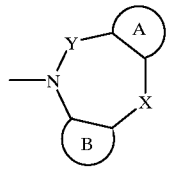

(ii)

wherein each of A and B, which may be the same or different, represents an aromatic hydrocarbon ring; a cycloalkane ring with 3 to 7 carbon atoms; or a cycloalkene ring with 5 to 7 carbon atoms, where each of the aromatic hydrocarbon, cycloalkane, and cycloalkene ring may have 1 to 3 substituents selected from the group consisting of a halogen atom, a lower alkyl group with 1 to 4 carbon atoms, a lower haloalkyl group with 1 to 4 carbon atoms, a hydroxyl group, a nitro group, a lower alkoxy group with 1 to 4 carbon atoms, an amino group, an amino group substituted with a lower alkyl group having 1 to 4 carbon atoms, and a sulfo group, X represents a single bond, a straight chain or branched lower alkylene group with 1 to 4 carbon atoms, a straight chain or branched lower alkenylene group with 2 to 4 carbon atoms, an oxygen atom, a sulfur atom, an imino group which may be substituted with a lower alkyl group with 1 to 4 carbon atoms, a carbonyl group, —O—Z—, —Z—O, —S—Z—, —Z—S—, —NH—Z—, —NR$_5$—Z—, —Z—NH—, or —Z—NR$_5$—, where the lower alkylene or lower alkenylene group may have substituent(s) selected from the group consisting of a halogen atom, a hydroxyl group, a nitro group, a lower alkoxy group with 1 to 4 carbon atoms, an amino group, and a sulfo group, and where Z represents a lower alkylene group with 1 to 4 carbon atoms or a carbonyl group, and R$_5$ represents a lower alkyl group with 1 to 4 carbon atoms; and Y represents a single bond, a straight chain or branched lower alkylene group with 1 to 4 carbon atoms, or a carbonyl group; n represents an integer of 1 to 4; and each of R$_3$ and R$_4$, which may be the same or different, represents a hydrogen atom, a lower alkyl group with 1 to 4 carbon atoms, a halogen atom, a lower haloalkyl group with 1 to 4 carbon atoms, a hydroxyl group, an amino group or a nitro group, or a pharmaceutically acceptable salt thereof.

2. The compound of claim 1, wherein each of R$_1$ and R$_2$, which may be the same or different, represents a cycloalkyl group with 3 to 7 carbon atoms, an aryl group, or a heteroaryl group with 1 to 3 heteroatoms selected from the group consisting of nitrogen, sulfur, and oxygen atoms, where each of the cycloalkyl, aryl, and heteroaryl group may have 1 to 3 substituents selected from the group consisting of a halogen atom, a lower alkyl group with 1 to 4 carbon atoms, a lower haloalkyl group with 1 to 4 carbon atoms, a nitro group, a lower alkoxy group with 1 to 4 carbon atoms, an amino group, an amino group substituted with a lower alkyl group having 1 to 4 carbon atoms, a hydroxyl group, and a sulfo group and wherein each of A and B, which may be the same or different, represents an aromatic hydrocarbon ring; a cycloalkane ring with 3 to 7 carbon atoms; or a cycloalkene ring with 5 to 7 carbon atoms, where each of the aromatic hydrocarbon, cycloalkane, and cycloalkene ring may have 1 to 3 substituents selected from the group consisting of a halogen atom, a lower alkyl group with 1 to 4 carbon atoms, a lower haloalkyl group with 1 to 4 carbon atoms, a hydroxyl group, a nitro group, a lower alkoxy group with 1 to 4 carbon atoms, an amino group, an amino group substituted with a lower alkyl group having 1 to 4 carbon atoms, and a sulfo group, X represents a single bond, a straight chain or branched lower alkylene group with 1 to 4 carbon atoms, a straight chain or branched lower alkenylene group with 2 to 4 carbons, an oxygen atom, a sulfur atom, an imino group which may be substituted with a lower alkyl group having 1 to 4 carbon atoms, a carbonyl group, —O—Z—, —Z—O, —S—Z—, —Z—S—, —NH—Z—, —NR$_5$—Z—, —Z—NH—, or —Z—NR$_5$— where the lower alkylene or lower alkenylene group may have substituent(s) selected from the group consisting of a halogen atom, a hydroxyl group, a nitro group, a lower alkoxy group with 1 to 4 carbon atoms, an amino group, and a sulfo group, and where Z represents a lower alkylene group with 1 to 4 carbon atoms or a carbonyl group, and R$_5$ represents a lower alkyl group with 1 to 4 carbon atoms, and Y represents a single bond, a straight chain or branched lower alkylene group with 1 to 4 carbon atoms, or a carbonyl group, and each of R$_3$ and R$_4$, which may be the same or different, represents a hydrogen atom or a lower alkyl group with 1 to 4 carbon atoms, or a pharmaceutically acceptable salt thereof.

3. The compound of claim 2, wherein each of R$_1$ and R$_2$, which may be the same or different, represents a cycloalkyl group with 3 to 7 carbon atoms, an aryl group, or a heteroaryl group containing 1 to 3 heteroatoms selected from the group consisting of nitrogen, sulfur, and oxygen atoms, where each of the cycloalkyl, aryl, and heteroaryl group may have 1 to 3 substituents selected from the group consisting of a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group, and wherein each of A and B, which may be the same or different, represents an aromatic hydrocarbon ring which may have 1 to 3 substituents selected from the group consisting of a halogen atom, a lower alkyl group with 1 to 4 carbon atoms, a lower haloalkyl group with 1 to 4 carbons atoms, a nitro group, a lower alkoxy group with 1 to 4 carbon atoms, and a hydroxyl group, X represents a single bond, a straight chain or branched lower alkylene group with 1 to 4 carbon atoms, a straight chain or branched lower alkenylene group with 2 to 4 carbon atoms, an oxygen atom, a sulfur atom, an imino group which may be substituted with a lower alkyl group having 1 to 4 carbon atoms, a carbonyl group, —O—Z—, —S—Z—, —NH—Z—, or —NR$_5$—Z—, where the lower alkylene or lower alkenylene group may have substituent(s) selected from the group consisting of a halogen atom, a hydroxyl group, and a lower alkoxy group with 1 to 4 carbon atoms, and where Z represents a lower alkylene group with 1 to 4 carbon atoms or a carbonyl group, and R$_5$ represents a lower alkyl group with 1 to 4 carbon atoms, Y represents a single bond, and R$_3$ and R$_4$ are both hydrogen atoms, or a pharmaceutically acceptable salt thereof.

4. The compound of claim 3, wherein R represents formula (i), or a pharmaceutically acceptable salt thereof.

5. The compound of claim 4, wherein each of $R_1$ and $R_2$, which may be the same or different, represents a cyclohexyl group, a phenyl group, a pyridyl group, a pyrazinyl group, a pyrimidinyl group, a pyridazinyl group, a thienyl group, a furyl group, or a pyrrolyl group, where each of the above groups may have 1 to 3 substituents selected from the group consisting of a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group, or a pharmaceutically acceptable salt thereof.

6. The compound of claim 5, wherein R represents a diphenylamino group, an N-phenyl-N-thienylamino group, an N-phenyl-N-pyridylamino group, a dipyridylamino group, or an N-phenyl-N-pyrimidylamino group, where each of the above groups may have 1 to 3 substituents selected from the group consisting of a halogen atom, a lower alkyl group with 1 to 4 carbon atoms, a lower haloalkyl group with 1 to 4 atoms, a nitro group, a lower alkoxy group with 1 to 4 carbon atoms, and a hydroxyl group, or a pharmaceutically acceptable salt thereof.

7. The compound of claim 3, in which R represents formula (ii), or a pharmaceutically acceptable salt thereof.

8. The compound of claim 7, wherein each of A and B represents a benzene ring, which may have 1 to 3 substituents selected from the group consisting of a halogen atom, a lower alkyl group with 1 to 4 carbon atoms, a lower haloalkyl group with 1 to 4 carbon atoms, a nitro group, a lower alkoxy group with 1 to 4 carbon atoms, and a hydroxyl group, or a pharmaceutically acceptable salt thereof.

9. The compound of claim 8, wherein R represents a carbazol-9-yl group, a phenoxazin-10-yl group, a phenothiazin-10-yl group, an acridon-10-yl group, a 9,9-dimethylacridan-10-yl group, a 10,11-dihydro-5H-dibenzo[b,f]azepin-5-yl group, a 10,11-dihydro-2-hydroxy-5H-dibenzo[b,f]azepin-5-yl group, a 10,11-dihydro-10-hydroxy-5H-dibenzo[b,f]azepin-5-yl group, a 5H-dibenzo[b,f]azepin-5-yl group, a 5,11-dihydrodibenzo[b,e][1,4]oxazepin-5-yl group, a 10,11-dihydro-11-oxo-5H-dibenzo[b,e][1,4]diazepine-5-yl group, or a 11-hydro-10-methyl-11-oxo-5H-dibenzo[b,e][1,4]diazepin-5-yl group, or a pharmaceutically acceptable salt thereof.

10. The compound of claim 3, where the compound is 3-[1-[2-[N-(2-methylphenyl)-N-phenylamino]ethyl]piperidin-4-yl]-3H-quinazolin-4-one, 3-[1-[2-(10,11-dihydro-5H-dibenzo[b,f]-azepin-5-yl)ethyl]piperidin-4-yl]-3H-quinazolin-4-one, 3-[1-[2-(10,11-dihydro-10-hydroxy-5H-dibenzo[b,f]azepin-5-yl)-ethyl]-piperidin-4-yl]-3H-quinazolin-4-one, 3-[1-[2-(10,11-dihydro-2-hydroxy-5H-dibenzo[b,f]azepin-5-yl)ethyl]piperidin-4-yl]-3H-quinazolin-4-one, or 3-[1-[2-(5,11-dihydrodibenzo[b,e][1,4]-oxazepin-5-yl)ethyl]piperidin-4-yl]-3H-quinazolin-4-one, or a pharmaceutically acceptable salt thereof.

11. A pharmaceutical composition comprising the compound of claim 1 or a pharmaceutically acceptable salt thereof, and a pharmacologically acceptable carrier.

12. The compound of claim 1, wherein n is 2 or 3.

13. The compound of claim 12, wherein n is 2.

14. The compound of claim 5, wherein each of $R_1$ and $R_2$, which may be the same or different, is substituted at the ortho position with respect to the atom bonding to the amino nitrogen atom depicted in formula (i).

15. The compound of claim 5, wherein the ortho-substituted substituent is a lower alkyl with 1 to 4 carbon atoms.

16. A method of inhibiting a microsomal triglyceride transfer protein (MTP) by administering to a subject in need thereof an effective amount of a compound of claim 1 or a salt thereof.

17. A method of treating hyperlipemia or arteriosclerosis by administering to a subject in need thereof an effective amount of a compound of claim 1 or a salt thereof.

* * * * *

UNITED STATES PATENT AND TRADEMARK OFFICE
CERTIFICATE OF CORRECTION

PATENT NO.   : 6,235,730 B1  
DATED          : May 22, 2001  
INVENTOR(S)  : Motohide Sato, Takeo Katsushima and Hajime Kinoshita Page 1 of 1

It is certified that error appears in the above-identified patent and that said Letters Patent is hereby corrected as shown below:

<u>Title page,</u>  
Item [86], replace "PCT/JP98/05620" with -- PCT/JP98/05628 --.

Signed and Sealed this

Twenty-sixth Day of February, 2002

Attest:

JAMES E. ROGAN  
*Attesting Officer*   *Director of the United States Patent and Trademark Office*